United States Patent
Sterling et al.

(10) Patent No.: US 7,271,912 B2
(45) Date of Patent: Sep. 18, 2007

(54) METHOD OF DETERMINING ANALYTE CONCENTRATION IN A SAMPLE USING INFRARED TRANSMISSION DATA

(75) Inventors: Bernhard B. Sterling, Sunnyvale, CA (US); James R. Braig, Piedmont, CA (US); Daniel S. Goldberger, Boulder, CO (US); Philip C. Hartstein, Palo Alto, CA (US); Robert D. Gaffney, Atherton, CA (US)

(73) Assignee: OptiScan Biomedical Corporation, Hayward, CA (US)

( * ) Notice: Subject to any disclaimer, the term of this patent is extended or adjusted under 35 U.S.C. 154(b) by 173 days.

(21) Appl. No.: 10/825,085

(22) Filed: Apr. 15, 2004

(65) Prior Publication Data

US 2005/0036147 A1 Feb. 17, 2005

Related U.S. Application Data

(60) Provisional application No. 60/463,133, filed on Apr. 15, 2003.

(51) Int. Cl.
  *G01N 21/00* (2006.01)
  *A61B 5/00* (2006.01)
(52) U.S. Cl. .................. 356/436; 356/433; 600/316
(58) Field of Classification Search ...................
  250/339.02–339.09, 339.12, 341.1, 345,
  250/573; 356/39, 346, 416, 479, 436; 374/161;
  436/63; 600/300, 310–316, 322–336, 373,
  600/474; 702/19, 23, 30; 256/436; 700/23
See application file for complete search history.

(56) References Cited

U.S. PATENT DOCUMENTS

| | | |
|---|---|---|
| 3,787,124 A | 1/1974 | Lowy et al. |
| 3,972,614 A | 8/1976 | Johansen et al. |
| 4,281,645 A | 8/1981 | Jobsis |

(Continued)

FOREIGN PATENT DOCUMENTS

EP 0 982 582 A1 3/2000

(Continued)

OTHER PUBLICATIONS

Kajiwara, K; Fukushima, H; Kishikawa, H; Nishida, K; Hashiguchi, Y; Sakakida, M; Uchara, M; Shichiri, M; ("Spectroscopic Quantitative Analysis Of Blood Glucose By Fourier Transform Infrared Spectroscopy With An Attenuated Total Reflection Prism"; Medical Progress Through Technology 18, No. 3; 1992; pp. 181-189).*

(Continued)

*Primary Examiner*—Gregory J. Toatley, Jr.
*Assistant Examiner*—Jarreas Underwood
(74) *Attorney, Agent, or Firm*—Knobbe Martens Olson & Bear, LLP

(57) ABSTRACT

A method determines an analyte concentration in a sample. The sample includes the analyte and a substance. The method includes providing absorption data of the sample. The method further includes providing reference absorption data of the substance. The method further includes calculating a substance contribution of the absorption data. The method further includes subtracting the substance contribution from the absorption data, thereby providing corrected absorption data substantially free of a contribution from the substance.

43 Claims, 28 Drawing Sheets

U.S. PATENT DOCUMENTS

| | | | |
|---|---|---|---|
| 4,350,441 A | 9/1982 | Wicnienski | |
| 4,397,956 A | 8/1983 | Maggio | |
| 4,655,225 A | 4/1987 | Dahne et al. | |
| 4,730,112 A | 3/1988 | Wong | |
| 4,805,623 A * | 2/1989 | Jobsis | 600/328 |
| 4,819,752 A | 4/1989 | Zelin | |
| 4,927,264 A | 5/1990 | Shiga et al. | |
| 4,969,115 A | 11/1990 | Rosenthal | |
| 5,070,874 A | 12/1991 | Barnes et al. | |
| 5,081,998 A | 1/1992 | Yelderman et al. | |
| 5,111,817 A | 5/1992 | Clark et al. | |
| 5,204,532 A | 4/1993 | Rosenthal | |
| 5,252,829 A * | 10/1993 | Nygaard et al. | 250/339.09 |
| 5,277,181 A | 1/1994 | Mendelson et al. | |
| 5,297,548 A | 3/1994 | Pologe | |
| 5,313,941 A | 5/1994 | Braig et al. | |
| 5,348,003 A | 9/1994 | Caro | |
| 5,361,758 A | 11/1994 | Hall et al. | |
| 5,370,114 A | 12/1994 | Wong et al. | |
| 5,371,020 A | 12/1994 | Frischauf | |
| 5,372,135 A | 12/1994 | Mendelson et al. | |
| 5,372,136 A | 12/1994 | Steuer et al. | |
| 5,377,674 A | 1/1995 | Kuestner | |
| 5,379,764 A | 1/1995 | Barnes et al. | |
| 5,412,581 A | 5/1995 | Tackett | |
| 5,452,716 A * | 9/1995 | Clift | 600/373 |
| 5,481,113 A | 1/1996 | Dou et al. | |
| 5,499,627 A | 3/1996 | Steuer et al. | |
| 5,569,591 A | 10/1996 | Kell et al. | |
| 5,576,544 A | 11/1996 | Rosenthal | |
| 5,606,164 A * | 2/1997 | Price et al. | 250/339.09 |
| 5,630,413 A | 5/1997 | Thomas et al. | |
| 5,655,530 A | 8/1997 | Messerschmidt | |
| 5,692,503 A | 12/1997 | Kuestner | |
| 5,710,630 A * | 1/1998 | Essenpreis et al. | 356/479 |
| 5,713,353 A | 2/1998 | Castano | |
| 5,720,284 A | 2/1998 | Aoyagi et al. | |
| 5,725,480 A | 3/1998 | Oosta et al. | |
| 5,773,301 A | 6/1998 | Ziegler | |
| 5,823,951 A | 10/1998 | Messerschmidt | |
| 5,830,132 A | 11/1998 | Robinson | |
| 5,857,462 A | 1/1999 | Thomas et al. | |
| 5,876,121 A * | 3/1999 | Burns et al. | 374/161 |
| 5,900,632 A | 5/1999 | Sterling et al. | |
| 6,040,578 A | 3/2000 | Malin et al. | |
| 6,061,582 A * | 5/2000 | Small et al. | 600/316 |
| 6,064,898 A * | 5/2000 | Aldrich | 600/316 |
| 6,067,463 A * | 5/2000 | Jeng et al. | 600/336 |
| 6,087,182 A | 7/2000 | Jeng et al. | |
| 6,115,673 A * | 9/2000 | Malin et al. | 702/23 |
| 6,119,026 A | 9/2000 | McNulty et al. | |
| 6,121,050 A | 9/2000 | Han | |
| 6,122,052 A | 9/2000 | Barnes et al. | |
| 6,124,134 A | 9/2000 | Stark | |
| 6,157,041 A | 12/2000 | Thomas et al. | |
| 6,161,028 A | 12/2000 | Braig et al. | |
| 6,198,949 B1 | 3/2001 | Braig et al. | |
| 6,236,047 B1 | 5/2001 | Malin et al. | |
| 6,262,798 B1 | 7/2001 | Shepherd et al. | |
| 6,278,889 B1 | 8/2001 | Robinson | |
| 6,285,448 B1 | 9/2001 | Kuestner | |
| 6,304,767 B1 * | 10/2001 | Soller et al. | 600/322 |
| 6,404,501 B1 * | 6/2002 | Hafeman et al. | 356/436 |
| 6,426,045 B1 | 7/2002 | Jeng et al. | |
| 6,441,388 B1 * | 8/2002 | Thomas et al. | 250/573 |
| 6,486,474 B1 * | 11/2002 | Owen et al. | 250/339.02 |
| 6,542,762 B1 * | 4/2003 | Alam et al. | 600/310 |
| 6,580,934 B1 | 6/2003 | Braig et al. | |
| 6,862,534 B2 * | 3/2005 | Sterling et al. | 702/23 |
| 7,047,055 B2 * | 5/2006 | Boas et al. | 600/338 |
| 7,115,841 B2 * | 10/2006 | Zeng et al. | 219/476 |
| 2002/0038079 A1 * | 3/2002 | Steuer et al. | 600/322 |
| 2002/0041371 A1 | 4/2002 | Shepherd et al. | |
| 2003/0090649 A1 | 5/2003 | Sterling et al. | |
| 2003/0133118 A1 | 7/2003 | Braig et al. | |

FOREIGN PATENT DOCUMENTS

| | | |
|---|---|---|
| WO | WO93/13706 | 7/1993 |
| WO | WO99/39631 | 8/1999 |
| WO | WO 01/30236 A1 | 5/2001 |
| WO | PCT/US02/40133 | 6/2003 |
| WO | PCT/US03/04548 | 9/2003 |

OTHER PUBLICATIONS

U.S. Appl. No. 10/319,409, filed Dec. 12, 2002, Sterling et al.
U.S. Appl. No. 10/366,540, filed Feb. 12, 2003, Sterling et al.
U.S. Appl. No. 60/463,133, filed Apr. 15, 2003, Sterling et al.
U.S. Appl. No. 10/825,223, filed Apr. 15, 2004, (Inventors not yet named).
U.S. Appl. No. 10/826,004, filed Apr. 15, 2004, Braig et al.
Burmeister, Jason J., et al., "*Spectroscopic Considerations for Noninvasive Blood Glucose Measurements with Near Infrared Spectroscopy*," IEEE Infrared Spectroscopy Newsletter, Apr. 1998, pp. 1-5.
De Lène Mirouze, F., et al., "*Quantitative Analysis of Glucose Syrups by ATR/FT-IR Spectroscopy*," Applied Spectroscopy, vol. 47, No. 8, 1993, pp. 1187-1191.
Heise, H.M., et al., "*Multicomponent Assay for Blood Substrates in Human Plasma by Mid-Infrared Spectroscopy and its Evaluation for Clinical Analysis*," Applied Spectroscopy, vol. 48, No. 1, 1994, pp. 85-95.
Janatsch, Günter, et al., "*Multivariate Calibration for Assays in Clinical Chemistry Using Attenuated Total Reflection Infrared Spectra of Human Blood Plasma*," Analytical Chemistry, 1989, 61, pp. 2016-2023.
Kajiwara, Ken-ichiro et al., *Spectroscopic Quantitative Analysis of Blood Glucose by Fourier Transform Infrared Spectroscopy with an Attenuated Total Reflection Prism*, Medical Progress through Technology 18,No. 3, 1992, Dordrecht, NL, pp. 181-189.
Kuenstner, J. Todd, et al., "*Spectrophotometry of Human Hemoglobin in the Midinfrared Region*," 1997, pp. 225-232.
Lewis, Christopher B., et al., *Investigation of Near-Infrared Spectroscopy for Periodic Determination of Glucose in Cell Culture Media in Situ*, Applied Spectroscopy, vol. 54, No. 10, 2000, pp. 1453-1457.
McShane, Michael J., et al, "*Near-Infrared Spectroscopy for Determination of Glucose, Lactate, and Ammonia in Cell Culture Media*," Applied Spectroscopy, vol. 52, No. 8, 1998, pp. 1073-1078.
Norris, K.H., et al., "*Rapid Measurement of Analytes in Whole Blood with NIR Transmittance*," Leaping Ahead with Near Infrared Spectroscopy, 1995, pp. 431-436.
Petibois, Cyril, et al., "*Glucose and Lactate Concentration Determination on Single Microsamples by Fourier-Transform Infrared Spectroscopy*," INSERM U 443, Equipe deChimie Bio-Organique, Oct. 1999, pp. 210-215.
Shaw, R. Anthony, et al., "*Infrared Spectroscopy in Clinical and Diagnostic Analysis*," Encyclopedia of Analytical Chemistry, pp. 1-20.
Ward, Kenneth J., et al., "*Post-Prandial Blood Glucose Determination by Quantitative Mid-Infrared Spectroscopy*," Applied Spectroscopy, vol. 46, No. 6, 1992, pp. 959-965.

* cited by examiner

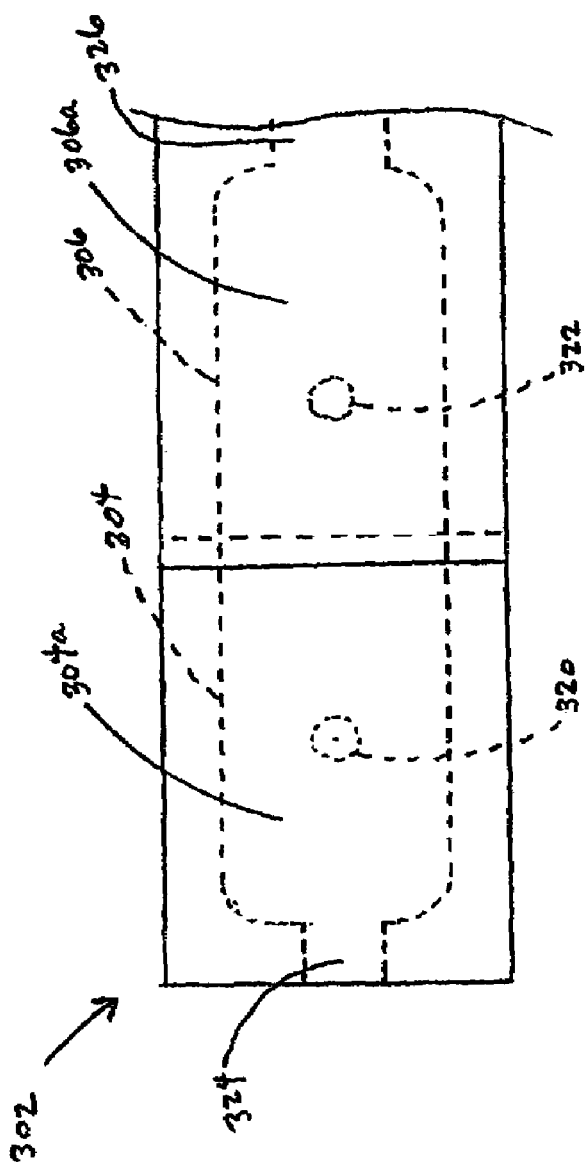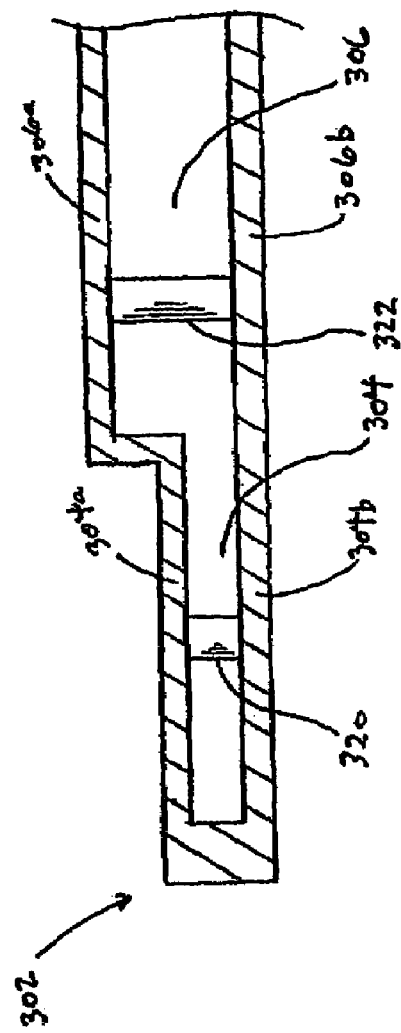
FIG. 17
FIG. 18

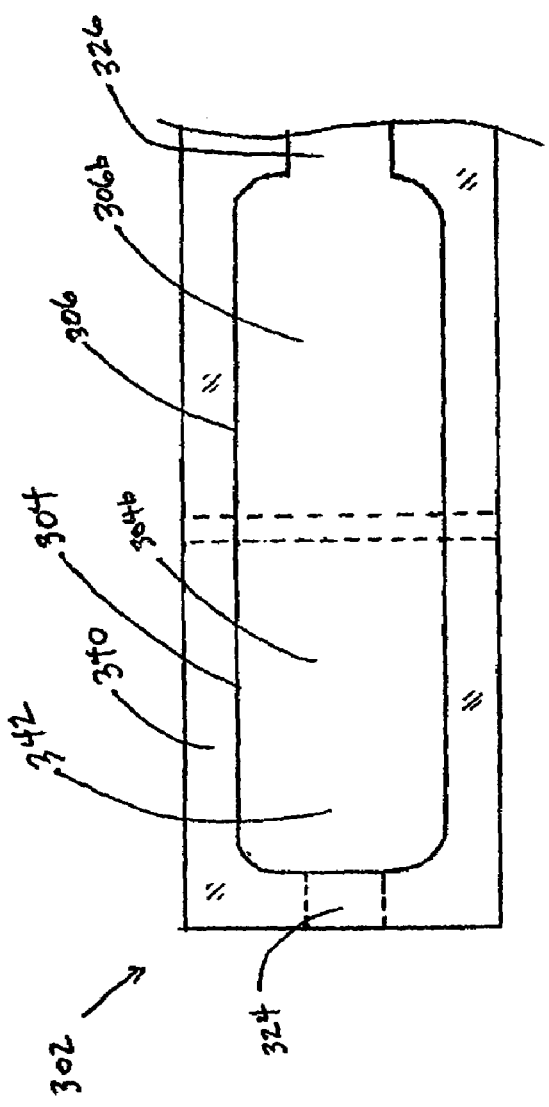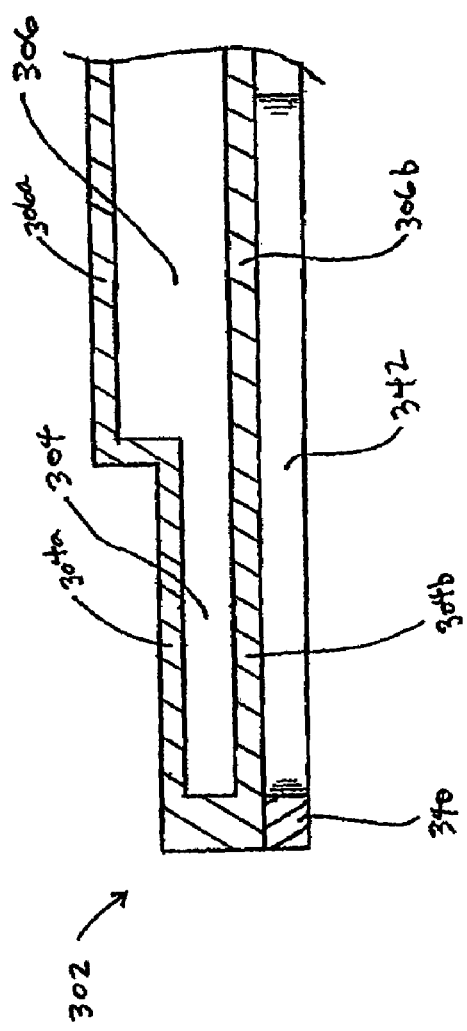

METHOD OF DETERMINING ANALYTE CONCENTRATION IN A SAMPLE USING INFRARED TRANSMISSION DATA

CLAIM OF PRIORITY

This application claims the benefit of U.S. Provisional Application No. 60/463,133, filed Apr. 15, 2003, which is hereby incorporated herein in its entirety by this reference.

BACKGROUND OF THE INVENTION

1. Field of the Invention

The disclosure herein relates generally to methods for determining the composition of a material sample by analyzing electromagnetic energy that has been passed through or emitted from the material sample.

2. Description of the Related Art

A large number of people suffer from diabetes and other conditions in which the natural regulation of blood glucose levels is impaired. For these people, monitoring blood glucose level is an important part of health maintenance, and a variety of techniques and instruments have been developed to periodically measure glucose levels in blood samples for this purpose.

Most of these methods involve a spectroscopic measurement, where the absorption of electromagnetic energy of a blood sample is measured and correlated to glucose concentration. In some cases, the electromagnetic energy is at optical wavelengths. In these systems, a chemical reagent is typically added to the blood sample which chemically reacts with the glucose and produces an absorption in the optical band dependent on the amount of glucose present and which participates in the reaction. In addition to the expense of manufacturing such reagent based systems, these assays may be interfered with by other blood constituents that reduce their accuracy and reproducibility.

Although reagent-based optical assays have been successfully produced and commercialized, blood absorption characteristics in the infrared (IR) region of the electromagnetic spectrum have been recently explored to measure blood glucose concentrations. Using IR absorption characteristics has advantages over reagent-based optical measurements since glucose exhibits significant absorption in several IR wavelength regions without the need to perform a reaction with another chemical species that must be added to the blood sample.

However, other chemical species including water, alanine, albumin, hemoglobin, urea, lactate and others also absorb strongly at several IR band frequencies. Some of these constituents are present in the blood at concentrations of 50 or 100 times or more than the glucose concentration. Because the sample absorption at any given wavelength is a sum of the absorptions of each component at that wavelength, IR absorption measurements are complicated by the presence of these other components. Consequently, methods that allow effective compensation and adjustments to measured IR absorption for the presence of other blood components would be beneficial to provide a low cost and accurate system for diabetics and others in need of periodic glucose monitoring.

SUMMARY OF THE INVENTION

In certain embodiments, a method determines an analyte concentration in a sample. The sample comprises the analyte and a substance. The method comprises providing absorption data of the sample. The method further comprises providing reference absorption data of the substance. The method further comprises calculating a substance contribution of the absorption data. The method further comprises subtracting the substance contribution from the absorption data, thereby providing corrected absorption data substantially free of a contribution from the substance.

In certain embodiments, a method provides measurements of constituents in a sample using infrared (IR) spectroscopy. The method comprises providing absorption data of the sample. The method further comprises correcting the absorption data for a non-analyte contribution to the absorption data.

In certain embodiments, a method uses infrared (IR) spectroscopy to determine a ratio of an analyte volume to the total volume of a sample. The sample comprises the analyte, a first substance, and a second substance. The method comprises providing absorption data from the sample for a first set of wavelengths in a wavelength region where a first-substance absorption dominates. The method further comprises calculating a first quantity equal to the product of a first-substance volume concentration and a path length of the sample. The method further comprises providing absorption data from the sample for a second set of wavelengths in a wavelength region where the first-substance absorption and a second-substance absorption dominate. The method further comprises calculating a second quantity equal to the product of a second-substance volume concentration and the path length of the sample. The method further comprises providing absorption data from the sample for a third set of wavelengths in a wavelength region where the first-substance absorption, the second-substance absorption, and an analyte absorption dominate. The method further comprises calculating a third quantity equal to the product of an analyte volume concentration and the path length of the sample. The method further comprises calculating a ratio of the third quantity divided by the sum of the first quantity and the second quantity.

In certain embodiments, a method determines non-analyte contributions to absorption data from a sample. The method comprises inputting transmission measurements, filter parameters, and water spectral properties. The method further comprises calculating optical densities and filter constants. The method further comprises estimating non-linear filter terms and cuvette distortion matrix elements. The method further comprises solving for a temperature change as a function of the path length. The method further comprises calculating new estimates of absorption and non-linear terms.

In certain embodiments, a method determines non-analyte contributions to absorption data from a sample. The method comprises inputting transmission measurements, filter parameters, and water spectral properties. The method further comprises calculating optical densities and filter constants. The method further comprises estimating non-linear filter terms and cuvette distortion matrix elements. The method further comprises solving for a temperature change as a function of the path length. The method further comprises calculating new estimates of absorption and non-linear terms.

In certain embodiments, a method evaluates analyte concentration errors in absorption data from a sample. The method comprises calculating transmission and optical densities at four wavelengths for a water-filled cuvette. The four wavelengths comprise two wavelengths dominated by absorption by water, an analyte reference wavelength, and a measurement wavelength. The method further comprises using the optical densities to determine the water content at the analyte reference wavelength and the measurement wavelength. The method further comprises calculating expected optical density values at the analyte reference wavelength and the measurement wavelength. The method further comprises calculating residuals between the exact and calculated optical densities at the analyte reference wavelength and the measurement wavelength. The method further comprises determining the analyte concentration error by calculating the analyte concentration consistent with the difference between the residuals at the analyte reference wavelength and the measurement wavelength.

For purposes of summarizing the invention, certain aspects, advantages and novel features of the invention have been described herein above. It is to be understood, however, that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 17 is a top plan view of another embodiment of a sample element configured for analysis of a sample at two separate pathlengths.

FIG. 18 is a sectional view of the sample element of FIG. 17.

FIG. 19 is a bottom plan view of another embodiment of a sample element configured for analysis of a sample at two separate pathlengths.

FIG. 20 is a sectional view of the sample element of FIG. 19.

DETAILED DESCRIPTION OF THE PREFERRED EMBODIMENT

Figure 1:
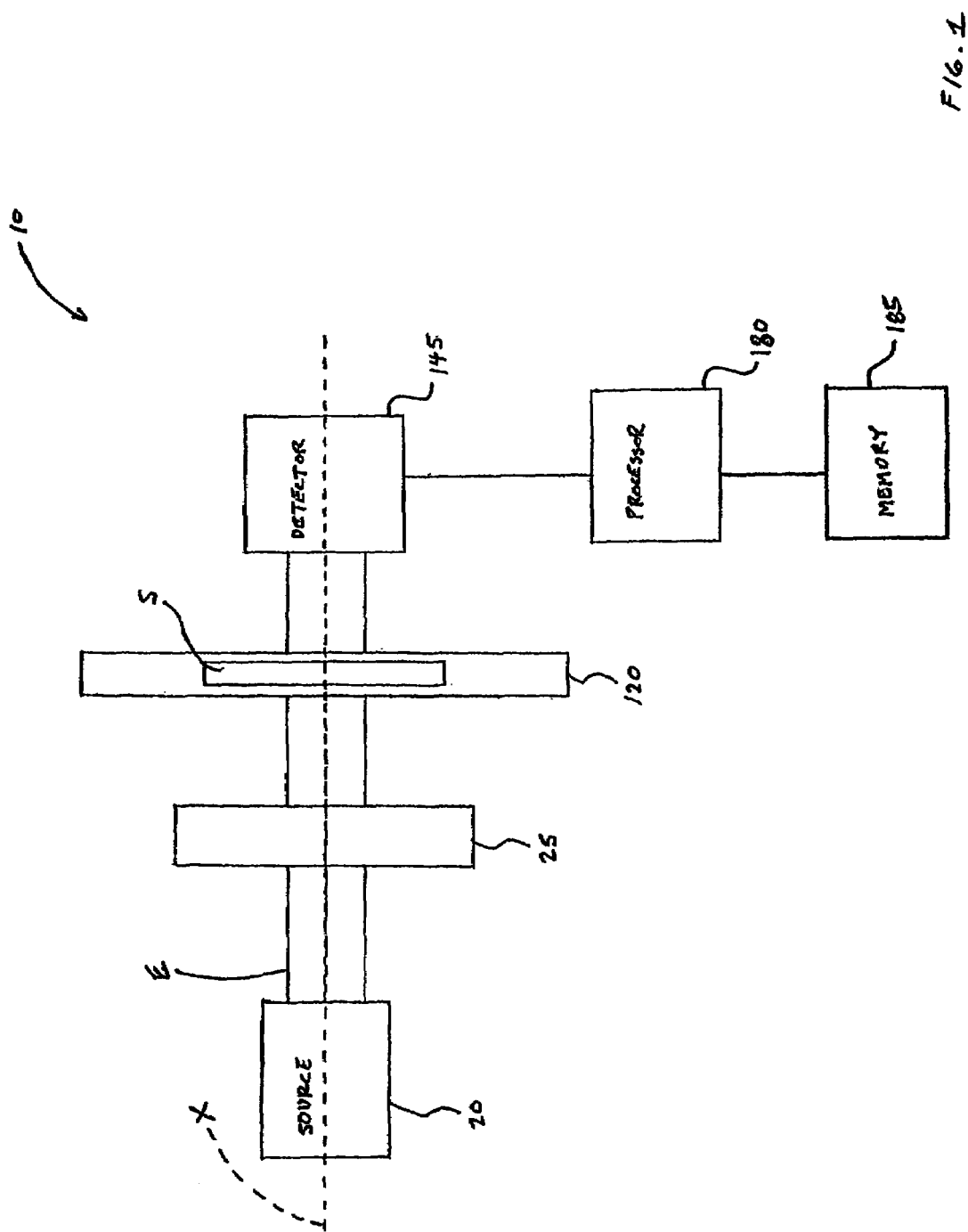
FIG. 1 is a schematic illustration of one embodiment of an analyte detection system.

Although certain preferred embodiments and examples are disclosed below, it will be understood by those skilled in the art that the invention extends beyond the specifically disclosed embodiments to other alternative embodiments and/or uses of the invention and obvious modifications and equivalents thereof. Thus it is intended that the scope of the invention herein disclosed should not be limited by the particular disclosed embodiments described below. In any method or process disclosed herein, the acts or operations making up the method/process may be performed in any suitable sequence, and are not necessarily limited to any particular disclosed sequence. For purposes of contrasting various embodiments with the prior art, certain aspects and advantages of these embodiments are described where appropriate herein. Of course, it is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Section I below discloses various embodiments of an analyte detection system that may be used to detect the concentration of one or more analytes in a material sample. Section II discloses various embodiments of a cuvette or sample element which are suitable for use with the embodiments of the analyte detection system discussed in Section I. The disclosed embodiments of the sample element are configured to support or contain a material sample for analysis by the analyte detection system. In Section III, there are disclosed a number of methods for sample-element referencing, which generally comprises compensating for the effects of the sample element itself on the measurement of analyte concentration. Any one or combination of the methods disclosed in Section III may be executed wholly or partly by appropriate processing hardware in the analyte detection system to support computation of the concentration of the analyte(s) of interest in the sample. Section III also discloses further variations of the analyte detection system and sample element, which are adapted for use in practicing the disclosed methods of sample-element referencing.

Section IV below discusses a number of computational methods or algorithms which may be used to calculate the concentration of the analyte(s) of interest in the sample, and/or to compute or estimate other measures that may be used in support of calculations of analyte concentrations. Any one or combination of the algorithms disclosed in Section IV may be executed by appropriate processing hardware in the analyte detection system to compute the concentration of the analyte(s) of interest in the sample. Section V discusses a number of measures of the performance of certain embodiments of the analyte detection system.

I. ANALYTE DETECTION SYSTEM

FIG. 1 is a schematic view of one embodiment of an analyte detection system 10. The detection system 10 is particularly suited for detecting the concentration of one or more analytes in a material sample S, by detecting energy transmitted through the sample, as will be discussed in further detail below.

The detection system 10 comprises an energy source 20 disposed along a major axis X of the system 10. When activated, the energy source 20 generates an energy beam E which advances from the energy source 20 along the major axis X. In one embodiment, the energy source 20 comprises an infrared source and the energy beam E comprises an infrared energy beam.

The energy beam E passes through a filter 25, also situated on the major axis X, before reaching a sample element or cuvette 120, which supports or contains the material sample S. After passing through the sample element 120 and the sample S, the energy beam E reaches a detector 145.

With further reference to FIG. 1, the detector 145 responds to radiation incident thereon by generating an electrical signal and passing the signal to a processor 180 for analysis. Based on the signal(s) passed to it by the detector 145, the processor computes the concentration of the analyte(s) of interest in the sample S, and/or the absorbance/transmittance characteristics of the sample S at one or more wavelengths or wavelength bands employed to analyze the sample. The processor 180 computes the concentration(s), absorbance(s), transmittance(s), etc. by executing a data processing algorithm or program instructions residing within memory 185 accessible by the processor 180.

In the embodiment shown in FIG. 1, the filter 25 may comprise a varying-passband filter, to facilitate changing, over time and/or during a measurement taken with the detection system 10, the wavelength or wavelength band of the energy beam E that may pass the filter 25 for use in analyzing the sample S. Some examples of a varying-passband filter usable with the detection system 10 include, but are not limited to, a filter wheel (discussed in further detail below), electronically tunable filter, Fabry-Perot interferometer, or any other suitable varying-passband filter.

When the energy beam E is filtered with a varying-passband filter, the absorption/transmittance characteristics of the sample S can be analyzed at a number of wavelengths or wavelength bands in a separate, sequential manner. As an example, assume that it is desired to analyze the sample S at four separate wavelengths (Wavelength 1 through Wavelength 4). The varying-passband filter is first operated or tuned to permit the energy beam E to pass at Wavelength 1, while substantially blocking the beam E at most or all other wavelengths to which the detector 145 is sensitive (including Wavelengths 2-4). The absorption/transmittance properties of the sample S are then measured at Wavelength 1, based on the beam E that passes through the sample S and reaches the detector 145. The varying-passband filter is then operated or tuned to permit the energy beam E to pass at Wavelength 2, while substantially blocking other wavelengths as discussed above; the sample S is then analyzed at Wavelength 2 as was done at Wavelength 1. This process is repeated until all of the wavelengths of interest have been employed to analyze the sample S. The collected absorption/transmittance data can then be analyzed by the processor 180 to determine the concentration of the analyte(s) of interest in the material sample S.

By analyzing the sample S at each wavelength or wavelength band in this separate, sequential fashion, greater precision can be attained because the noise, interference, etc. otherwise caused by the detection of wavelengths other than the wavelength of immediate interest, is minimized. However, any other suitable detection methodology may be used with the detection system 10, whether or not the system 10 includes a varying-passband filter.

Although the use of a varying-passband filter offers certain advantages as discussed above, a fixed-passband filter may be used as an alternative filter 25, to permit a selected wavelength or wavelength band to pass through the sample S for analysis thereof.

As used herein, the term "material sample" (or, alternatively, "sample") is a broad term and is used in its ordinary sense and includes, without limitation, any collection of material which is suitable for analysis by the analyte detection system 10. For example, the material sample S may comprise whole blood, blood components (e.g., plasma or serum), interstitial fluid, intercellular fluid, saliva, urine, sweat and/or other organic or inorganic materials, or derivatives of any of these materials. In one embodiment, whole blood or blood components may be drawn from a patient's capillaries. As used herein, the term "analyte" is a broad term and is used in its ordinary sense and includes, without limitation, any chemical species the presence or concentration of which is sought in the material sample S by the analyte detection system 10. For example, the analyte(s) which may be detected by the analyte detection system 10 include but not are limited to glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, electrolytes, sodium, potassium, chloride, bicarbonate, and hormones.

Figure 2:
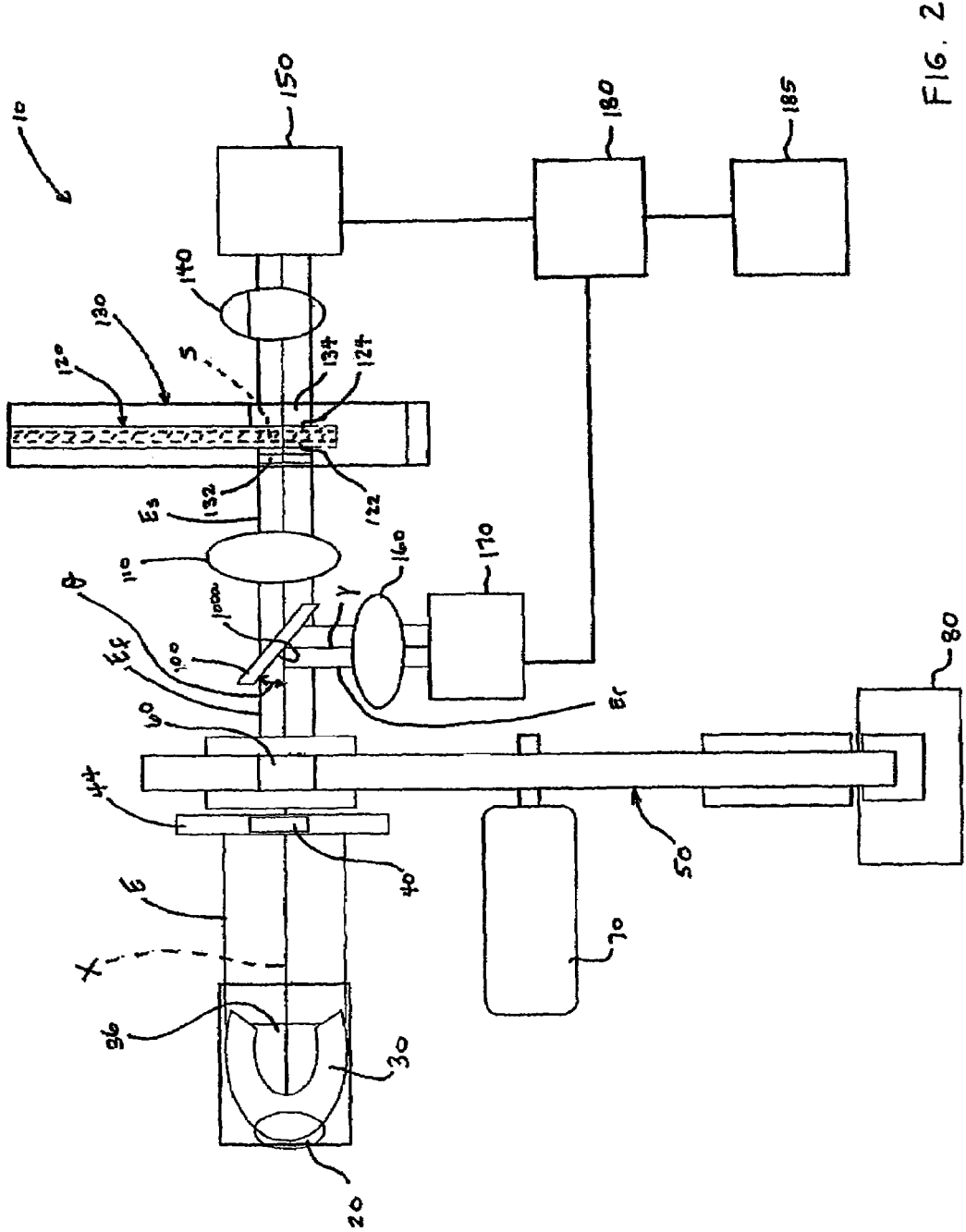
FIG. 2 is a schematic illustration of another embodiment of the analyte detection system.

FIG. 2 depicts another embodiment of the analyte detection system 10, which may be generally similar to the embodiment illustrated in FIG. 1, except as further detailed below. Where possible, similar elements are identified with identical reference numerals in the depiction of the embodiments of FIGS. 1 and 2.

The detection system 10 shown in FIG. 2 includes a collimator 30 through which the energy beam E passes before reaching a primary filter 40 disposed downstream of a wide end 36 of the collimator 30. The primary filter 40 is aligned with the source 20 and collimator 30 on the major axis X and is preferably configured to operate as a broadband filter, allowing only a selected band, e.g., between about 2.5 µm and about 12.5 µm, of wavelengths emitted by the source 20 to pass therethrough, as discussed below. In one embodiment, the energy source 20 comprises an infrared source and the energy beam E comprises an infrared energy beam. One suitable energy source 20 is the TOMA TECH™ IR-50 available from HawkEye Technologies of Milford, Conn.

With further reference to FIG. 2, the primary filter 40 is mounted in a mask 44 so that only those portions of the energy beam E which are incident on the primary filter 40 can pass the plane of the mask-primary filter assembly. The primary filter 40 is generally centered on and oriented orthogonal to the major axis X and is preferably circular (in a plane orthogonal to the major axis X) with a diameter of about 8 mm. Of course, any other suitable size or shape may be employed. As discussed above, the primary filter 40 preferably operates as a broadband filter. In the illustrated embodiment, the primary filter 40 preferably allows only energy wavelengths between about 4 µm and about 11 µm to pass therethrough. However, other ranges of wavelengths can be selected. The primary filter 40 advantageously reduces the filtering burden of secondary filter(s) 60 disposed downstream of the primary filter 40 and improves the rejection of electromagnetic radiation having a wavelength outside of the desired wavelength band. Additionally, the primary filter 40 can help minimize the heating of the secondary filter(s) 60 by the energy beam E passing therethrough. Despite these advantages, the primary filter 40 and/or mask 44 may be omitted in alternative embodiments of the system 10 shown in FIG. 2.

The primary filter 40 is preferably configured to substantially maintain its operating characteristics (center wavelength, passband width) where some or all of the energy beam E deviates from normal incidence by a cone angle of up to about twelve degrees relative to the major axis X. In further embodiments, this cone angle may be up to about 15 degrees or 20 degrees. The primary filter 40 may be said to "substantially maintain" its operating characteristics where any changes therein are insufficient to affect the performance or operation of the detection system 10 in a manner that would raise significant concerns for the user(s) of the system in the context in which the system 10 is employed.

In the embodiment illustrated in FIG. 2, a filter wheel 50 is employed as a varying-passband filter, to selectively position the secondary filter(s) 60 on the major axis X and/or in the energy beam E. The filter wheel 50 can therefore selectively tune the wavelength(s) of the energy beam E downstream of the wheel 50. These wavelength(s) vary according to the characteristics of the secondary filter(s) 60 mounted in the filter wheel 50. The filter wheel 50 positions the secondary filter(s) 60 in the energy beam E in a "one-at-a-time" fashion to sequentially vary, as discussed above, the wavelengths or wavelength bands employed to analyze the material sample S.

In alternative arrangements, the single primary filter 40 depicted in FIG. 2 may be replaced or supplemented with additional primary filters mounted on the filter wheel 50 upstream of each of the secondary filters 60. As yet another alternative, the primary filter 40 could be implemented as a primary filter wheel (not shown) to position different primary filters on the major axis X at different times during operation of the detection system 10, or as a tunable filter.

Figure 3:
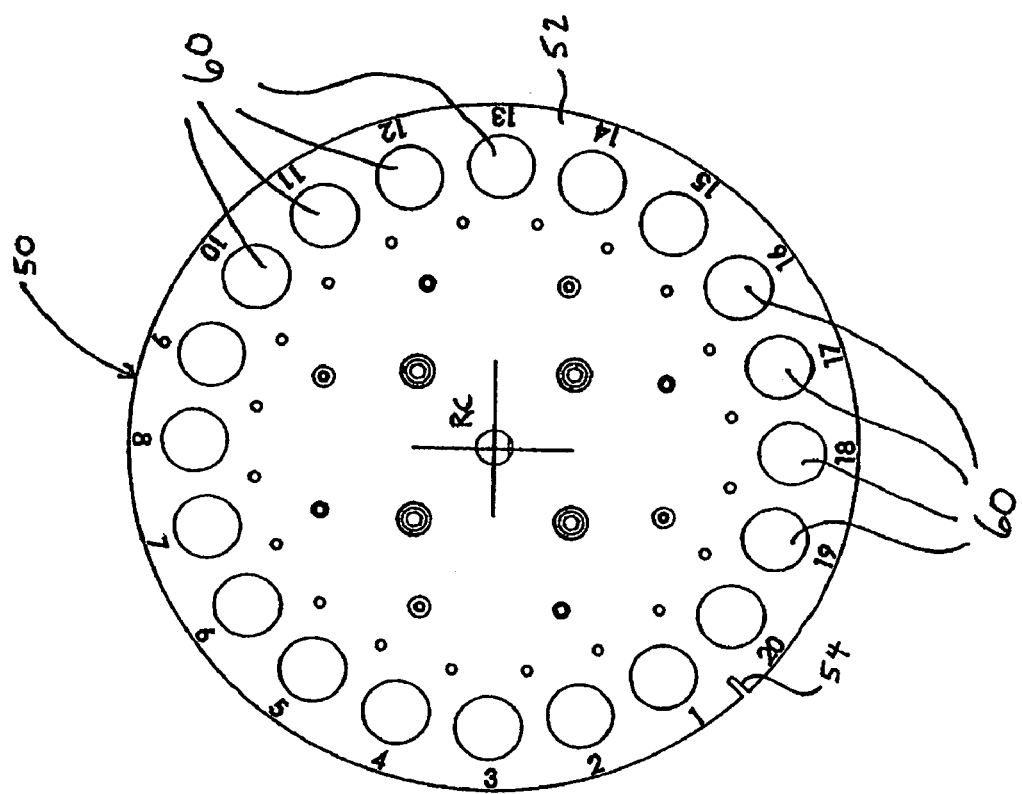
FIG. 3 is a plan view of one embodiment of a filter wheel suitable for use in the analyte detection system depicted in FIG. 2.

The filter wheel 50, in the embodiment depicted in FIG. 3, can comprise a wheel body 52 and a plurality of secondary filters 60 disposed on the body 52, the center of each filter being equidistant from a rotational center RC of the wheel body. The filter wheel 50 is configured to rotate about an axis which is (i) parallel to the major axis X and (ii) spaced from the major axis X by an orthogonal distance approximately equal to the distance between the rotational center RC and any of the center(s) of the secondary filter(s) 60. Under this arrangement, rotation of the wheel body 52 advances each of the filters sequentially through the major axis X, so as to act upon the energy beam E. (However, depending on the analyte(s) of interest or desired measurement speed, only a subset of the filters on the wheel 50 may be employed in a given measurement run.) In the embodiment depicted in FIG. 3, the wheel body 52 is circular; however, any suitable shape, such as oval, square, rectangular, triangular, etc. may be employed. A home position notch 54 may be provided to indicate the home position of the wheel 50 to the position sensor 80.

In one embodiment, the wheel body 52 can be formed from molded plastic, with each of the secondary filters 60 having a 5 mm×5 mm square configuration and a thickness of 1 mm. Each of the filters 60, in this embodiment of the wheel body 52, is axially aligned with a circular aperture of 4 mm diameter, and the aperture centers define a circle of about 1.70 inches diameter, which circle is concentric with the wheel body 52. The body 52 itself is circular, with an outside diameter of 2.00 inches.

Each of the secondary filter(s) 60 is preferably configured to operate as a narrow band filter, allowing only a selected energy wavelength or wavelength band (i.e., a filtered energy beam (Ef) to pass therethrough. As the filter wheel 50 rotates about its rotational center RC, each of the secondary filter(s) 60 is, in turn, disposed along the major axis X for a selected dwell time corresponding to each of the secondary filter(s) 60.

The "dwell time" for a given secondary filter 60 is the time interval, in an individual measurement run of the system 10, during which both of the following conditions are true: (i) the filter is disposed on the major axis X; and (ii) the source 20 is energized. The dwell time for a given filter may be greater than or equal to the time during which the filter is disposed on the major axis X during an individual measurement run. In one embodiment of the analyte detection system 10, the dwell time corresponding to each of the secondary filter(s) 60 is less than about 1 second. However, the secondary filter(s) 60 can have other dwell times, and each of the filter(s) 60 may have a different dwell time during a given measurement run.

Referring again to FIG. 2, a stepper motor 70 is connected to the filter wheel 50 and is configured to generate a force to rotate the filter wheel 50. Additionally, a position sensor 80 is disposed over a portion of the circumference of the filter wheel 50 and may be configured to detect the angular position of the filter wheel 50 and to generate a corresponding filter wheel position signal, thereby indicating which filter is in position on the major axis X. Alternatively, the stepper motor 70 may be configured to track or count its own rotation(s), thereby tracking the angular position of the filter wheel, and pass a corresponding position signal to the processor 180. Two suitable position sensors are models EE-SPX302-W2A and EE-SPX402-W2A available from Omron Corporation of Kyoto, Japan.

From the secondary filter 60, the filtered energy beam (Ef) passes through a beam splitter 100 disposed along the major axis X and having a face 100a disposed at an included angle θ relative to the major axis X. The splitter 100 preferably separates the filtered energy beam (Ef) into a sample beam (Es) and a reference beam (Er).

With further reference to FIG. 2, the sample beam (Es) passes next through a first lens 110 aligned with the splitter 100 along the major axis X. The first lens 110 is configured to focus the sample beam (Es) generally along the axis X onto the material sample S. The sample S is preferably disposed in a sample element 120 between a first window 122 and a second window 124 of the sample element 120. The sample element 120 is further preferably removably disposed in a holder 130, and the holder 130 has a first opening 132 and a second opening 134 configured for alignment with the first window 122 and second window 124, respectively. Alternatively, the sample element 120 and sample S may be disposed on the major axis X without use of the holder 130.

At least a fraction of the sample beam (Es) is transmitted through the sample S and continues onto a second lens 140 disposed along the major axis X. The second lens 140 is configured to focus the sample beam (Es) onto a sample detector 150, thus increasing the flux density of the sample beam (Es) incident upon the sample detector 150. The sample detector 150 is configured to generate a signal corresponding to the detected sample beam (Es) and to pass the signal to a processor 180, as discussed in more detail below.

The reference beam (Er) is directed from the beam splitter 100 to a third lens 160 disposed along a minor axis Y generally orthogonal to the major axis X. The third lens 160 is configured to focus the reference beam (Er) onto a reference detector 170, thus increasing the flux density of the reference beam (Er) incident upon the reference detector 170. In one embodiment, the lenses 110, 140, 160 may be formed from a material which is highly transmissive of infrared radiation, for example germanium or silicon. In addition, any of the lenses 110, 140 and 160 may be implemented as a system of lenses, depending on the desired optical performance. The reference detector 170 is also configured to generate a signal corresponding to the detected reference beam (Er) and to pass the signal to the processor 180, as discussed in more detail below. Except as noted below, the sample and reference detectors 150, 170 may be generally similar to the detector 145 illustrated in FIG. 1. Based on signals received from the sample and reference detectors 150, 170, the processor 180 computes the concentration(s), absorbance(s), transmittance(s), etc. relating to the sample S by executing a data processing algorithm or program instructions residing within the memory 185 accessible by the processor 180.

In further variations of the detection system 10 depicted in FIG. 2, the beam splitter 100, reference detector 170 and other structures on the minor axis Y may be omitted, especially where the output intensity of the source 20 is sufficiently stable to obviate any need to reference the source intensity in operation of the detection system 10. Furthermore, in any of the embodiments of the analyte detection system 10 disclosed herein, the processor 180 and/or memory 185 may reside partially or wholly in a standard personal computer ("PC") coupled to the detection system 10.

Figure 4:
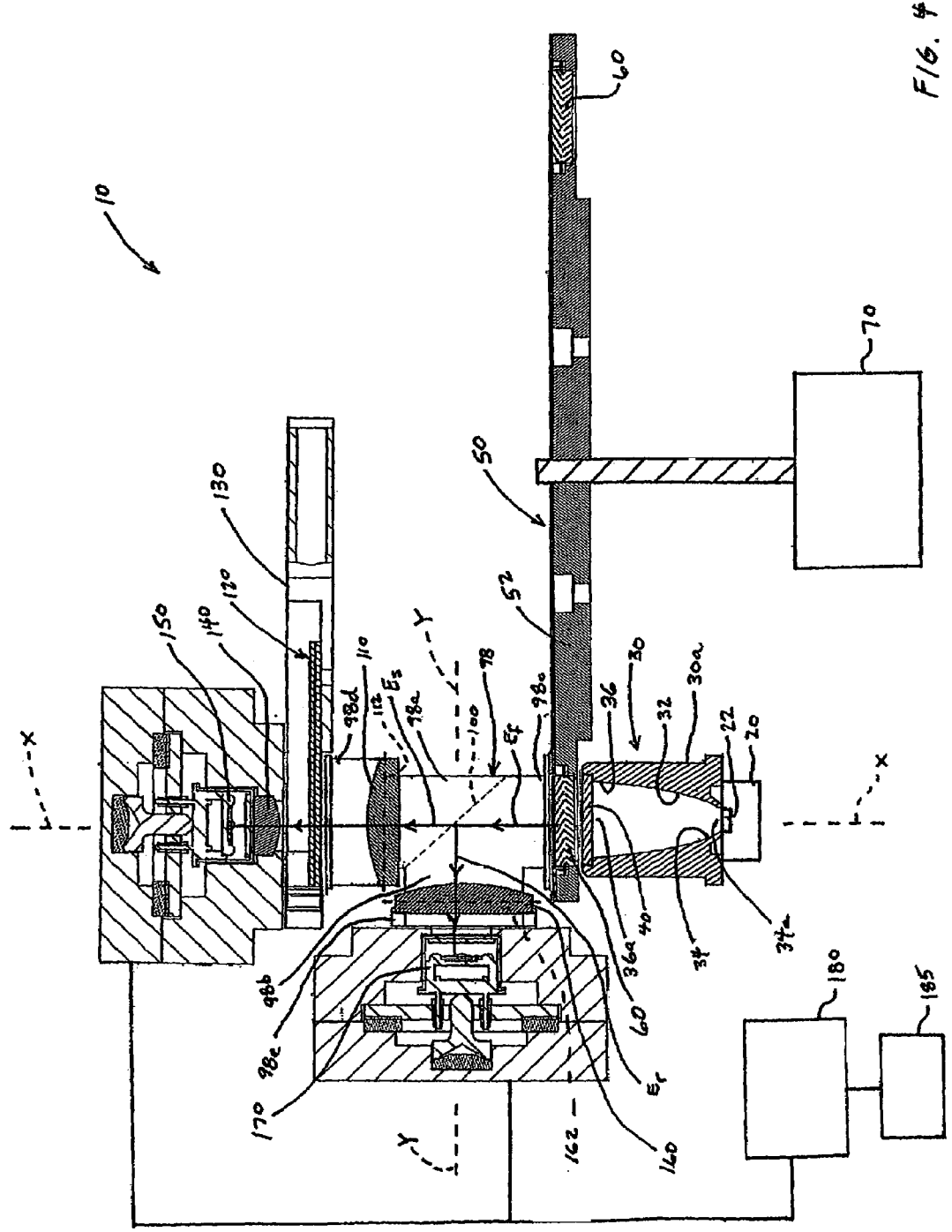
FIG. 4 is a partial sectional view of another embodiment of an analyte detection system.

FIG. 4 depicts a partial cross-sectional view of another embodiment of an analyte detection system 10, which may be generally similar to any of the embodiments illustrated in FIGS. 1-3, except as further detailed below. Where possible, similar elements are identified with identical reference numerals in the depiction of the embodiments of FIGS. 1-4.

The energy source 20 of the embodiment of FIG. 4 preferably comprises an emitter area 22 which is substantially centered on the major axis X. In one embodiment, the emitter area 22 may be square in shape. However the emitter area 22 can have other suitable shapes, such as rectangular, circular, elliptical, etc. One suitable emitter area 22 is a square of about 1.5 mm on a side; of course, any other suitable shape or dimensions may be employed.

The energy source 20 is preferably configured to selectably operate at a modulation frequency between about 1 Hz and 30 Hz and have a peak operating temperature of between about 1070 degrees Kelvin and 1170 degrees Kelvin. Additionally, the source 20 preferably operates with a modulation depth greater than about 80% at all modulation frequencies.

The energy source 20 preferably emits electromagnetic radiation in any of a number of spectral ranges, e.g., within infrared wavelengths; in the mid-infrared wavelengths; above about 0.8 μm; between about 5.0 μm and about 20.0 μm; and/or between about 5.25 μm and about 12.0 μm. However, in other embodiments, the detection system 10 may employ an energy source 20 which is unmodulated and/or which emits in wavelengths found anywhere from the visible spectrum through the microwave spectrum, for example anywhere from about 0.4 μm to greater than about 100 μm. In still other embodiments, the energy source 20 can emit electromagnetic radiation in wavelengths between about 3.5 μm and about 14 μm, or between about 0.8 μm and about 2.5 μm, or between about 2.5 μm and 20 μm, or between about 20 μm and about 100 μm, or between about 6.85 μm and about 10.10 μm. In yet other embodiments, the energy source 20 can emit electromagnetic radiation within the radio frequency (RF) range or the terahertz range. All of the above-recited operating characteristics are merely exemplary, and the source 20 may have any operating characteristics suitable for use with the analyte detection system 10.

A power supply (not shown) for the energy source 20 is preferably configured to selectably operate with a duty cycle of between about 30% and about 70%. Additionally, the power supply is preferably configured to selectably operate at a modulation frequency of about 10 Hz, or between about 1 Hz and about 30 Hz. The operation of the power supply can be in the form of a square wave, a sine wave, or any other waveform defined by a user.

With further reference to FIG. 4, the collimator 30 comprises a tube 30a with one or more highly-reflective inner surfaces 32 which diverge from a relatively narrow upstream end 34 to a relatively wide downstream end 36 as they extend downstream, away from the energy source 20. The narrow end 34 defines an upstream aperture 34a which is situated adjacent the emitter area 22 and permits radiation generated by the emitter area to propagate downstream into the collimator. The wide end 36 defines a downstream aperture 36a. Like the emitter area 22, each of the inner surface(s) 32, upstream aperture 34a and downstream aperture 36a is preferably substantially centered on the major axis X.

As illustrated in FIG. 4, the inner surface(s) 32 of the collimator may have a generally curved shape, such as a parabolic, hyperbolic, elliptical or spherical shape. One suitable collimator 30 is a compound parabolic concentrator (CPC). In one embodiment, the collimator 30 can be up to about 20 mm in length. In another embodiment, the collimator 30 can be up to about 30 mm in length. However, the collimator 30 can have any length, and the inner surface(s) 32 may have any shape, suitable for use with the analyte detection system 10.

The inner surfaces 32 of the collimator 30 cause the rays making up the energy beam E to straighten (i.e., propagate at angles increasingly parallel to the major axis X) as the beam E advances downstream, so that the energy beam E becomes increasingly or substantially cylindrical and oriented substantially parallel to the major axis X. Accordingly, the inner surfaces 32 are highly reflective and minimally absorptive in the wavelengths of interest, such as infrared wavelengths.

The tube 30a itself may be fabricated from a rigid material such as aluminum, steel, etc., as long as the inner surfaces 32 are coated or otherwise treated to be highly reflective in the wavelengths of interest. For example, a polished gold coating may be employed. Preferably, the inner surface(s) 32 of the collimator 30 define a circular cross-section when viewed orthogonal to the major axis X; however, other cross-sectional shapes, such as a square or other polygonal shapes, parabolic or elliptical shapes may be employed in alternative embodiments.

As noted above, the filter wheel 50 shown in FIG. 4 comprises a plurality of secondary filters 60 which preferably operate as narrow band filters, each filter allowing only energy of a certain wavelength or wavelength band to pass therethrough. In one configuration suitable for detection of glucose in a sample S, the filter wheel 50 comprises twenty or twenty-two secondary filters 60, each of which is configured to allow a filtered energy beam (Ef) to travel therethrough with a nominal wavelength approximately equal to one of the following: 3 μm, 4.06 μm, 4.6 μm, 4.9 μm, 5.25 μm, 6.12 μm, 6.47 μm, 7.98 μm, 8.35 μm, 9.65 μm, and 12.2 μm. (Moreover, this set of wavelengths may be employed with any of the embodiments of the analyte detection system 10 disclosed herein.) Each secondary filter's 60 center wavelength is preferably equal to the desired nominal wavelength plus or minus about 2%. Additionally, the secondary filters 60 are preferably configured to have a bandwidth of about 0.2 μm, or alternatively equal to the nominal wavelength plus or minus about 2%-10%.

In another embodiment, the filter wheel 50 comprises twenty secondary filters 60, each of which is configured to allow a filtered energy beam (Ef) to travel therethrough with a nominal center wavelengths of: 4.275 μm, 4.5 μm, 4.7 μm, 5.0 μm, 5.3 μm, 6.056 μm, 7.15 μm, 7.3 μm, 7.55 μm, 7.67 μm, 8.06 μm, 8.4 μm, 8.56 μm, 8.87 μm, 9.15 μm, 9.27 μm, 9.48 μm, 9.68 μm, 9.82 μm, and 10.06 μm. (This set of wavelengths may also be employed with or in any of the embodiments of the analyte detection system 10 disclosed herein.) In still another embodiment, the secondary filters 60 may conform to any one or combination of the following specifications: center wavelength tolerance of ±0.01 μm; half-power bandwidth tolerance of ±0.01 μm; peak transmission greater than or equal to 75%; cut-on/cut-off slope less than 2%; center-wavelength temperature coefficient less than 0.01% per degree Celsius; out of band attenuation greater than OD 5 from 3 μm to 12 μm; flatness less than 1.0 waves at 0.6328 μm; surface quality of E-E per Mil-F-48616; and overall thickness of about 1 mm.

In still another embodiment, the secondary filters mentioned above may conform to any one or combination of the following half-power bandwidth ("HPBW") specifications:

| Center Wavelength (μm) | HPBW (μm) |
|---|---|
| 4.275 | 0.05 |
| 4.5 | 0.18 |
| 4.7 | 0.13 |
| 5.0 | 0.1 |
| 5.3 | 0.13 |
| 6.056 | 0.135 |
| 7.15 | 0.19 |
| 7.3 | 0.19 |
| 7.55 | 0.18 |
| 7.67 | 0.197 |
| 8.06 | 0.3 |
| 8.4 | 0.2 |
| 8.56 | 0.18 |
| 8.87 | 0.2 |
| 9.15 | 0.15 |
| 9.27 | 0.14 |
| 9.48 | 0.23 |
| 9.68 | 0.3 |
| 9.82 | 0.34 |
| 10.06 | 0.2 |

In still further embodiments, the secondary filters may have a center wavelength tolerance of ±0.5% and a half-power bandwidth tolerance of ±0.02 µm.

Of course, the number of secondary filters employed, and the center wavelengths thereof, may vary in further embodiments of the system 10, whether such further embodiments are employed to detect glucose, or other analytes instead of or in addition to glucose. For example, in another embodiment, the filter wheel 50 can have fewer than fifty secondary filters 60. In still another embodiment, the filter wheel 50 can have fewer than twenty secondary filters 60. In yet another embodiment, the filter wheel 50 can have fewer than ten secondary filters 60.

In one embodiment, the secondary filters 60 each measure about 10 mm long by 10 mm wide in a plane orthogonal to the major axis X, with a thickness of about 1 mm. However, the secondary filters 60 can have any other dimensions suitable for operation of the analyte detection system 10. Additionally, the secondary filters 60 are preferably configured to operate at a temperature of between about 5° C. and about 35° C. and to allow transmission of more than about 75% of the energy beam E therethrough in the wavelength(s) which the filter is configured to pass.

According to the embodiment illustrated in FIG. 4, the primary filter 40 operates as a broadband filter and the secondary filters 60 disposed on the filter wheel 50 operate as narrow band filters. However, one of ordinary skill in the art will realize that other structures can be used to filter energy wavelengths according to the embodiments described herein. For example, the primary filter 40 may be omitted and/or an electronically tunable filter or Fabry-Perot interferometer (not shown) can be used in place of the filter wheel 50 and secondary filters 60. Such a tunable filter or interferometer can be configured to permit, in a sequential, "one-at-a-time" fashion, each of a set of wavelengths or wavelength bands of electromagnetic radiation to pass therethrough for use in analyzing the material sample S.

A reflector tube 98 is preferably positioned to receive the filtered energy beam (Ef) as it advances from the secondary filter(s) 60. The reflector tube 98 is preferably secured with respect to the secondary filter(s) 60 to substantially prevent introduction of stray electromagnetic radiation, such as stray light, into the reflector tube 98 from outside of the detection system 10. The inner surfaces of the reflector tube 98 are highly reflective in the relevant wavelengths and preferably have a cylindrical shape with a generally circular cross-section orthogonal to the major and/or minor axis X, Y. However, the inner surface of the tube 98 can have a cross-section of any suitable shape, such as oval, square, rectangular, etc. Like the collimator 30, the reflector tube 98 may be formed from a rigid material such as aluminum, steel, etc., as long as the inner surfaces are coated or otherwise treated to be highly reflective in the wavelengths of interest. For example, a polished gold coating may be employed.

According to the embodiment illustrated in FIG. 4, the reflector tube 98 preferably comprises a major section 98a and a minor section 98b. As depicted, the reflector tube 98 can be T-shaped with the major section 98a having a greater length than the minor section 98b. In another example, the major section 98a and the minor section 98b can have the same length. The major section 98a extends between a first end 98c and a second end 98d along the major axis X. The minor section 98b extends between the major section 98a and a third end 98e along the minor axis Y.

The major section 98a conducts the filtered energy beam (Ef) from the first end 98c to the beam splitter 100, which is housed in the major section 98a at the intersection of the major and minor axes X, Y. The major section 98a also conducts the sample beam (Es) from the beam splitter 100, through the first lens 110 and to the second end 98d. From the second end 98d the sample beam (Es) proceeds through the sample element 120, holder 130 and second lens 140, and to the sample detector 150. Similarly, the minor section 98b conducts the reference beam (Er) from the beam splitter 100, through the third lens 160 and to the third end 98e. From the third end 98e the reference beam (Er) proceeds to the reference detector 170.

The sample beam (Es) preferably comprises from about 75% to about 85% of the energy of the filtered energy beam (Ef). More preferably, the sample beam (Es) comprises about 80% of the energy of the filtered energy beam (Es). The reference beam (Er) preferably comprises from about 15% and about 25% of the energy of the filtered energy beam (Es). More preferably, the reference beam (Er) comprises about 20% of the energy of the filtered energy beam (Ef). Of course, the sample and reference beams may take on any suitable proportions of the energy beam E.

The reflector tube 98 also houses the first lens 110 and the third lens 160. As illustrated in FIG. 4, the reflector tube 98 houses the first lens 110 between the beam splitter 100 and the second end 98d. The first lens 110 is preferably disposed so that a plane 112 of the lens 110 is generally orthogonal to the major axis X. Similarly, the tube 98 houses the third lens 160 between the beam splitter 100 and the third end 98e. The third lens 160 is preferably disposed so that a plane 162 of the third lens 160 is generally orthogonal to the minor axis Y. The first lens 110 and the third lens 160 each has a focal length configured to substantially focus the sample beam (Es) and reference beam (Er), respectively, as the beams (Es, Er) pass through the lenses 110, 160. In particular, the first lens 110 is configured, and disposed relative to the holder 130, to focus the sample beam (Es) so that substantially the entire sample beam (Es) passes through the material sample S, residing in the sample element 120. Likewise, the third lens 160 is configured to focus the reference beam (Er) so that substantially the entire reference beam (Er) impinges onto the reference detector 170.

The sample element 120 is retained within the holder 130, which is preferably oriented along a plane generally orthogonal to the major axis X. The holder 130 is configured to be slidably displaced between a loading position and a measurement position within the analyte detection system 10. In the measurement position, the holder 130 contacts a stop edge 136 which is located to orient the sample element 120 and the sample S contained therein on the major axis X.

The structural details of the holder 130 depicted in FIG. 4 are unimportant, so long as the holder positions the sample element 120 and sample S on and substantially orthogonal to the major axis X, while permitting the energy beam E to pass through the sample element and sample. As with the embodiment depicted in FIG. 2, the holder 130 may be omitted and the sample element 120 positioned alone in the depicted location on the major axis X. However, the holder 130 is useful where the sample element 120 (discussed in further detail below) is constructed from a highly brittle or fragile material, such as barium fluoride, or is manufactured to be extremely thin.

As with the embodiment depicted in FIG. 2, the sample and reference detectors 150, 170 shown in FIG. 4 respond to radiation incident thereon by generating signals and passing them to the processor 180. Based these signals received from the sample and reference detectors 150, 170, the processor 180 computes the concentration(s), absorbance(s), transmittance(s), etc. relating to the sample S by executing a data processing algorithm or program instructions residing within the memory 185 accessible by the processor 180. In further variations of the detection system 10 depicted in FIG. 4, the beam splitter 100, reference detector 170 and other structures on the minor axis Y may be omitted, especially where the output intensity of the source 20 is sufficiently stable to obviate any need to reference the source intensity in operation of the detection system 10.

Figure 5:
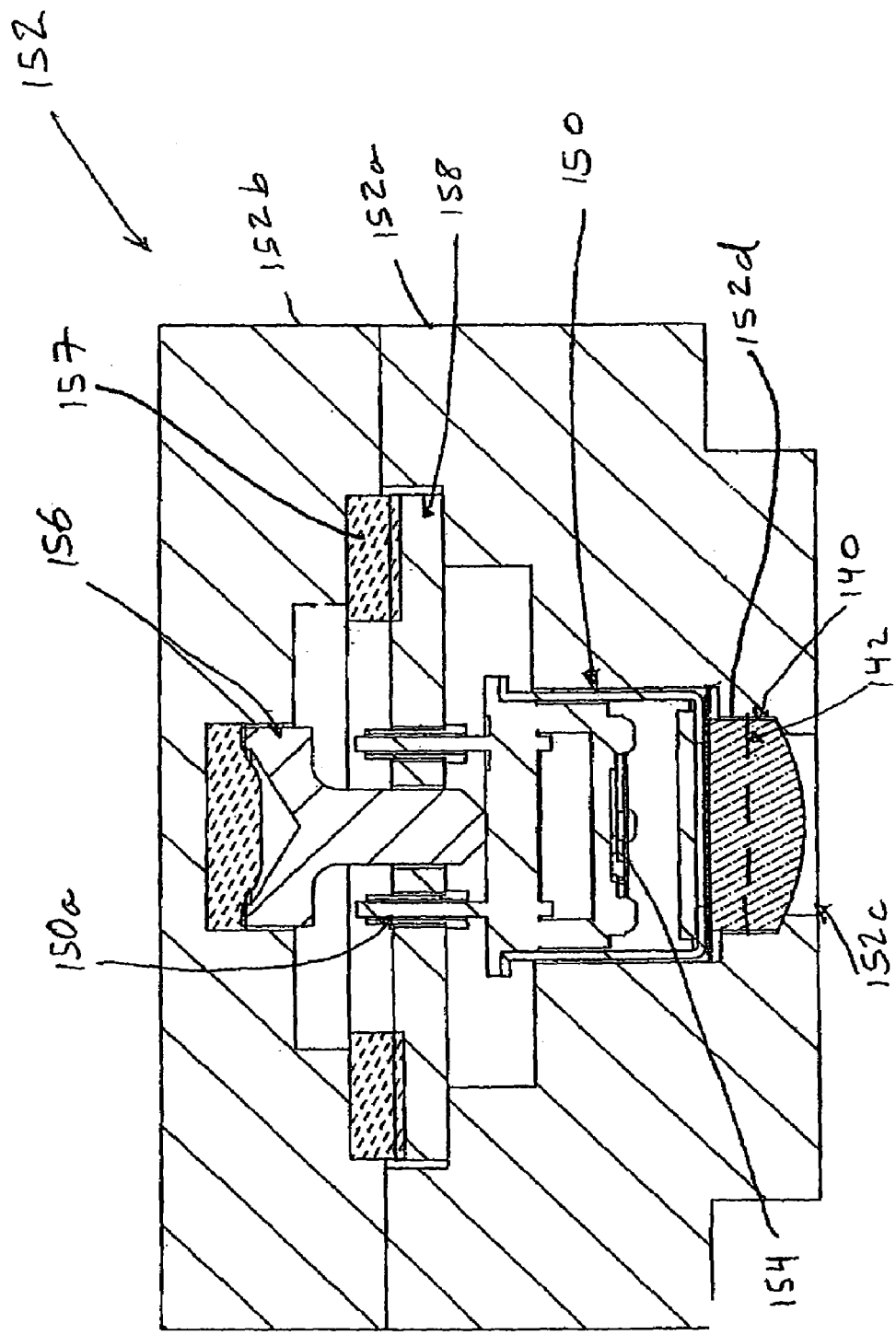
FIG. 5 is a detailed sectional view of a sample detector of the analyte detection system illustrated in FIG. 4.

FIG. 5 depicts a sectional view of the sample detector 150 in accordance with one embodiment. The sample detector 150 is mounted in a detector housing 152 having a receiving portion 152*a* and a cover 152*b*., However, any suitable structure may be used as the sample detector 150 and housing 152. The receiving portion 152*a* preferably defines an aperture 152*c* and a lens chamber 152*d*, which are generally aligned with the major axis X when the housing 152 is mounted in the analyte detection system 10. The aperture 152*c* is configured to allow at least a fraction of the sample beam (Es) passing through the sample S and the sample element 120 to advance through the aperture 152*c* and into the lens chamber 152*d*.

The receiving portion 152*a* houses the second lens 140 in the lens chamber 152*d* proximal to the aperture 152*c*. The sample detector 150 is also disposed in the lens chamber 152*d* downstream of the second lens 140 such that a detection plane 154 of the detector 150 is substantially orthogonal to the major axis X. The second lens 140 is positioned such that a plane 142 of the lens 140 is substantially orthogonal to the major axis X. The second lens 140 is configured, and is preferably disposed relative to the holder 130 and the sample detector 150, to focus substantially all of the sample beam (Es) onto the detection plane 154, thereby increasing the flux density of the sample beam (Es) incident upon the detection plane 154.

With further reference to FIG. 5, a support member 156 preferably holds the sample detector 150 in place in the receiving portion 152*a*. In the illustrated embodiment, the support member 156 is a spring 156 disposed between the sample detector 150 and the cover 152*b*. The spring 156 is configured to maintain the detection plane 154 of the sample detector 150 substantially orthogonal to the major axis X. A gasket 157 is preferably disposed between the cover 152*b* and the receiving portion 152*a* and surrounds the support member 156.

The receiving portion 152*a* preferably also houses a printed circuit board 158 disposed between the gasket 157 and the sample detector 150. The board 158 connects to the sample detector 150 through at least one connecting member 150*a*. The sample detector 150 is configured to generate a detection signal corresponding to the sample beam (Es) incident on the detection plane 154. The sample detector 150 communicates the detection signal to the circuit board 158 through the connecting member 150*a*, and the board 158 transmits the detection signal to the processor 180.

In one embodiment, the sample detector 150 comprises a generally cylindrical housing 150*a*, e.g., a type TO-39 "metal can" package, which defines a generally circular housing aperture 150*b* at its "upstream" end. In one embodiment, the housing 150*a* has a diameter of about 0.323 inches and a depth of about 0.248 inches, and the aperture 150*b* may have a diameter of about 0.197 inches.

A detector window 150*c* is disposed adjacent the aperture 150*b*, with its upstream surface preferably about 0.078 inches (+/−0.004 inches) from the detection plane 154. (The detection plane 154 is located about 0.088 inches (+/−0.004 inches) from the upstream edge of the housing 150*a*, where the housing has a thickness of about 0.010 inches.) The detector window 150*c* is preferably transmissive of infrared energy in at least a 3-12 micron passband; accordingly, one suitable material for the window 150*c* is germanium. The endpoints of the passband may be "spread" further to less than 2.5 microns, and/or greater than 12.5 microns, to avoid unnecessary absorbance in the wavelengths of interest. Preferably, the transmittance of the detector window 150*c* does not vary by more than 2% across its passband. The window 150*c* is preferably about 0.020 inches in thickness. The sample detector 150 preferably substantially retains its operating characteristics across a temperature range of −20 to +60 degrees Celsius.

Figure 6:
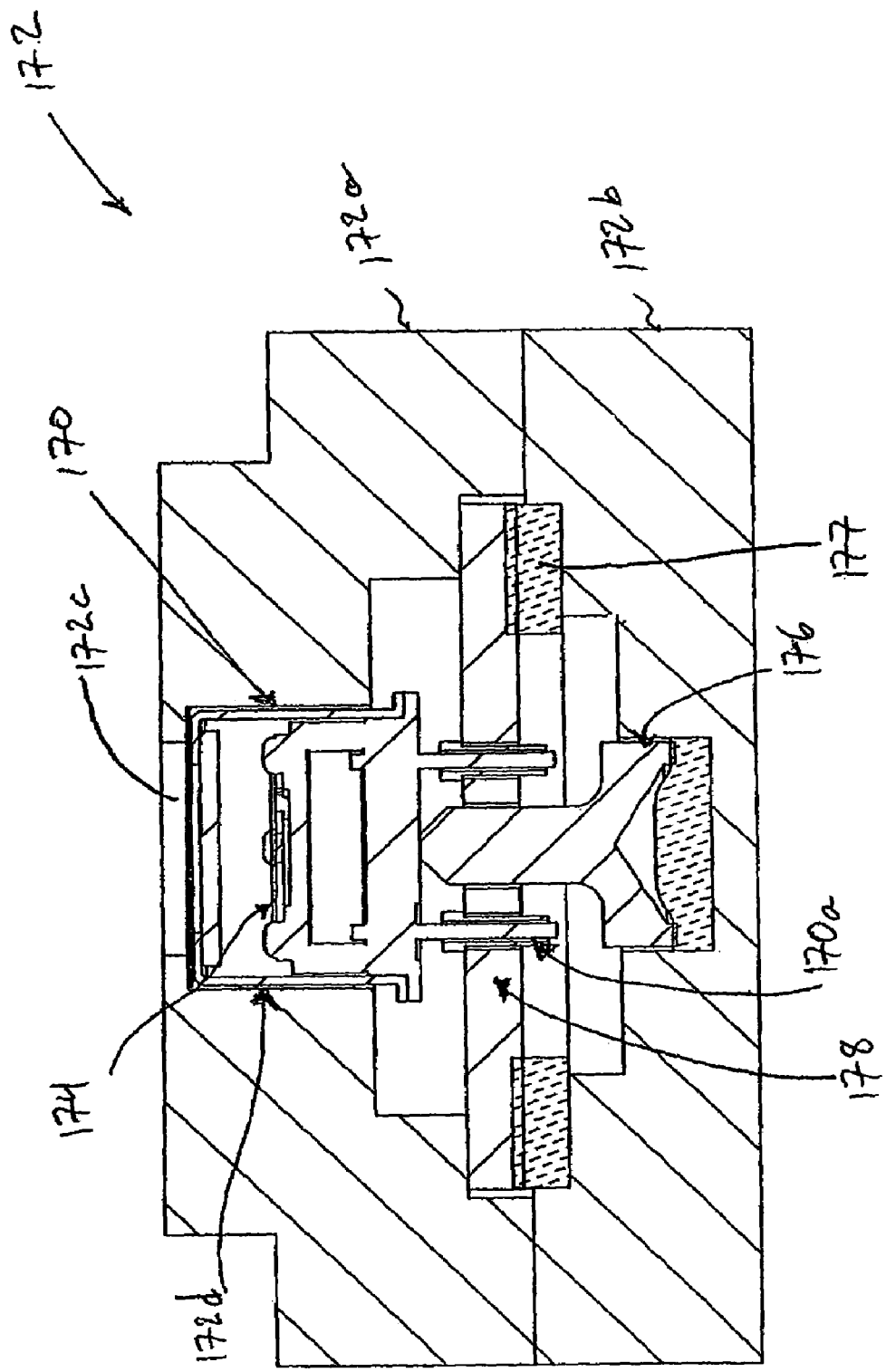
FIG. 6 is a detailed sectional view of a reference detector of the analyte detection system illustrated in FIG. 4.

FIG. 6 depicts a sectional view of the reference detector 170 in accordance with one embodiment. The reference detector 170 is mounted in a detector housing 172 having a receiving portion 172*a* and a cover 172*b*. However, any suitable structure may be used as the sample detector 150 and housing 152. The receiving portion 172*a* preferably defines an aperture 172*c* and a chamber 172*d* which are generally aligned with the minor axis Y, when the housing 172 is mounted in the analyte detection system 10. The aperture 172*c* is configured to allow the reference beam (Er) to advance through the aperture 172*c* and into the chamber 172*d*.

The receiving portion 172*a* houses the reference detector 170 in the chamber 172*d* proximal to the aperture 172*c*. The reference detector 170 is disposed in the chamber 172*d* such that a detection plane 174 of the reference detector 170 is substantially orthogonal to the minor axis Y. The third lens 160 is configured to substantially focus the reference beam (Er) so that substantially the entire reference beam (Er) impinges onto the detection plane 174, thus increasing the flux density of the reference beam (Er) incident upon the detection plane 174.

With further reference to FIG. 6, a support member 176 preferably holds the reference detector 170 in place in the receiving portion 172*a*. In the illustrated embodiment, the support member 176 is a spring 176 disposed between the reference detector 170 and the cover 172*b*. The spring 176 is configured to maintain the detection plane 174 of the reference detector 170 substantially orthogonal to the minor axis Y. A gasket 177 is preferably disposed between the cover 172*b* and the receiving portion 172*a* and surrounds the support member 176.

The receiving portion 172*a* preferably also houses a printed circuit board 178 disposed between the gasket 177 and the reference detector 170. The board 178 connects to the reference detector 170 through at least one connecting member 170*a*. The reference detector 170 is configured to generate a detection signal corresponding to the reference beam (Er) incident on the detection plane 174. The reference detector 170 communicates the detection signal to the circuit board 178 through the connecting member 170*a*, and the board 178 transmits the detection signal to the processor 180.

In one embodiment, the construction of the reference detector 170 is generally similar to that described above with regard to the sample detector 150.

In one embodiment, the sample and reference detectors 150, 170 are both configured to detect electromagnetic radiation in a spectral wavelength range of between about 0.8 μm and about 25 μm. However, any suitable subset of the foregoing set of wavelengths can be selected. In another embodiment, the detectors 150, 170 are configured to detect electromagnetic radiation in the wavelength range of between about 4 μm and about 12 μm. The detection planes 154, 174 of the detectors 150, 170 may each define an active area about 2 mm by 2 mm or from about 1 mm by 1 mm to about 5 mm by 5 mm; of course, any other suitable dimensions and proportions may be employed. Additionally, the detectors 150, 170 may be configured to detect electromagnetic radiation directed thereto within a cone angle of about 45 degrees from the major axis X.

In one embodiment, the sample and reference detectors 150, 170 further comprise a system (not shown) for regulating the temperature of the detectors. Such a temperature-regulation system may comprise a suitable electrical heat source, thermistor, and a proportional-plus-integral-plus-derivative (PID) control. These components may be used to regulate the temperature of the detectors 150, 170 at about 35° C. The detectors 150, 170 can also optionally be operated at other desired temperatures. Additionally, the PID control preferably has a control rate of about 60 Hz and, along with the heat source and thermistor, maintains the temperature of the detectors 150, 170 within about 0.1° C. of the desired temperature.

The detectors 150, 170 can operate in either a voltage mode or a current mode, wherein either mode of operation preferably includes the use of a pre-amp module. Suitable voltage mode detectors for use with the analyte detection system 10 disclosed herein include: models LIE 302 and 312 by InfraTec of Dresden, Germany; model L2002 by BAE Systems of Rockville, Md.; and model LTS-1 by Dias of Dresden, Germany. Suitable current mode detectors include: InfraTec models LIE 301, 315, 345 and 355; and 2×2 current-mode detectors available from Dias.

In one embodiment, one or both of the detectors 150, 170 may meet the following specifications, when assuming an incident radiation intensity of about $9.26 \times 10^{-4}$ watts (rms) per cm$^2$, at 10 Hz modulation and within a cone angle of about 15 degrees: detector area of 0.040 cm$^2$ (2 mm×2 mm square); detector input of $3.70 \times 10^{-5}$ watts (rms) at 10 Hz; detector sensitivity of 360 volts per watt at 10 Hz; detector output of $1.333 \times 10^{-2}$ volta (rms) at 10 Hz; noise of $8.00 \times 10^{-8}$ volta/sqrtHz at 10 Hz; and signal-to-noise ratios of $1.67 \times 10^5$ rms/sqrtHz and 104.4 dB/sqrtHz; and detectivity of $1.00 \times 10^9$ cm sqrtHz/watt.

In alternative embodiments, the detectors 150, 170 may comprise microphones suitable for operation of the detection system 10 in a photoacoustic mode.

Any of the disclosed embodiments of the analyte detection system 10 may comprise a near-patient testing system. As used herein, "near-patient testing system" is used in its ordinary sense and includes, without limitation, test systems that are configured to be used where the patient is rather than exclusively in a laboratory, e.g., systems that can be used at a patient's home, in a clinic, in a hospital, or even in a mobile environment. Users of near-patient testing systems can include patients, family members of patients, clinicians, nurses, or doctors. A "near-patient testing system" could also include a "point-of-care" system.

The components of any of the embodiments of the analyte detection system 10 may be partially or completely contained in an enclosure or casing (not shown) to prevent stray electromagnetic radiation, such as stray light, from contaminating the energy beam E. Any suitable casing may be used. Similarly, the components of the detection system 10 may be mounted on any suitable frame or chassis (not shown) to maintain their operative alignment as depicted in FIGS. 1-2 and 4. The frame and the casing may be formed together as a single unit, member or collection of members.

Any of the disclosed embodiments of the analyte detection system 10 may in one embodiment be configured to be operated easily by the patient or user. As such, the system 10 is may comprise a portable device. As used herein, "portable" is used in its ordinary sense and means, without limitation, that the system 10 can be easily transported by the patient and used where convenient. For example, the system 10 is advantageously small. In one preferred embodiment, the system 10 is small enough to fit into a purse or backpack. In another embodiment, the system 10 is small enough to fit into a pants pocket. In still another embodiment, the system 10 is small enough to be held in the palm of a hand of the user.

When enclosed in the external casing (not shown), the analyte detection system 10 is advantageously no larger than 5.4 inches long by 3.5 inches wide by 1.5 inches deep. In further embodiments, the enclosed system 10 may be no more than about 80% or 90% of this size. In still further embodiments, the enclosed analyte detection system 10 takes up less than about one-half, or less than about one-tenth the volume of a laboratory-grade Fourier Transform Infrared Spectrometer (FTIR), which typically measures about 2 feet wide by one foot high by one foot deep. Accordingly, in these embodiments the enclosed analyte detection system 10 has a volume of less than about 1750 cubic inches, or less than about 350 cubic inches. In still another embodiment, the analyte detection system 10 measures about 3.5 inches by 2.5 inches by 2.0 inches, and/or has a volume of about 10 cubic inches. Despite its relatively small size as disclosed above, the analyte detection system 10 achieves very good performance in a variety of measures, as detailed below. However, the analyte detection system 10 is not limited to these sizes and can be manufactured to other dimensions.

In one method of operation, the analyte detection system 10 shown in FIG. 2 or 4 measures the concentration of an analyte in the material sample S, in part, by comparing the electromagnetic radiation detected by the sample and reference detectors 150, 170. During operation of the detection system 10, each of the secondary filter(s) 60 is sequentially aligned with the major axis X for a dwell time corresponding to the secondary filter 60. (Of course, where an electronically tunable filter or Fabry-Perot interferometer is used in place of the filter wheel 50, the tunable filter or interferometer is sequentially tuned to each of a set of desired wavelengths or wavelength bands in lieu of the sequential alignment of each of the secondary filters with the major axis X.) The energy source 20 is then operated at (any) modulation frequency, as discussed above, during the dwell time period. The dwell time may be different for each secondary filter 60 (or each wavelength or band to which the tunable filter or interferometer is tuned). In one embodiment of the detection system 10, the dwell time for each secondary filter 60 is less than about 1 second. Use of a dwell time specific to each secondary filter 60 advantageously allows the detection system 10 to operate for a longer period of time at wavelengths where errors can have a greater effect on the computation of the analyte concentration in the material sample S. Correspondingly, the detection system 10 can operate for a shorter period of time at wavelengths where errors have less effect on the computed analyte concentration. The dwell times may otherwise be nonuniform among the filters/wavelengths/bands employed in the detection system.

For each secondary filter 60 selectively aligned with the major axis X, the sample detector 150 detects the portion of the sample beam (Es), at the wavelength or wavelength band corresponding to the secondary filter 60, that is transmitted through the material sample S. The sample detector 150 generates a detection signal corresponding to the detected electromagnetic radiation and passes the signal to the processor 180. Simultaneously, the reference detector 170 detects the reference beam (Er) transmitted at the wavelength or wavelength band corresponding to the secondary filter 60. The reference detector 170 generates a detection signal corresponding to the detected electromagnetic radiation and passes the signal to the processor 180. Based on the signals passed to it by the detectors 150, 170, the processor 180 computes the concentration of the analyte(s) of interest in the sample S, and/or the absorbance/transmittance characteristics of the sample S at one or more wavelengths or wavelength bands employed to analyze the sample. The processor 180 computes the concentration(s), absorbance(s), transmittance(s), etc. by executing a data processing algorithm or program instructions residing within the memory 185 accessible by the processor 180.

The signal generated by the reference detector may be used to monitor fluctuations in the intensity of the energy beam emitted by the source 20, which fluctuations often arise due to drift effects, aging, wear or other imperfections in the source itself. This enables the processor 180 to identify changes in intensity of the sample beam (Es) that are attributable to changes in the emission intensity of the source 20, and not to the composition of the sample S. By so doing, a potential source of error in computations of concentration, absorbance, etc. is minimized or eliminated.

In one embodiment, the detection system 10 computes an analyte concentration reading by first measuring the electromagnetic radiation detected by the detectors 150, 170 at each center wavelength, or wavelength band, without the sample element 120 present on the major axis X (this is known as an "air" reading). Second, the system 10 measures the electromagnetic radiation detected by the detectors 150, 170 for each center wavelength, or wavelength band, with the sample element 120 present on the major axis X, but without the material sample S (i.e., a "dry" reading). Third, the system 10 measures the electromagnetic radiation detected by the detectors 150, 170 with an opaque element or mask (such as a secondary filter 60 which is substantially opaque in the wavelength(s) of interest) disposed on the major axis X between the source 20 and beam splitter 100, and/or with the source 20 switched off (i.e., a "dark" reading). Fourth, the system 10 measures the electromagnetic radiation detected by the detectors 150, 170 for each center wavelength, or wavelength band, with the material sample S present in the sample element 120, and the sample element 120 and sample S in position on the major axis X (i.e., a "wet" reading). Finally, the processor 10 computes the concentration(s), absorbance(s) and/or transmittances relating to the sample S based on these compiled readings.

Figure 7:
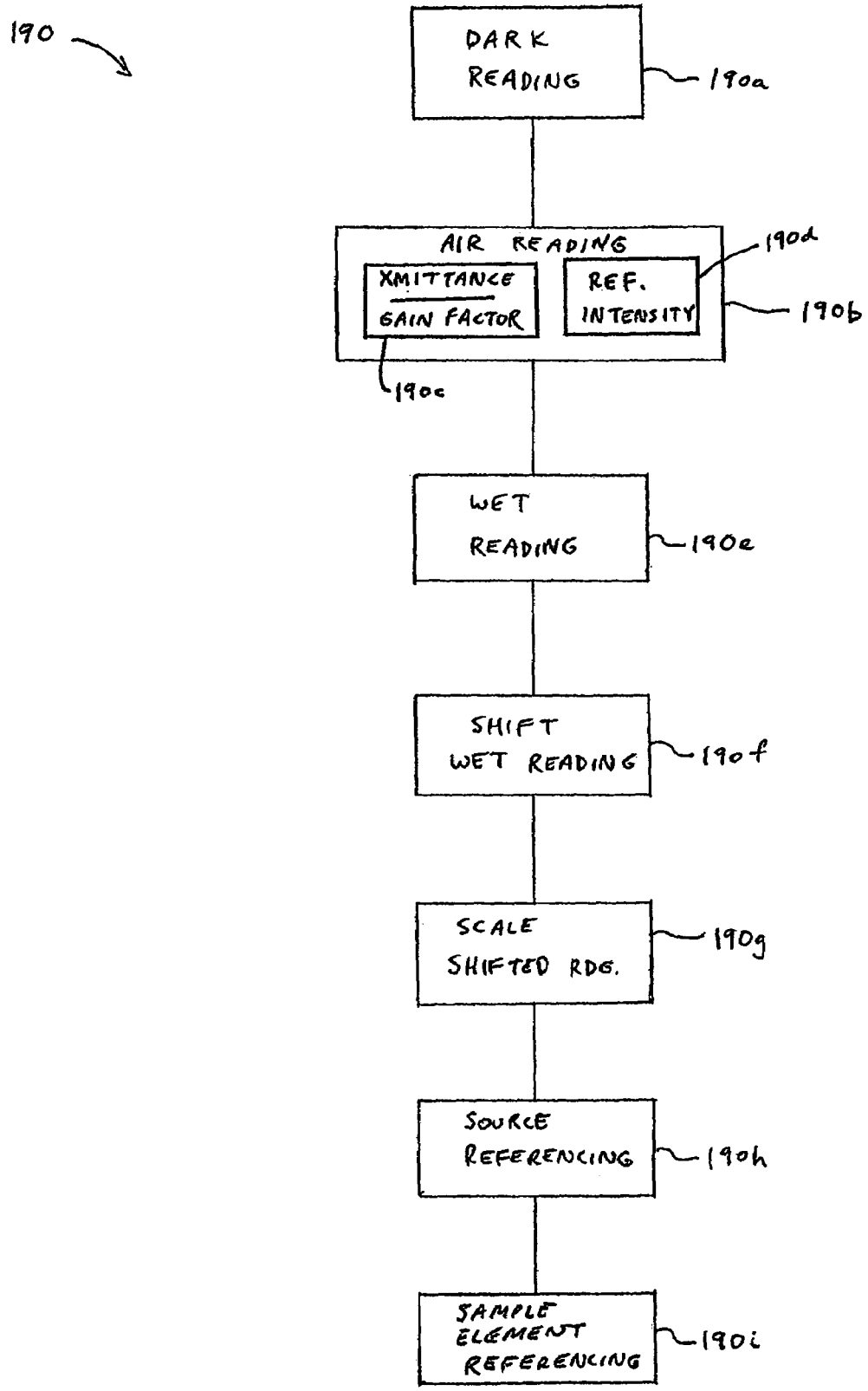
FIG. 7 is a flowchart of one embodiment of a method of operation of various embodiments of the analyte detection system.

FIG. 7 depicts a further embodiment of a method 190 of operating either of the analyte detection systems 10 depicted in FIG. 2 or FIG. 4 (or, alternatively, any suitable detection system). In the following description, the method 190 is conducted in the transmittance domain; however, it may alternatively be performed in the absorbance domain with the relevant measures adjusted accordingly for working with absorbance measures rather than transmittance measures.

In an operational block 190a, a "dark" reading is taken as discussed above, wherein the processor 180 computes a dark transmittance reading TD, which is stored in memory. Next, an "air" reading is taken, as discussed above, in an operational block 190b. This operation may comprise computing and storing an air transmittance reading TA, and a gain factor GF which equals 100%/TA (see operational block 190c), as well as a simultaneous air reference intensity RIA (operational block 190d), based on the output of the reference detector 170 during the air reading. In one embodiment, any or all of the air transmittance reading TA, gain factor GF and air reference intensity RIA are computed at each of the wavelengths or wavelength bands of interest, yielding, for example, $TA_{\lambda 1}$, $TA_{\lambda 2}$, . . . $TA_{\lambda n}$; $GF_{\lambda 1}$, $GF_{\lambda 2}$, . . . $GF_{\lambda n}$; etc.

In operational block 190e, a "wet" reading is taken as described above, with the sample element and sample S therein positioned on the major axis X. The wet reading yields a series of wavelength-specific transmittance values $T_{\lambda 1}$, $T_{\lambda 2}$, . . . $T_{\lambda n}$ in each of the wavelengths or bands of interest, which values are stored in memory, along with simultaneously-recorded corresponding wet reference intensities $RIW_{\lambda 1}$, $RIW_{\lambda 2}$, . . . $RIW_{\lambda n}$ which arise from the output of the reference detector 170 at each wavelength/band of interest while the wet reading is taken. The wet reading is then shifted (see block 190f) by subtracting the dark transmittance reading(s) from each of the wavelength-specific transmittance values $T_{\lambda 1}$, $T_{\lambda 2}$, . . . $T_{\lambda n}$, yielding shifted transmittance values $TS_{\lambda 1}$, $TS_{\lambda 2}$, . . . $TS_{\lambda n}$. In block 190g, the shifted transmittance values are scaled by multiplying each of the values $TS_{\lambda 1}$, $TS_{\lambda 2}$, . . . $TS_{\lambda n}$, by the previously-computed gain factor (s) GF. Where wavelength-specific gain factors $GF_{\lambda 1}$, $GF_{\lambda 2}$, . . . $GF_{\lambda n}$ have been computed, each shifted transmittance value $TS_{\lambda i}$, is multiplied by its corresponding gain factor $GF_{\lambda i}$. Either option yields shifted, scaled transmittance values $TSS_{\lambda 1}$, $TSS_{\lambda 2}$, . . . $TSS_{\lambda n}$.

In operational block 190h, each of the shifted, scaled transmittance values $TSS_{\lambda 1}$, $TSS_{\lambda 2}$, . . . $TSS_{\lambda n}$ is source-referenced. First, a series of reference factors $RF_{\lambda 1}$, $RF_{\lambda 2}$, . . . $RF_{\lambda n}$ are computed by dividing the air reference intensity RIA by each of the wet reference intensities $RIW_{\lambda 1}$, $RIW_{\lambda 2}$, . . . $RIW_{\lambda n}$. Where a series of air reference intensities $RIA_{\lambda 1}$, $RIA_{\lambda 2}$, . . . $RIA_{\lambda n}$ have been compiled, each air reference intensity $RIA_{\lambda i}$ is divided by its corresponding wet reference intensity $RIW_{\lambda i}$ to generate the reference factors $RF_{\lambda 1}$, $RF_{\lambda 2}$, . . . $RF_{\lambda n}$. Each of the shifted, scaled transmittance values $TSS_{\lambda 1}$, $TSS_{\lambda 2}$, . . . $TSS_{\lambda n}$ is source-referenced by multiplying it by the corresponding reference factor $RF_{\lambda 1}$, $RF_{\lambda 2}$, . . . $RF_{\lambda n}$ to generate shifted, scaled, source-referenced transmittance values $TSSR_{\lambda 1}$, $TSSR_{\lambda 2}$, . . . $TSSR_{\lambda n}$.

Each of the shifted, scaled, source-referenced transmittance values $TSSR_{\lambda 1}$, $TSSR_{\lambda 2}$, . . . $TSSR_{\lambda n}$ is sample-element referenced in operational block 190i, to yield final transmittance values $TF_{\lambda 1}$, $TF_{\lambda 2}$, . . . $TF_{\lambda n}$. Any of the sample-element referencing methods disclosed herein may be employed. While the sample-element referencing operation 190i is depicted at the end of the illustrated method 190, this referencing 190i may in practice comprise a number of sub-operations that are intermingled with the other operations of the method 190, as will become apparent from the discussion herein of the various sample-element referencing methods. Regardless of the nature of the sample-element referencing operation, the final transmittance values $TF_{\lambda 1}$, $TF_{\lambda 2}$, . . . $TF_{\lambda n}$ may then be employed to compute the concentration of the analyte(s) of interest in the sample S.

In further embodiments, any suitable variation of the method 190 may be employed. Any one or combination of the operations 190a-190i may be omitted, depending on the desired level of measurement precision. For example, the dark reading 190a and subsequent shift 190f may be omitted. Instead of or in addition to omission of these operations 190a, 190f, the air reading 190b may be omitted, in whole or in part. Where measurement/computation of the air transmittance reading TA and gain factor GF (block 190c) are omitted, the scaling operation 190g may also be omitted;

likewise, where measurement/computation of the air reference intensity RIA (block 190d) is omitted, the source referencing operation 190h may also be omitted. Finally, instead or in addition to the foregoing omissions, the sample element referencing operation 190i may be omitted.

In any variation of the method 190, the operations may be performed in any suitable sequence, and the method 190 is by no means limited to the sequence depicted in FIG. 7 and described above. Although, in the foregoing discussion of the method 190, a number of measurements and computations are performed in the transmittance domain, in further embodiments any or all of these measurements and computations may be performed in the absorbance or optical density domain. Under the foregoing discussion, the method 190 includes "live" computation/measurement of the dark transmittance reading TD, air transmittance reading TA, gain factor GF and air reference intensity RIA, during a measurement run of the detection system 10. In further embodiments of the method 190, any or all of these values may be predetermined or computed in a previous measurement, then stored in memory for use in a number of subsequent measurement runs, during which the value in question is recalled from memory for use as described above, rather than measured/computed anew.

In still further embodiments, any of the computational algorithms or methods discussed below may be employed to compute the concentration of the analyte(s) of interest in the sample S from (any) final transmittance values $TF_{\lambda 1}$, $TF_{\lambda 2}$, ... $TF_{\lambda n}$ output by any of the embodiments of the method 190 discussed herein. Any of the disclosed embodiments of the method 190 may reside as program instructions in the memory 185 so as to be accessible for execution by the processor 180 of the analyte detection system 10.

In one embodiment, the processor 180 is configured to communicate the analyte concentration results and/or other information to a display controller (not shown), which operates a display (not shown), such as an LCD display, to present the information to the user. In one embodiment, the processor 180 can communicate to the display controller only the concentration of glucose in the material sample S. In another embodiment, the processor 180 can communicate to the display controller the concentration of ketone in addition to the concentration of glucose in the material sample S. In still another embodiment, the processor 180 can communicate to the display controller the concentration of multiple analytes in the material sample S. In yet another embodiment, the display outputs the glucose concentration with a resolution of 1 mg/dL.

Additional capabilities of various embodiments of the analyte detection system 10, and other related information, may be found in U.S. patent application Ser. No. 10/826, 004, filed on even date herewith, titled SYSTEM AND METHOD FOR MANAGING A CHRONIC MEDICAL CONDITION. The entire contents of this patent application is hereby incorporated herein in its entirety by this reference and made a part of this specification.

II. SAMPLE ELEMENT

In view of the foregoing disclosure of certain embodiments of the analyte detection system 10, the following section discusses various embodiments of a cuvette or sample element for use with the analyte detection system 10. As used herein, "sample element" is a broad term and is used in its ordinary sense and includes, without limitation, structures that have a sample chamber and at least one sample chamber wall, but more generally includes any of a number of structures that can hold, support or contain a material sample and that allow electromagnetic radiation to pass through a sample held, supported or contained thereby; e.g., a cuvette, test strip, etc.

Figure 8:
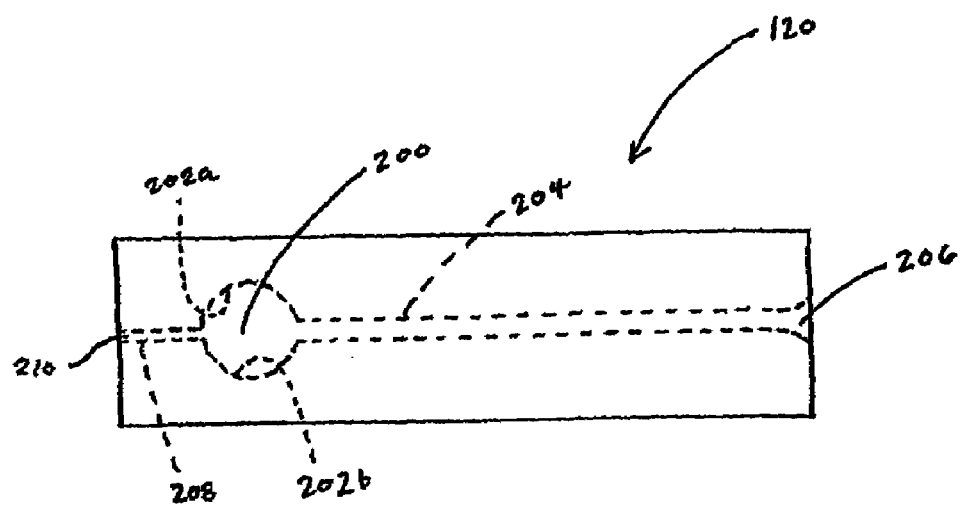
FIG. 8 is a plan view of one embodiment of a sample element suitable for use in combination with various embodiments of the analyte detection system.
Figure 9:
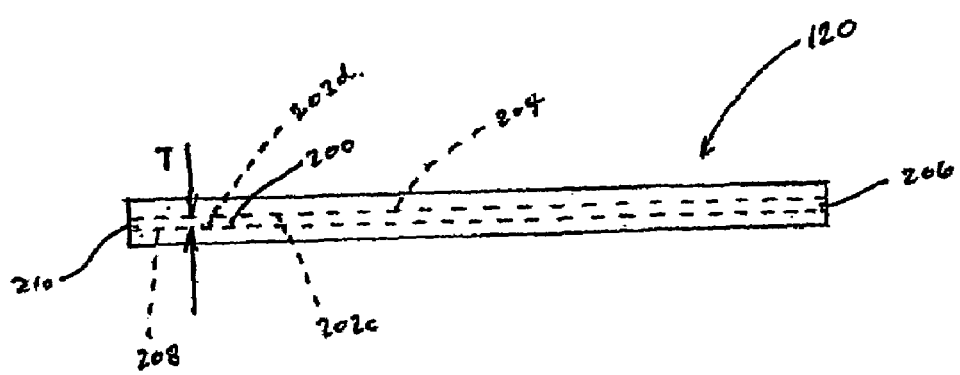
FIG. 9 is a side elevation view of the sample element illustrated in FIG. 8.

FIGS. 8 and 9 depict a cuvette or sample element 120 for use with any of the various embodiments of the analyte detection system 10 disclosed herein. Alternatively, the sample element 120 may be employed with any suitable analyte detection system. The sample element 120 comprises a sample chamber 200 defined by sample chamber walls 202a-d. The sample chamber 200 is configured to hold a material sample which may be drawn from a patient, for analysis by the detection system with which the sample element 120 is employed. Alternatively, the sample chamber 200 may be employed to hold other organic or inorganic materials for such analysis.

In the embodiment illustrated in FIGS. 8-9, the sample chamber 200 is defined by first and second lateral chamber walls 202a, 202b and upper and lower chamber walls 202c, 202d; however, any suitable number and configuration of chamber walls may be employed. At least one of the upper and lower chamber walls 202c, 202d is formed from a material which is sufficiently transmissive of the wavelength(s) of electromagnetic radiation that are employed by the analyte detection system 10 (or any other system with which the sample element is to be used). A chamber wall which is so transmissive may thus be termed a "window;" in one embodiment, the upper and lower chamber walls 202c, 202d comprise first and second windows so as to permit the relevant wavelength(s) of electromagnetic radiation to pass through the sample chamber 200. In another embodiment, these first and second windows are similar to the first and second windows 122, 124 discussed above. In yet another embodiment, only one of the upper and lower chamber walls 202c, 202d comprises a window; in such an embodiment, the other of the upper and lower chamber walls may comprise a reflective surface configured to back-reflect any electromagnetic energy emitted into the sample chamber 200 by the analyte detection system with which the sample element 120 is employed. Accordingly, this embodiment is well suited for used with an analyte detection system in which a source and a detector of electromagnetic energy are located on the same side as the sample element.

In various embodiments, the material that makes up the window(s) of the sample element 120 is completely transmissive, i.e., it does not absorb any of the electromagnetic radiation from the source 20 and first and second filters 40, 60 that is incident upon it. In another embodiment, the material of the window(s) has some absorption in the electromagnetic range of interest, but its absorption is negligible. In yet another embodiment, the absorption of the material of the window(s) is not negligible, but it is known and stable for a relatively long period of time. In another embodiment, the absorption of the window(s) is stable for only a relatively short period of time, but the analyte detection system 10 is configured to observe the absorption of the material and eliminate it from the analyte measurement before the material properties can change measurably. Materials suitable for forming the window(s) of the sample element 120 include barium fluoride, silicon, polypropylene, polyethylene, or any polymer with suitable transmissivity (i.e., transmittance per unit thickness) in the relevant wavelength(s). Where the window(s) are formed from a polymer, the selected polymer can be isotactic, atactic or syndiotactic in structure, so as to enhance the flow of the sample between the window(s). One type of polyethylene suitable for constructing the sample element 120 is type 220, as extruded, available from KUBE Ltd. of Staefa, Switzerland.

In one embodiment, the sample element 120 is configured to allow sufficient transmission of electromagnetic energy having a wavelength of between about 4 µm and about 10.5 µm through the window(s) thereof. However, the sample element 120 can be configured to allow transmission of wavelengths in any spectral range emitted by the energy source 20. In another embodiment, the sample element 120 is configured to receive an optical power of more than about 1.0 MW/cm$^2$ from the sample beam (Es) incident thereon for any electromagnetic radiation wavelength transmitted through-the secondary filter(s) 60. In still another embodiment, the sample element 120 is configured to allow transmission of about 75% of the electromagnetic energy incident upon the sample chamber 200 therethrough. Preferably, the sample chamber 200 of the sample element 120 is configured to allow a sample beam (Es) advancing toward the material sample S within a cone angle of 45 degrees from the major axis X (see FIGS. 1, 2) to pass therethrough.

In the embodiment illustrated in FIGS. 8-9, the sample element further comprises a supply passage 204 extending from the sample chamber 200 to a supply opening 206 and a vent passage 208 extending from the sample chamber 200 to a vent opening 210. While the vent opening 210 is shown at one end of the sample element 120, in other embodiments the vent opening 210 may be positioned on either side of the sample element 120, so long as it is in fluid communication with the vent passage 208.

In operation, the supply opening 206 of the sample element 120 is placed in contact with the material sample S, such as a fluid flowing from a wound on a patient. The fluid is then transported through the sample supply passage 204 and into the sample chamber 200 via capillary action. The vent passage 208 and vent opening 210 improve the sample transport by preventing the buildup of air pressure within the sample element and allowing the sample to displace the air as the sample flows to the sample chamber 200.

Where the upper and lower chamber walls 202c, 202d comprise windows, the distance T (measured along an axis substantially orthogonal to the sample chamber 200 and/or windows 202a, 202b, or, alternatively, measured along an axis of an energy beam (such as but not limited to the energy beam E discussed above) passed through the sample chamber 200) between them comprises an optical pathlength (see FIG. 9). In various embodiments, the pathlength is between about 1 µm and about 300 µm, between about 1 µm and about 100 µm, between about 25 µm and about 40 µm, between about 10 µm and about 40 µm, between about 25 µm and about 60 µm, or between about 30 µm and about 50 µm. In still another embodiment, the optical pathlength is about 25 µm. In some instances, it is desirable to hold the pathlength T to within about plus or minus 1 µm from any pathlength specified by the analyte detection system with which the sample element 120 is to be employed. Likewise, it may be desirable to orient the walls 202c, 202d with respect to each other within plus or minus 1 µm of parallel, and/or to maintain each of the walls 202c, 202d to within plus or minus 1 µm of planar (flat), depending on the analyte detection system with which the sample element 120 is to be used.

In one embodiment, the transverse size of the sample chamber 200 (i.e., the size defined by the lateral chamber walls 202a, 202b) is about equal to the size of the active surface of the sample detector 150. Accordingly, in a further embodiment the sample chamber 200 is round with a diameter of about 4 mm.

The sample element 120 shown in FIGS. 8-9 has, in one embodiment, sizes and dimensions specified as follows. The supply passage 204 preferably has a length of about 17.7 mm, a width of about 0.7 mm, and a height equal to the pathlength T. Additionally, the supply opening 206 is preferably about 3 mm wide and smoothly transitions to the width of the sample supply passage 204. The sample element 120 is about 0.375 inches wide and about one inch long with an overall thickness of between about 1.025 mm and about 1.140 mm. The vent passage 208 preferably has a length of about 1.8 mm to 2 mm and a width of about 3.8 mm to 4 mm, with a thickness substantially equal to the pathlength between the walls 202c, 202d. The vent aperture 210 is of substantially the same height and width as the vent passage 208. Of course, other dimensions may be employed in other embodiments while still achieving the advantages of the sample element 120.

The sample element 120 is preferably sized to receive a material sample S having a volume less than or equal to about 3 µL (or less than or equal to about 2 µL, or less than or equal to about 1 µL) and more preferably a material sample S having a volume less than or equal to about 0.85 µL. Of course, the volume of the sample element 120, the volume of the sample chamber 200, etc. can vary, depending on many variables, such as the size and sensitivity of the sample detector 150, the intensity of the radiation emitted by the energy source 20, the expected flow properties of the sample, and whether flow enhancers are incorporated into the sample element 120. The transport of fluid to the sample chamber 200 is achieved preferably through capillary action, but may also be achieved through wicking, or a combination of wicking and capillary action.

Figure 10:
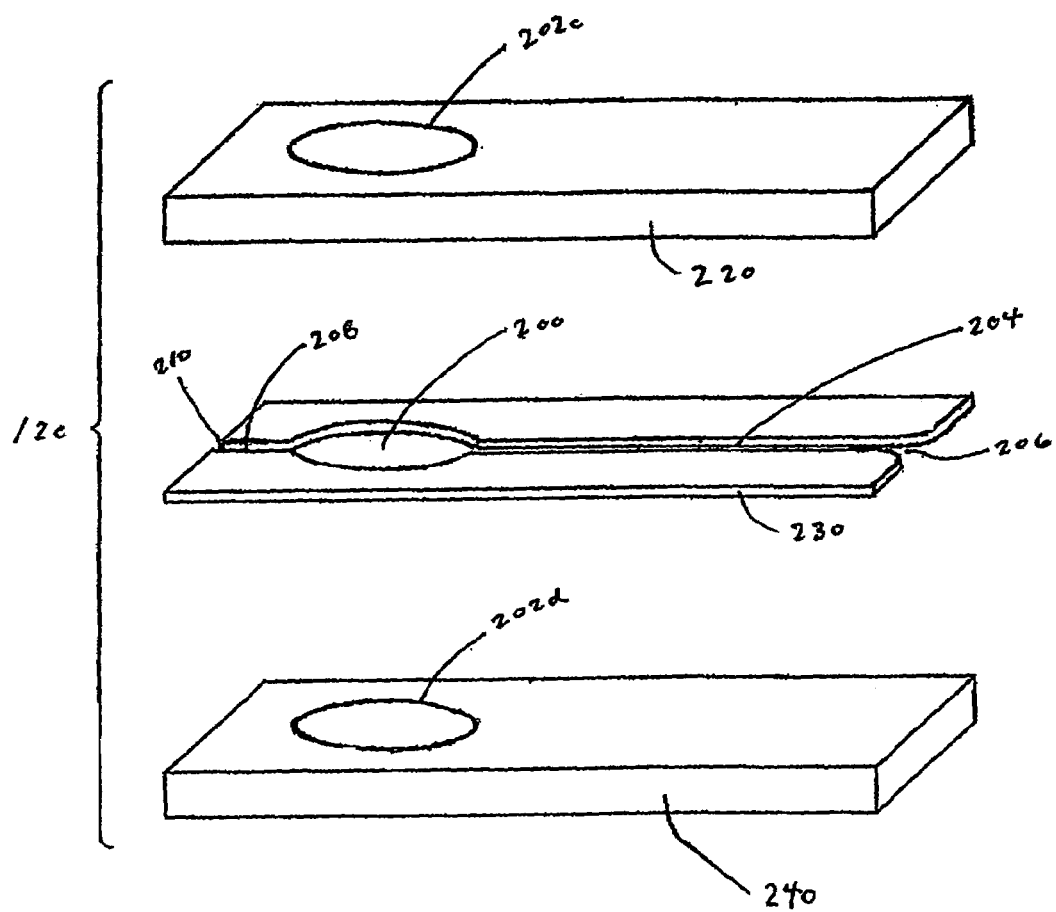
FIG. 10 is an exploded view of the sample element illustrated in FIG. 8.

FIG. 10 depicts one approach to constructing the sample element 120. In this approach, the sample element 120 comprises a first layer 220, a second layer 230, and a third layer 240. The second layer 230 is preferably positioned between the first layer 220 and the third layer 240. The first layer 220 forms the upper chamber wall 202c, and the third layer 240 forms the lower chamber wall 202d. Where either of the chamber walls 202c, 202d comprises a window, the window(s)/wall(s) 202c/202d in question may be formed from a different material as is employed to form the balance of the layer(s) 220/240 in which the wall(s) are located. Alternatively, the entirety of the layer(s) 220/240 may be formed of the material selected to form the window(s)/wall(s) 202c, 202d. In this case, the window(s)/wall(s) 202c, 202d are integrally formed with the layer(s) 220, 240 and simply comprise the regions of the respective layer(s) 220, 240 which overlie the sample chamber 200.

With further reference to FIG. 10, the second layer 230 may be formed entirely of an adhesive that joins the first and third layers 220, 240. In other embodiments, the second layer 230 may be formed from similar materials as the first and third layers, or any other suitable material. The second layer 230 may also be formed as a carrier with an adhesive deposited on both sides thereof. The second layer 230 includes voids which at least partially form the sample chamber 200, sample supply passage 204, supply opening 206, vent passage 208, and vent opening 210. The thickness of the second layer 230 can be the same as any of the pathlengths disclosed above as suitable for the sample element 120. The first and third layers can be formed from any of the materials disclosed above as suitable for forming the window(s) of the sample element 120.

The sample chamber 200 preferably comprises a reagent-less chamber. In other words, the internal volume of the sample chamber 200 and/or the wall(s) 202 defining the chamber 200 are preferably inert with respect to the sample to be drawn into the chamber for analysis. As used herein, "inert" is a broad term and is used in its ordinary sense and includes, without limitation, substances which will not react with the sample in a manner which will significantly affect any measurement made of the concentration of analyte(s) in the sample with the analyte detection system 10 or any other suitable system, for a sufficient time (e.g., about 1-30 minutes) following entry of the sample into the chamber 200, to permit measurement of the concentration of such analyte(s). Alternatively, the sample chamber 200 may contain one or more reagents to facilitate use of the sample element in sample assay techniques which involve reaction of the sample with a reagent.

In one embodiment, the sample element may be configured to separate plasma from a whole-blood or other similar sample, via employment of an appropriate filter or membrane, between the entry point of the sample into the sample element, and the sample chamber(s). In a sample element so configured, the plasma flows downstream from the filter/membrane, to the sample chamber(s). The balance of the sample (e.g., blood cells) remains at the filter/membrane. In various embodiments, the filter/membrane may be constructed from microporous polyethylene or microporous polytetrafluoroethylene. In another embodiment, the filter/membrane may be constructed from BTS-SP media available from Pall Corporation of East Hills, N.Y.

Additional information on sample elements, methods of use thereof, and related technologies may be found in U.S. patent application Ser. No. 10/825,223, filed on even date herewith, titled SAMPLE ELEMENT WITH BARRIER MATERIAL. The entire contents of this patent application is hereby incorporated herein in its entirety by this reference and made a part of this specification.

III. SAMPLE ELEMENT REFERENCING

In this section, there are disclosed a number of methods for sample-element referencing, which generally comprises compensating for the effects of the sample element on the measurement of analyte concentration. Any one or combination of the methods disclosed in this section may reside as program instructions in the memory 185 so as to be accessible for execution by the processor 180 of the analyte detection system 10. In addition, any one or combination of the methods disclosed in this section may be employed as the sample-element referencing operation 190i of various embodiments of the method 190 depicted in FIG. 7 and discussed above.

Where employed as the sample-element referencing operation 190i of the method 190 (or where otherwise employed), any of the methods disclosed in this section may be performed in a wavelength-specific fashion, i.e. by computing a sample-element referenced transmittance, absorbance or optical density at each wavelength/band analyzed by the analyte detection system in question.

As discussed above, materials having some electromagnetic radiation absorption in the spectral range employed by the analyte detection system 10 can be used to construct some or all of the sample element 120. The accuracy of an analyte detection system, such as the system 10 disclosed herein, may be improved by accounting for any scattering or absorption phenomena attributable to the sample element when computing the concentration of the analyte(s) of interest. Such scattering or absorption due to imperfect transmission properties of the materials of the sample element may be overcome by determining at least one reference level of absorbance of the sample element and then removing the reference level from a subsequent measurement performed with the sample element. Devices and methods for overcoming imperfect transmission properties of materials employed in sample elements are now discussed with reference to FIGS. 11-21.

In one embodiment, an empty, unused sample element, such as the sample element 120, can be referenced by determining the reference level of absorbance/transmittance (and scattering) of the sample element 120. In certain embodiments, the method comprises positioning the sample chamber 200 of the sample element 120 within the sample beam Es which passes through the windows 202c, 202d. The analyte detection system 10 then determines a reference level of absorbance or transmittance by the windows 202c, 202d. A sample material is then drawn into the sample chamber 200. The sample beam Es is then passed through the windows 202c, 202d of the sample chamber 200 as well as the sample itself. The analyte detection system 10 determines an analytical level of absorbance or transmittance by the combination of the sample and the windows 202c, 202d. Upon determining the reference and analytical levels of absorbance or transmittance, the analyte detection system 10 can account for absorption/transmission effects of the material comprising the windows 202c, 202d when determining the concentration of the analyte(s) of interest. Analyzing the reference and analytical levels of absorbance or transmittance (in other words, accounting for the absorbance/transmittance effects of the material comprising the windows 202c, 202d) can comprise calculating a difference in optical density between the two. Alternatively, analyzing the levels can comprise calculating a ratio of the analytical level of transmission to the reference level of transmission.

The difference-calculation alternative is employed where the sample element referencing method is performed in the absorbance or optical density domain, and the ratio-calculation alternative is employed where the method is performed in the transmittance domain. The resulting data set (typically, an absorbance or transmittance spectrum assembled from sample-element referenced absorbance/transmittance measurements taken at each wavelength/band analyzed by the detection system 10) can then be analyzed to compute the concentration of the analyte(s) of interest in the sample. This concentration analysis may be performed by employing any suitable method, including but not limited to any of the various computational algorithms discussed in further detail in Section IV below. For example, any of the methods disclosed below for determining analyte concentration(s) independent of the optical pathlength through the sample, may be employed.

Figure 11:
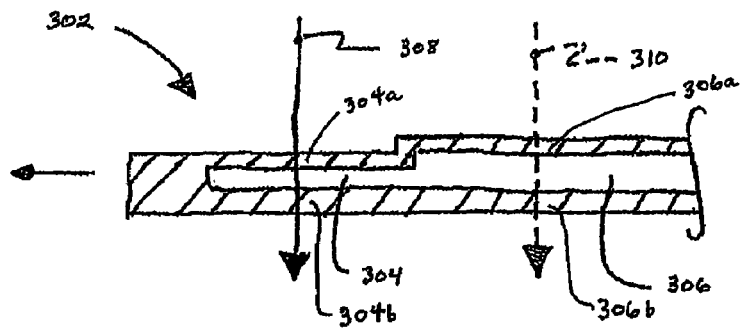
FIG. 11 is a cross-sectional view of one embodiment of a sample element configured for analysis of a sample at two separate pathlengths.

FIG. 11 is a schematic illustration of a sample element 302 configured to be referenced by an analyte detection system, such as but not limited to the analyte detection system 10 disclosed above, in accordance with methods described in detail below. Except as further described herein, the sample element 302 may in one embodiment be similar to any of the embodiments of the sample element 120 discussed above. As depicted in FIG. 11, the sample element 302 comprises a referencing chamber 304 situated between first and second referencing windows 304a, 304b; and a sample chamber 306 situated between first and second sample windows 306a, 306b. In one embodiment, the separation (i.e., pathlength) between the inner surfaces of the referencing windows 304a, 304b is different than the separation (i.e., pathlength) between the inner surfaces of the sample windows 306a, 306b. In certain embodiments, the pathlength of the referencing chamber 304 is smaller than that of the sample chamber 306, while in other embodiments the pathlength of the sample chamber 306 is smaller than that of the referencing chamber 304. In still other embodiments, the pathlength of the referencing chamber 304 is substantially zero. In one embodiment, one of the chambers 304, 306 has a pathlength of about 10 microns, and the other of the chambers has a pathlength of about 30 microns.

As illustrated in FIG. 11, the first referencing window 304a and first sample window 306a are preferably of substantially similar thickness, and the second referencing window 304b and second sample window 306b are preferably of substantially similar thickness as well. In one embodiment, all of the windows 304a, 304b, 306a, 306b are of substantially similar thickness. However, in other embodiments these thicknesses may differ among the windows.

In one embodiment, one or more of the outer surfaces of one or more of the windows 304a, 304b, 306a, 306b is textured. This may be done by, for example, sanding the surface(s) in question, and/or molding or otherwise constructing them to have a relatively non-smooth surface finish. Depending on the materials employed to construct the sample element, texturing may improve the optical qualities of the sample element by reducing fringing. This texturing may be employed with any of the embodiments of the sample element disclosed herein by, for example, texturing one or both of the outer surfaces of the windows 202c, 202d of the sample element 120.

In one method of operation, the sample element 302 is coupled with an analyte detection system 10 which utilizes a single beam of electromagnetic radiation for referencing the sample element 302 and for measuring the concentration of an analyte in the sample. A sample is drawn into the referencing chamber 304 (in those embodiments where the referencing chamber is of sufficient pathlength or volume) and into the sample chamber 306. The sample element 302 is placed in a reference position within the analyte detection system 10 wherein the referencing chamber 304 and referencing windows 304a, 304b reside within an optical path of a reference beam 308 of electromagnetic radiation. The reference beam 308 is then passed through the referencing chamber 304 (and, where applicable, that portion of the sample contained therein), and referencing windows 304a, 304b. The analyte detection system 10 determines a reference level of absorbance or transmittance of the reference beam 308 due to absorbance or transmittance by the combination of (any) sample within the referencing chamber 304 and the referencing windows 304a, 304b. The sample element 302 is placed into an analytical position wherein the sample chamber 306 and sample windows 306a, 306b reside within the optical path of an analytical beam 310. The analytical beam 310 is then passed through the sample-filled sample chamber 306 and sample windows 306a, 306b. The analyte detection system 10 determines an analytical level of absorbance or transmittance of the analytical beam 310 due to absorbance or transmittance by the combination of the sample within the sample chamber 306 and the sample windows 306a, 306b. In one embodiment, reference and analytical levels of absorbance or transmittance are measured at each wavelength/band analyzed by the analyte detection system 10.

Upon determining the reference and analytical levels of absorbance or transmittance, the analyte detection system 10 can account for absorbance or transmittance effects of the material comprising the sample element 302 when determining the concentration of the analyte(s) of interest in the sample. Analyzing the reference and analytical levels of absorbance or transmittance (in other words, accounting for the absorbance or transmittance effects of the material comprising the sample element 302) can comprise calculating a difference between the two. Alternatively, analyzing the levels can comprise calculating a ratio of the analytical level to the reference level.

The difference-calculation alternative is employed where the sample element referencing method is performed in the absorbance or optical density domain, and the ratio-calculation alternative is employed where the method is performed in the transmittance domain. Where reference and analytical levels of absorbance or transmittance have been measured in each of a series of wavelengths/bands, the difference calculation or ratio calculation is performed on the (reference level, analytical level) pair measured at each wavelength/band in the series.

The resulting data set (for example, an absorbance or transmittance spectrum assembled from sample-element referenced absorbance/transmittance measurements taken at each wavelength/band analyzed by the detection system 10) can then be analyzed to compute the concentration of the analyte(s) of interest in the sample. This concentration analysis may be performed by employing any suitable method, including but not limited to any of the various computational algorithms discussed in further detail in Section IV below. For example, any of the methods disclosed below for determining analyte concentration(s) independent of the optical pathlength through the sample, may be employed.

Where significant differences arise between the thicknesses of the first referencing window 304a and first sample window 306a, or between the thicknesses of the first referencing window 304a and first sample window 306a, the absorbance/transmittance data output by the ratio-calculation/difference calculation procedure may "include" some of the absorbance/transmittance aspects of the window material. Accordingly, where desired various embodiments of the methods disclosed in Section IV below for removing non-analyte contributions from absorption data, may be employed when analyzing the absorbance/transmittance data to determine analyte concentration.

Figure 12:
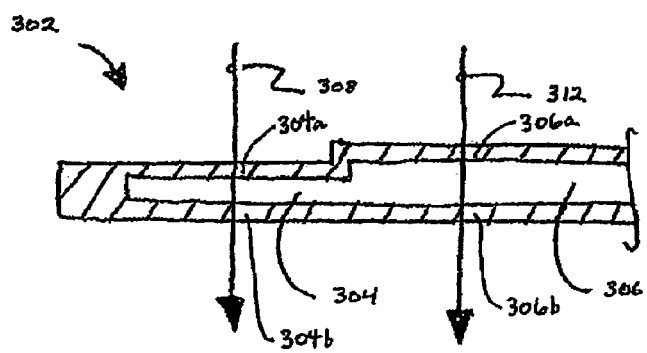
FIG. 12 is a cross-sectional view of the sample element of FIG. 11, as employed in an alternative method of analysis.

In another method of operation depicted in FIG. 12, the sample element 302 is coupled with an analyte detection system 10 which utilizes separate beams of electromagnetic radiation for referencing the sample element 302 and for measuring the concentration of an analyte in the sample. A sample is drawn into the referencing chamber 304 (in those embodiments where the referencing chamber is of sufficient volume) and into the sample chamber 306 of the sample element 302. As depicted in FIG. 12, the sample element 302 is placed within the analyte detection system 10 so that the referencing chamber 304 and referencing windows 304a, 304b reside within the path of the reference beam 308 and so that the sample chamber 306 and sample windows 306a, 306b reside within the path of an analytical beam 312. The reference beam 308 passes through the referencing chamber 304 (and, where applicable, any portion of the sample contained therein), and referencing windows 304a, 304b, and the analytical beam 312 passes through the sample chamber 306, that portion of the sample contained therein, and the sample windows 306a, 306b. The analyte detection system 10 determines a reference level of absorbance or transmittance of the reference beam 308 due to absorbance or transmittance by the combination of (any) sample within the referencing chamber 304 and the material comprising the reference windows 304a, 304b, and determines an analytical level of absorbance or transmittance of the analytical beam 312 due to absorbance or transmittance by the combination of the sample and the material comprising the sample windows 306a, 306b.

Upon determining the reference and analytical levels of absorbance or transmittance, the analyte detection system 10 can account for absorbance or transmittance effects of the material comprising the sample element 302 when determining the concentration of the analyte(s) of interest in the sample. Analyzing the reference and analytical levels of absorbance or transmittance (in other words, accounting for the absorbance or transmittance effects of the material comprising the sample element 302) can comprise calculating a difference between the two. Alternatively, analyzing the levels can comprise calculating a ratio of the analytical level to the reference level.

The difference-calculation alternative is employed where the sample element referencing method is performed in the absorbance or optical density domain, and the ratio-calculation alternative is employed where the method is performed in the transmittance domain. Where reference and analytical levels of absorbance or transmittance have been measured in each of a series of wavelengths/bands, the difference calculation or ratio calculation is performed on the (reference level, analytical level) pair measured at each wavelength/band in the series.

The resulting data set (for example, an absorbance or transmittance spectrum assembled from sample-element referenced absorbance/transmittance measurements taken at each wavelength/band analyzed by the detection system 10) can then be analyzed to compute the concentration of the analyte(s) of interest in the sample. This concentration analysis may be performed by employing any suitable method, including but not limited to any of the various computational algorithms discussed in further detail in Section IV below. For example, any of the methods disclosed below for determining analyte concentration(s) independent of the optical pathlength through the sample, may be employed.

Where significant differences arise between the thicknesses of the first referencing window 304a and first sample window 306a, or between the thicknesses of the first referencing window 304a and first sample window 306a, the absorbance/transmittance data output by the ratio-calculation/difference calculation procedure may "include" some of the absorbance/transmittance aspects of the window material. Accordingly, where desired various embodiments of the methods disclosed in Section IV below for removing non-analyte contributions from absorption data, may be employed when analyzing the absorbance/transmittance data to determine analyte concentration.

In certain embodiments, a sample element may be referenced so as to overcome transmission properties of the materials comprising the sample element by drawing a sample into the sample element and then compressing a sample chamber of the sample element, thereby changing the separation (i.e., pathlength) between the inner surfaces of the sample chamber by a predetermined amount. Such embodiments use a deformable sample element and controllably change the pathlength of the beam of electromagnetic radiation passing through the material of, and/or the sample within, the sample chamber. The change in pathlength facilitates distinguishing the absorbance or transmittance by the material of the sample element from the absorbance or transmittance by the sample within the sample chamber, by using any of the analysis methods (i.e., difference-calculation, ratio-calculation) disclosed above.

Figure 13:
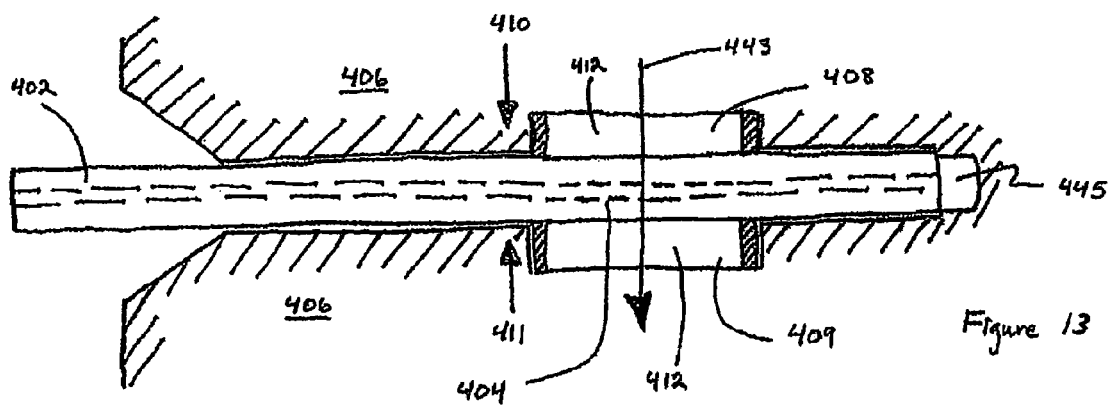
FIG. 13 is a cross-sectional view of one embodiment of an analyte detection system configured for changing an optical pathlength of a sample element.

FIG. 13 is a cross-sectional view of one embodiment of an analyte detection system 406 comprising compressors 408, 409 for deforming a sample element 402 between absorbance or transmittance measurements. In some embodiments, the analyte detection system 406 may be generally similar to the system 10 disclosed above, and the sample element 402 may be generally similar to the sample element 120 disclosed above, except as further described below. In other embodiments, the analyte detection system 406 may comprise any suitable analyte detection system, with additional structure as further described below.

As shown, the sample element 402 is positionable within the analyte detection system 406 such that a sample chamber 404 of the sample element 402 is positioned between the compressors 408, 409. Each compressor 408, 409 has a hollow portion 412 aligned with the major axis of the compressor to allow for substantially unimpeded passage of a beam of electromagnetic radiation through the compressors 408, 409 and through the sample chamber 404. In one embodiment, the compressors 408, 409 may have a circular cross-section (i.e., the compressors 408, 409 are formed as cylinders). In other embodiments, the compressors 408, 409 can have other cross-sectional shapes. Preferably, the sample element 402 is made of a material which is sufficiently pliable to allow for compression by the compressors 408, 409.

As illustrated in FIG. 13, the analyte detection system 406 includes a proximity switch 445 which, in certain embodiments, detects the insertion of the sample element 402 into the analyte detection system 406. In response to the proximity switch 445, the analyte detection system 406 can advantageously control the forces exerted on the sample element 402 by the compressors 408, 409. In one embodiment, upon activation of the proximity switch 445 by the inserted sample element 402, the compressors 408, 409 contact the sample element 402 and exert oppositely-directed forces 410, 411, respectively, on the sample element 402. In certain embodiments, the forces 410, 411 are sufficiently small so as to avoid substantially compressing the sample element 402. In one such embodiment, the sample element 402 is optimally positioned within the optical path of the beam 443 of the analyte detection system 406 and gently held in this optimal position by the compressors 408, 409, as shown in FIG. 13.

The beam 443 of electromagnetic radiation is passed through the sample chamber 404 to yield a first measurement of absorbance or transmittance by the combination of the sample and the sample element 402 once the sample is drawn into the sample chamber 404. In certain embodiments, the sample is drawn into the sample chamber 404 of the sample element 402 prior to insertion of the sample element 402 into the analyte detection system 406. In other embodiments, the sample is drawn into the sample chamber 404 after the sample element 402 is positioned in the analyte detection system 406.

After the first measurement of absorbance or transmittance is taken, the analyte detection system 406 compresses the sample element 402 by increasing the forces 410, 411 exerted by the compressors 408, 409. These increased forces 410, 411 more strongly compress the sample element 402. In response to this stronger compression, the optical pathlength through the sample element 402 is modified. Preferably, the sample element 402 undergoes plastic deformation due to the compression forces 410, 411, while in other embodiments, the deformation is elastic.

Once the optical pathlength through the sample element 402 is modified, a second measurement of absorbance or transmittance by the combination of the sample and the sample element 402 is taken. The analyte detection system 406 then computes a sample-element referenced absorbance or transmittance of the sample based on the first measurement of absorbance or transmittance at the first pathlength and the second measurement of absorbance or transmittance at the second pathlength, using any of the analysis methods (i.e., difference-calculation, ratio-calculation) disclosed above. Changing the optical pathlength facilitates distinguishing the absorbance or transmittance by the material comprising the sample element 402 from the absorbance or transmittance by the sample within the sample chamber 404. Thus, the analyte detection system 406 provides a measurement of the absorbance or transmittance by the sample which is substantially free of contributions from the absorbance or transmittance of the material comprising the sample element 402. Such measurements can increase the accuracy of the analyte concentration measurements performed by the system 10 based on the sample-element referenced absorbance or transmittance measurements. These analyte concentration measurements may be performed by employing any suitable method, including but not limited to any of the various computational algorithms discussed in further detail in Section IV below. For example, any of the methods disclosed below for determining analyte concentration(s) independent of the optical pathlength through the sample, may be employed.

Figure 14:
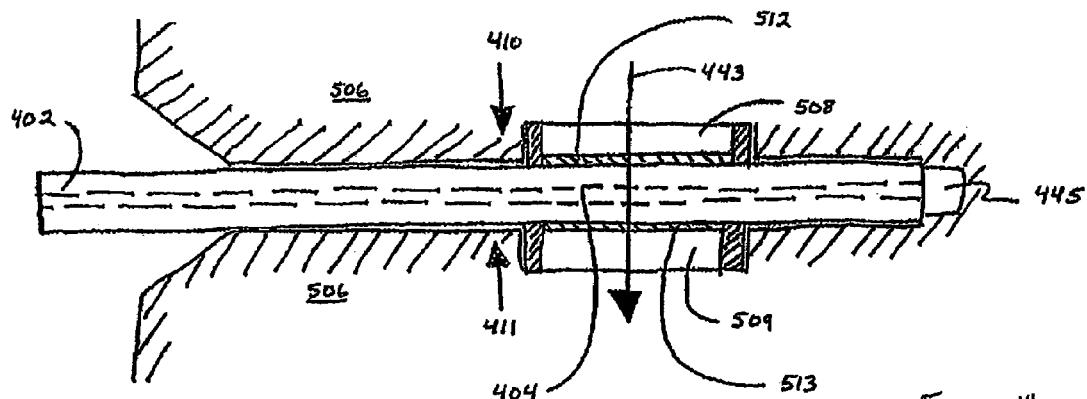
FIG. 14 is a cross-sectional view of another embodiment of an analyte detection system configured for changing an optical pathlength of a sample element.

In the embodiment illustrated by FIG. 13, the compressors 408, 409 decrease the optical pathlength of the sample chamber 404 by compressing the sample chamber 404. FIG. 14 is a cross-sectional view of another embodiment of analyte detection system 506 configured for changing the optical pathlength of the sample element 402. The structure and operation of the analyte detection system 506 are substantially the same as the analyte detection system 406 illustrated in FIG. 13, except with regard to the compressors. As shown in FIG. 14, the compressor 508 comprises a first compressor window 512, and the compressor 509 comprises a second compressor window 513. The compressor windows 512, 513 contact the sample chamber 404 when the compressors 508, 509 grip the sample element 402. The compressor windows 512, 513 serve to more evenly distribute the oppositely-directed forces 410, 411, respectively, across an area of the sample chamber 404.

The compressor windows 512, 513 are preferably at least partially optically transmissive in the range of electromagnetic radiation comprising the beam 443. In one embodiment, one or both of the compressor windows 512, 513 comprises a material that is substantially completely transmissive to the electromagnetic radiation comprising the beam 443. In yet another embodiment, the absorbance of the material of one or both of the compressor windows 512, 513 is not negligible, but it is known and stable for a relatively long period of time, and is stored in memory (not shown) of the analyte detection system 506 so that the system 506 can remove the contributions due to absorbance or transmittance of the material from measurements of the concentration of the analyte(s) of interest. In another embodiment, the absorbance of one or both of the compressor windows 512, 513 is stable for only a relatively short period of time, but the analyte detection system 506 is configured to observe the absorbance of the material and substantially eliminate it from the analyte measurement before the material properties change significantly.

In various embodiments, the compressor windows 512, 513 may be formed from silicon, germanium, polyethylene, or polypropylene, and/or any other suitable infrared-transmissive material.

In certain embodiments, a sample element is referenced so as to overcome transmission properties of the material comprising the sample element by drawing a sample such as whole blood into the sample element and then compressing the sample element to cause the sample chamber of the sample element to expand in a controlled manner, thereby controllably increasing the separation between the inner surfaces of the sample chamber. In this way, the compression of the sample element increases the optical pathlength through the sample chamber. The change in the optical pathlength facilitates distinguishing the absorbance or transmittance by the material comprising the sample element from the absorbance or transmittance by the sample within the sample chamber.

Figure 15:
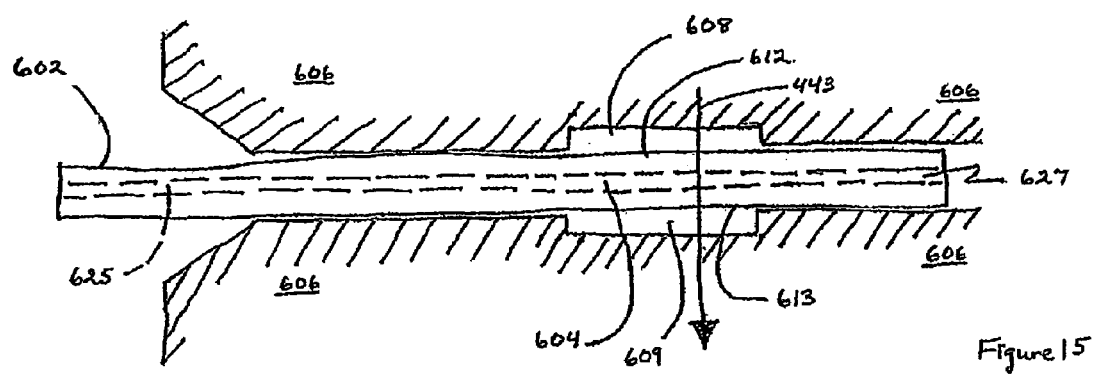
FIG. 15 is a cross-sectional view of another embodiment of an analyte detection system configured for changing an optical pathlength of a sample element.
Figure 16:
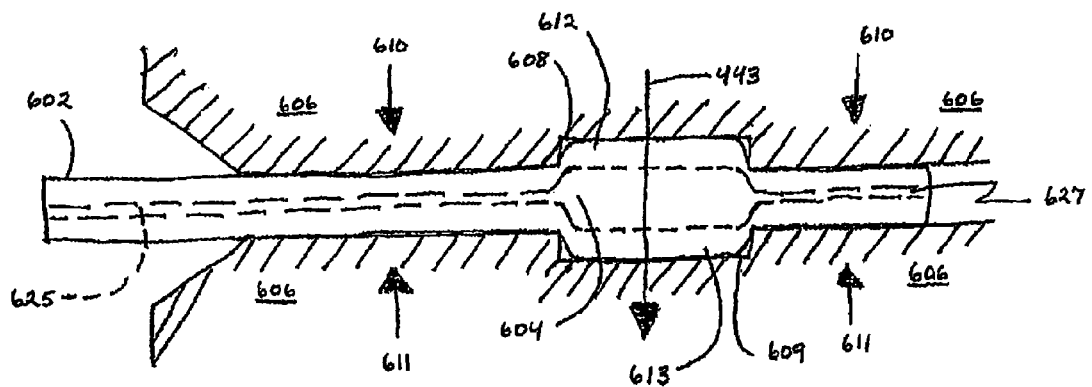
FIG. 16 is a cross-sectional view of the analyte detection system of FIG. 15, illustrating compression and expansion of a sample element employed therewith.

FIGS. 15-16 illustrate an embodiment of an analyte detection system 606 configured for expanding, a sample chamber 604 of a sample element 602. The analyte detection system 606 comprises a first profile 608 adjacent to a first chamber window 612 of the sample chamber 604, and a second profile 609 adjacent to a second chamber window 613 of the sample chamber 604. The profiles 608, 609 are open spaces into which the chamber windows 612, 613 can expand when the sample element 602 is forcibly compressed by the analyte detection system 606. Preferably, the sample element 602 is made of a material which is sufficiently pliable to allow for expansion of the sample chamber 604 into the profiles 608, 609. Preferably, the sample element 602 undergoes plastic deformation, while in other embodiments, the deformation is elastic.

As illustrated in FIG. 16, when the analyte detection system 606 compresses the sample element 602, the analyte detection system 606 exerts oppositely-directed forces 610, 611 on the sample element 602. This causes the chamber windows 612, 613 to respectively expand into the profiles 608, 609, thereby increasing the separation between the inner surfaces of the sample chamber 604 and increasing the optical pathlength of the beam 443 through the sample chamber 604. The change in optical pathlength enables the analyte detection system 606 to compute a sample-element referenced measurement of the absorbance or transmittance of the sample, using any of the analysis methods disclosed above. Thus, the analyte detection system 606 substantially eliminates the contribution of absorbance or transmittance of the material comprising the sample element 602 in order to increase the accuracy of the analyte concentration measurements performed by the system 10 based on the sample-element referenced absorbance or transmittance measurements. These analyte concentration measurements may be performed by employing any suitable method, including but not limited to any of the various computational algorithms discussed in further detail in Section IV below. For example, any of the methods disclosed below for determining analyte concentration(s) independent of the optical pathlength through the sample, may be employed.

FIGS. 17-18 depict another embodiment of the sample element 302 discussed above in connection with FIGS. 11-12. Except as further detailed below, the embodiment of the sample element 302 depicted in FIGS. 17-18 may be generally similar to the sample element 120 disclosed above, and/or the sample element 302 of FIGS. 11-12. In addition, the sample element 302 depicted in FIGS. 17-18 may be employed in practicing any of the sample-element referencing methods disclosed herein, including without limitation those methods discussed in connection with the sample element 302 depicted in FIGS. 11-12.

The sample element 302 further comprises a first strut 320 disposed in the referencing chamber 304 and extending from the first referencing window 304a to the second referencing window 304b. In addition, a second strut 322 is disposed in the sample chamber 306 and extends from the first sample window 306a to the second sample window 306b. The struts 320, 322 are preferably oriented in the chambers 304, 306 so that they extend generally parallel to an optical axis of a beam of energy passed through either of the chambers 304, 306, when the sample element 302 is employed in measuring analyte concentrations. For example, when the sample element 302 is placed in the analyte detection system 10, the strut(s) 320, 322 extend generally parallel to the major axis X and/or the energy beam E.

The struts 320, 322 depicted in FIGS. 17-18 comprise members having sufficient column and tensile strength to minimize or prevent inward or outward deflection of the referencing windows 304a, 304b and sample windows 306a, 306b, respectively. The struts 320, 322 advantageously assist in preserving the planarity of the windows 304a, 304b, 306a, 306b, thereby enhancing the accuracy of some analyte-concentration measurements taken with the sample element 302. Although various computational algorithms are disclosed below for preserving measurement accuracy despite imperfections in sample-element geometry (e.g., pathlength, window planarity, window parallelism), the struts 320, 322 may be employed instead of or in addition to various combinations of such algorithms when measuring analyte concentrations.

In the illustrated embodiment, the struts 320, 322 comprise cylindrical members (i.e. having a circular cross-section); however, any other suitable cross-sectional shape (including without limitation oval, square, rectangular, triangular, etc.) may be employed. In the illustrated embodiment, the struts 320, 322 maintain a substantially constant cross-section as they extend from the first window 304a/306a to the second window 304b/306b; however, a varying cross-section may be employed.

In the embodiment shown in FIGS. 17-18, the struts 320, 322 are of substantially similar cross-sectional area, and a single strut is employed in each of the chambers 304, 306. However, the number of struts employed in each chamber may vary, as two, three, four or more may be used in each chamber, and the total cross-sectional area of the referencing-chamber struts may either equal (in one embodiment) or differ from (in another embodiment) that of the sample-chamber struts. Similarly, strut(s) may be employed in only one, or both, of the referencing and sample chambers 304, 306.

In one embodiment, each of the struts 320, 322 is substantially opaque to the wavelength(s) of energy employed by the analyte detection system (such as the system 10) with which the sample element 302 is employed. For example, the struts 320, 322 may be formed from a material which is substantially opaque to the wavelength(s) of interest, in the source intensity range employed by the detection system, and when formed in a pathlength less than or equal to the shorter of the struts 320, 322. In another example, the struts may be formed from a material which does not meet the above criteria, but a mask layer (not shown) may be positioned in each strut, or in or on one of the windows 304a/304b and one of the windows 306a/306b, in axial alignment with each strut. The mask layers are substantially opaque to the wavelength(s) of interest and are shaped and sized to conform to the (largest) cross-section of the corresponding struts, so as to substantially prevent passage of the energy beam E through the struts 320, 322. In still further embodiments, any suitable structure may be employed to substantially prevent passage of the energy beam E through the struts 320, 322.

By making the struts 320, 322 substantially opaque to the wavelength(s) of interest, or by otherwise preventing prevent passage of the energy beam E through the struts 320, 322, the absorbance/transmittance of the struts drops out from the absorbance/transmittance data when the difference or ratio is computed of the absorbance/transmittance measured in each chamber 304, 306. In other words, by making the absorbance/transmittance of the struts 320, 322 independent of the length of the struts, their absorbance/transmittance can be accounted for in computing analyte concentrations, despite their difference in length. In another embodiment, a similar result can be obtained by otherwise constructing the struts 320, 322 to have substantially equal absorbance or transmittance, but without making the struts 320, 322 opaque.

In yet another embodiment, the strut(s) 320, 322 may be formed from a material which is highly transmissive of the wavelength(s) of interest. For example, where infrared wavelengths are employed in the measurement of analyte concentrations, the strut(s) may be formed from silicon, germanium, polyethylene, polypropylene, or a combination thereof.

FIG. 17, as an upper plan view of the sample element 302, also depicts a vent passage 324 and supply passage 326 in fluid communication with the referencing and sample chambers 304, 306, respectively. The vent and supply passages 324, 326 may be generally similar to their counterparts disclosed above in connection with the sample element 120. In addition, the vent passage 324 and supply passage 326 may be employed in any of the embodiments of the sample element 302 discussed herein.

It is further contemplated that one or more struts of the type presently disclosed may be employed in the sample chamber 200 of the sample element 120 , so as to extend from the upper window 202c to the lower window 202d.

FIGS. 19 and 20 depict yet another embodiment of the sample element 302 discussed above in connection with FIGS. 11-12 and 17-18. Except as further detailed below, the embodiment of the sample element 302 depicted in FIGS. 19-20 may be generally similar to the sample element 120 disclosed above, and/or the sample elements 302 of FIGS. 11-12 and 17-18. In addition, the sample element 302 depicted in FIGS. 19-20 may be employed in practicing any of the sample-element referencing methods disclosed herein, including without limitation those methods discussed in connection with the sample elements 302 depicted in FIGS. 11-12 and 17-18.

The sample element 302 depicted in FIGS. 19-20 further comprises a stiffening layer 340 which is secured to the sample element 302, preferably on the underside thereof, by any appropriate means, such as adhesives, heat bonding, ultrasonic bonding, integral formation, etc. The stiffening layer 340 is sized and shaped, and its material chosen, to impart additional stiffness and rigidity to the sample element 302. The stiffening layer 304 may be formed from the materials used to form the balance of the sample element 302, or other suitable materials as desired. The stiffening layer 340 includes an opening 342 which is aligned with the referencing chamber 304 and sample chamber 306 to permit a beam of electromagnetic energy (such as the beam E when the sample element 302 is employed with the system 10) to pass to the windows 304b, 306b. Other than the opening 342, the stiffening layer 340 is preferably coextensive with the underside of the sample element 302.

In other embodiments, a similar stiffening layer may be secured to the upper side of the sample element 302, instead of or in addition to the stiffening layer 340 depicted in FIGS. 19-20. Such an upper-side stiffening layer may include a staggered portion to conform to the difference in thickness between the reference and sample chambers 304, 306 on the upper side of the sample element 302.

It is further contemplated that one or more stiffening layers similar to the layer 340 may be employed with the sample element 120 disclosed above, secured to one or both of the first and third layers 220, 240.

Figure 21:
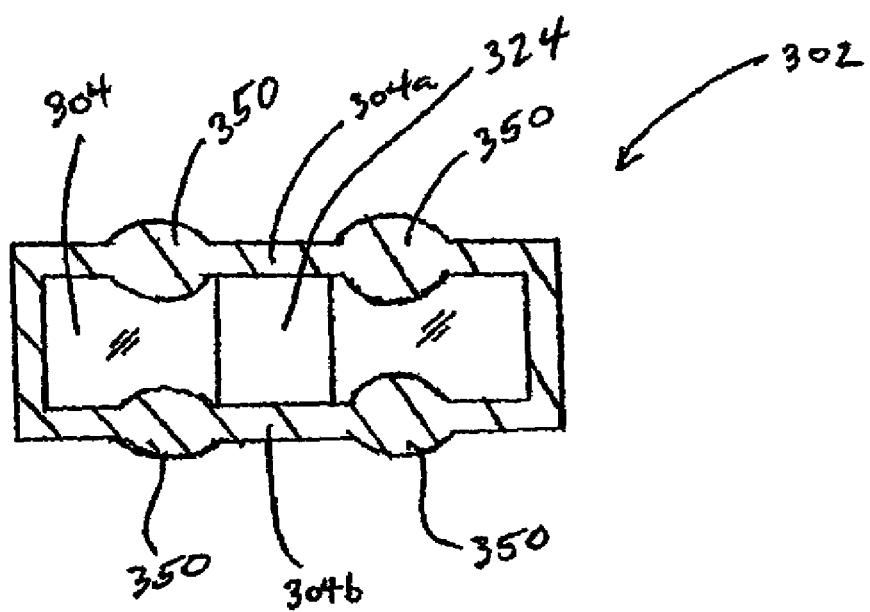
FIG. 21 is an end sectional view of another embodiment of a sample element.

FIG. 21 depicts another embodiment of the sample element 302 discussed above in connection with FIGS. 11-12 and 17-20. Except as further detailed below, the embodiment of the sample element 302 depicted in FIG. 21 may be generally similar to the sample element 120 disclosed above, and/or the sample elements 302 of FIGS. 11-12 and 17-20. In addition, the sample element 302 depicted in FIG. 21 may be employed in practicing any of the sample-element referencing methods disclosed herein, including without limitation those methods discussed in connection with the sample elements 302 depicted in FIGS. 11-12 and 17-20.

The sample element 302 depicted in FIG. 21 further comprises stiffening ribs 350 which are integrally formed with one or both of the first and second referencing windows 304a, 304b. The stiffening ribs 350 preferably extend across the entire length of the windows 304a, 304b, and may continue into the balance of the sample element 302. The stiffening ribs 350 depicted in FIG. 21 are arranged to extend longitudinally across the windows 304a, 304b so that they extend generally orthogonal to an optical axis of a beam of energy passed through the chamber 304 when the sample element 302 is employed in measuring analyte concentrations. For example, when the sample element 302 is placed in the analyte detection system 10, the ribs 350 extend generally orthogonal to the major axis X and/or the energy beam E. In other embodiments, the ribs 350 may extend in any direction, so long as they are oriented to extend generally orthogonal to such an optical axis. Furthermore, the ribs 350 may be employed in any combination of the windows 304a, 304b, 306a, 306b, or the windows 202c, 202d of the sample element 120.

In any of these embodiments, any suitable size, shape and number of ribs may be employed, other than those depicted in FIG. 21. However, in one embodiment, the configuration of ribs employed on the window 304a substantially matches that of the window 306a, and the configuration of ribs employed on the window 304b substantially matches that of the window 306b. Such an arrangement may improve the accuracy of the sample-element referencing methods employed with the sample element 302.

The ribs 350 advantageously assist in preserving the planarity of the windows 304a, 304b, 306a, 306b, thereby enhancing the accuracy of analyte-concentration measurements taken with the sample element 302. Although various computational algorithms are disclosed below for preserving measurement accuracy despite imperfections in sample-element geometry (e.g., pathlength, window planarity, window parallelism), the ribs 350 may be employed instead of or in addition to various combinations of such algorithms when measuring analyte concentrations.

IV. ALGORITHMS

This section discusses a number of computational methods or algorithms which may be used to calculate the concentration of the analyte(s) of interest in the sample S, and/or to compute other measures that may be used in support of calculations of analyte concentrations. Any one or combination of the algorithms disclosed in this section may reside as program instructions in the memory 185 so as to be accessible for execution by the processor 180 of the analyte detection system 10 to compute the concentration of the analyte(s) of interest in the sample, or other relevant measures. Alternatively, any one or combination of the algorithms disclosed in this section may be executed by or in connection with a Fourier Transform Infrared Spectrometer (FTIR) device, such as the SPECTRUM ONE model available from Perkin-Elmer Inc., of Wellesley, Mass., for determining analyte concentrations or other measures. In addition, any one or combination of the algorithms disclosed in this section may be employed in connection with any of the embodiments of the method 190 depicted in FIG. 7 and discussed above. For example, the disclosed algorithms may be employed to compute the concentration of the analyte(s) of interest in the sample S from (any) final transmittance values $TF_{\lambda,1}$, $TF_{\lambda,2}$, ... $TF_{\lambda,n}$, output by the method 190.

A. Methods for Determining Analyte Concentrations

In many measurements, the contribution from the analyte of interest (e.g., glucose) to the measured absorption spectrum is often only a small percentage of the contribution from other substances within the sample. For example, blood by volume is typically composed of about 70% water, about 30% solids, mostly protein, and only about 0.1% glucose. Blood also includes other species such as urea, alanine, and in some cases alcohol or other sugars such as fructose. Similarly, plasma includes only a small percentage of glucose, as well as other species. Therefore, blood or plasma glucose measurements are highly sensitive and vulnerable to inaccuracies.

If an accurate glucose measurement is desired, the characteristics of each of the different constituents of the sample should be considered. Because the sample absorption at any given wavelength is a sum of the absorptions of each component of the sample at that wavelength, IR absorption measurements are complicated by the presence of these other components. Consequently, to allow effective compensation and adjustments to measured IR absorption for the presence of other components of the blood or plasma, it is helpful to understand which constituents are present in the sample, understand their effects on the analyte that is being measured (such as glucose), and correct for any differences that intrinsic and measuring-device-related variables may cause.

Advantageously, absorption data in the mid-IR spectral region (for example, about 4 microns to about 11 microns) are used. Although water is the main contributor to the total absorption across this spectral region, the peaks and other structures present in the blood or plasma spectrum from about 6.8 microns to 10.5 microns are due to the absorption spectra of other components of the blood or plasma. The 4 to 11 micron region has been found advantageous because glucose has a strong absorption peak structure from about 8.5 to 10 microns, whereas most other constituents of the blood or plasma have a low and flat absorption spectrum in the 8.5 to 10 micron range. The main exceptions are water and hemoglobin, both of which absorb fairly strongly in this region, and which are also the two most significant components in terms of concentration in the blood or plasma. Certain embodiments of the techniques described herein are thus directed to removing the contributions of water and hemoglobin from this spectral region to resolve the contribution, and thus concentration, of glucose in the sample.

B. Pathlength-Insensitive Determinations of Analyte Concentrations

In certain embodiments, a method determines an analyte concentration in a sample comprising the analyte and a substance. The method comprises providing an absorption spectrum of the sample, with the absorption spectrum having an absorption baseline. The method further comprises shifting the absorption spectrum so that the absorption baseline approximately equals a selected absorption value in a selected absorption wavelength range. The method further comprises subtracting a substance contribution from the absorption spectrum. Thus, the method provides a corrected absorption spectrum substantially free of a contribution from the substance.

In certain embodiments, providing the absorption spectrum comprises providing the transmittance spectrum of the sample, with the transmittance spectrum having a transmittance baseline. In certain embodiments, the transmittance spectrum of the sample is provided by transmitting at least a portion of an infrared signal through the sample. The infrared signal comprises a plurality of wavelengths. The portion of the infrared signal transmitted through the sample is measured as a function of wavelength. Various configurations and devices can be used to provide the transmittance spectrum in accordance with embodiments described herein.

In certain embodiments, the transmittance baseline is defined to be the value of the transmittance spectrum at wavelengths at which transmittance is a minimum. For blood, this value is typically at about 6.1-6.2 microns where water and hemoglobin both are strong absorbers. While the transmittance spectrum from the sample at these wavelengths is expected to be nearly zero, various effects, such as instrumental error and thermal drift, can result in a nonzero contribution to the transmittance baseline. In addition, effects such as instrumental error and thermal drift can result in a wavelength shift of known features in the transmittance spectrum from the expected wavelengths of these features.

In certain such embodiments, providing the absorption spectrum comprises shifting the transmittance spectrum so that the transmittance baseline approximately equals zero in a selected transmittance wavelength range. In certain embodiments in which the sample comprises blood or plasma, the selected transmittance wavelength range comprises wavelengths at which the transmittance is a minimum. In certain such embodiments, the selected transmittance wavelength range comprises wavelengths between approximately 6 microns and approximately 6.15 microns. In other such embodiments, the selected transmittance wavelength range comprises wavelengths between approximately 12 microns and approximately 13 microns. The transmittance spectrum at these wavelengths may be partially affected by contributions from various components that are present at low concentration levels. In still other such embodiments, the selected transmittance wavelength range comprises wavelengths approximately equal to 3 microns. Each of these wavelengths corresponds to a strong water absorption peak.

In embodiments in which there is a nonzero contribution to the transmittance baseline, the transmittance spectrum may be shifted. In certain embodiments, the transmittance spectrum is shifted so that the transmittance spectrum in the wavelength range of 6 to 6.2 microns is approximately equal to zero. In embodiments in which known features are shifted in wavelength from their expected wavelengths, the transmittance spectrum can be shifted in wavelength. In addition, the shifting of the transmittance spectrum can be performed nonlinearly (e.g., shifting different wavelengths by differing amounts across the transmittance spectrum).

Providing the absorption spectrum further comprises determining the absorption spectrum from the transmittance spectrum. In certain embodiments, the relation between the transmittance spectrum and the absorption spectrum is expressed as:

$$A(\lambda) = \ln\left(\frac{1}{T(\lambda)}\right),$$

where $\lambda$ is the wavelength, $A(\lambda)$ is the absorption as a function of wavelength, and $T(\lambda)$ is the transmittance as a function of wavelength.

In certain embodiments, the method comprises shifting the absorption spectrum so that its absorption baseline approximately equals a selected absorption value (such as 0, 0.5, 1, etc.) in a selected absorption wavelength range. In certain embodiments, the absorption baseline can be selected to be defined by a portion of the absorption spectrum with low absorption. In certain embodiments in which the sample comprises blood or plasma, the selected absorption wavelength range comprises wavelengths between approximately 3.8 microns and approximately 4.4 microns. In certain other embodiments, the selected absorption wavelength range comprises wavelengths between 9 microns and approximately 10 microns.

In certain other embodiments in which the sample comprises blood, the absorption baseline is defined to be the magnitude of the absorption spectrum at an isosbestic wavelength at which water and a whole blood protein have approximately equal absorptions. In such embodiments, the absorption spectrum is shifted to a selected value at the isosbestic wavelength by adding or subtracting a constant offset value across the entire wavelength spectral data set. In addition, the shifting of the absorption spectrum can be performed nonlinearly (e.g., shifting the portions of the absorption spectrum in different wavelength ranges by different amounts). Shifting the absorption spectrum such that the absorption is set to some value (e.g., 0) at a protein-water isosbestic point preferably helps remove the dependence on hemoglobin level of the overall spectrum position relative to zero. For samples comprising plasma containing whole blood protein, similar techniques can be applied.

The effective isosbestic point can be expected to be different for different proteins in different solutions. Exemplary whole blood proteins include, but are not limited to, hemoglobin, albumin, globulin, and ferritin. These isosbestic wavelengths can be used to obtain a current measure of the effective optical pathlength in the filled cuvette, either before or during measurements at other wavelength ranges.

Such information is very useful in subsequent calculations for compensation of instrument-related pathlength non-linearities. Because the measured absorption of the protein and water are identical at the isosbestic wavelength, the measured absorption at the isosbestic wavelength is independent of the ratios of the protein concentration and the water concentration (hematocrit level). At an isosbestic wavelength, for a given sample volume, the same amount of absorption would be observed whether the sample was entirely water, entirely protein, or some combination of the two. The absorption at the isosbestic wavelength is then an indication of the total sample volume, independent of the relative concentrations of water and protein. Therefore, the observed absorption at an isosbestic wavelength is a measure of the pathlength of the sample only. In certain embodiments, the observed absorption at an isosbestic wavelength can be useful for measuring the effective optical pathlength for a sample. As a result, various embodiments of the above-described method may be employed to accurately determine the concentration of analyte(s) of interest in a sample independent of optical pathlength, i.e. without need for prior knowledge of the pathlength and/or without requiring that the sample chamber of the sample element conform closely to a specified or expected pathlength. Additionally, such information can be used in subsequent calculations for compensation of instrument-related pathlength nonlinearities. In certain embodiments, these measurements can be made before or concurrently with absorption measurements in other wavelength ranges.

C. Subtraction of Absorption Due to Non-Analyte Components of Sample

In certain embodiments, a method of analyzing blood absorption data has two major components: data clean-up and spectroscopic analysis. The goal of the data clean-up is to remove instrumental artifacts from the data, so that what remains is an accurate representation of the blood spectra. This method is machine- and protocol-related and the clean-up required for Fourier Transform Infrared (FTIR) spectrometer data is considerably different from the clean-up required for discrete-wavelength transmission data. While the exemplary embodiments discussed below are applied to blood absorption data, other embodiments can be applied to plasma absorption data as well.

Figure 22:
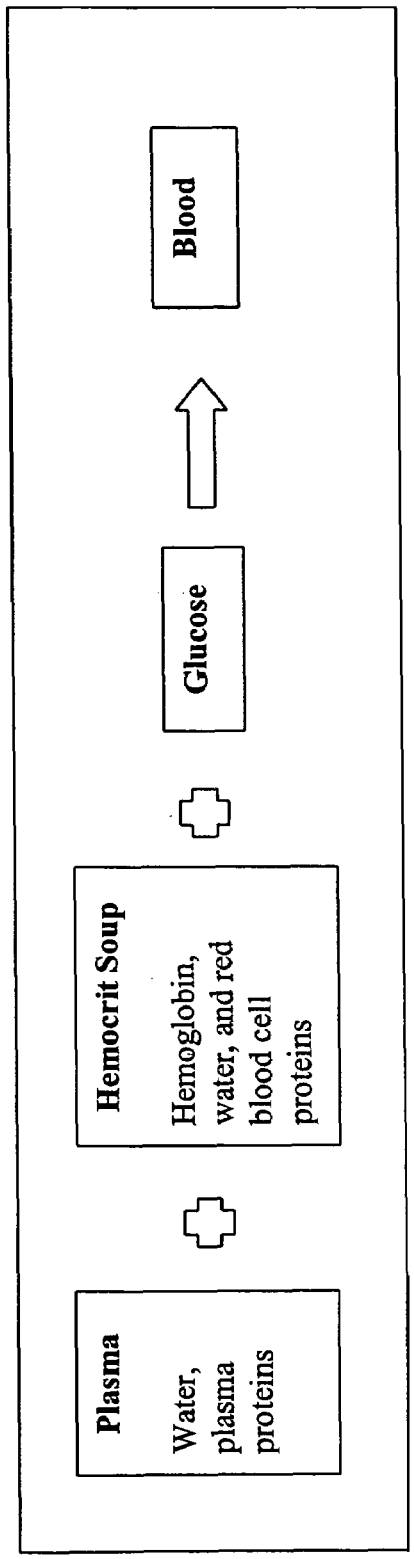
FIG. 22 schematically illustrates the major constituents of three components mixed to produce blood samples.

The goal of the spectroscopic analysis is to derive the ratio of the analyte volume (for example, glucose volume) to the total blood volume using essentially artifact-free spectra. The blood samples are primarily a mixture of three components: plasma, hematocrit soup and glucose as illustrated in FIG. 22. As illustrated in FIG. 22, "hematocrit soup" comprises the combination or mixture of the components of blood other than the plasma and glucose components.

Certain embodiments of the method are based on knowledge of reference absorption spectra for each of the three components. The protein content of plasma is ignored in pooled-blood embodiments, because it is the same for each blood sample. This is a liberty that can be taken with pooled blood but that cannot be extended to individual blood samples, where additional components will be required. The reference spectra for water (plasma) and the analyte (for example, glucose) can be determined with FTIR measurements. The reference spectra for the hemocrit soup can be determined from the differential hemoglobin spectra calculated using the blood data.

One goal of the spectroscopic analysis can be to derive the ratio of the analyte volume (for example, glucose volume) to the total blood volume. The process of measuring a glucose concentration can include subtracting one or more contributions to the absorption spectrum from other substances in the blood that interfere with the detection of the glucose. In certain embodiments, a reference substance absorption spectrum is provided and is scaled by multiplying it by a scaling factor. The scaled reference substance absorption spectrum is subtracted from the measured absorption spectrum. This procedure thus preferably provides the corrected absorption spectrum which is substantially free of a contribution from the substance.

Such procedures can be used to subtract the absorption contributions of water and/or hemoglobin, as well as other constituents of blood or plasma. In addition, the scaling factor provides a measure of the absorption due to the substance of the reference substance absorption spectrum. As described more fully below, in embodiments in which multiple scaling factors are determined for multiple substances, ratios of the scaling factors provide information regarding the concentration ratios of the substances in question. These determinations of the concentration ratios are substantially independent of the optical pathlength through the sample. Such concentration ratios can be used to determine the concentration of a selected substance within the sample regardless of the optical path length through the sample.

In certain embodiments, the measured absorption spectrum can be further corrected for other contributions which are not due to the analyte of interest. In certain such embodiments, the measured absorption spectrum can be corrected for a substance which interferes with determining the analyte concentration. In certain embodiments in which the sample comprises a second substance which interferes with determining the analyte concentration to a lesser extent than does the substance, the measured absorption spectrum can be further corrected by calculating a second substance contribution of the absorption data and subtracting the second substance contribution from the absorption data, thereby providing corrected absorption data substantially free of a contribution from the second substance.

For example, alcohol is a potentially interfering substance with the glucose measurement because the absorption of alcohol is similar to that of glucose in the wavelength range of interest. It is observed that the peak height ratio of the absorption peak at about 9.6 microns to the absorption peak at about 9.2 microns for pure glucose is approximately 1.1-1.2, and the ratio for pure alcohol is approximately 3.0-3.2. This ratio of peak heights varies between these two values for absorption spectra for mixtures of glucose and alcohol. Thus, the peak height ratio can be used to determine the relative concentrations of alcohol and glucose. The contribution from alcohol can then be subtracted from the measured absorption spectrum. In certain embodiments, the process can be repeated for other analytes of interest in sufficient quantities.

In certain embodiments, the measured absorption spectrum can be corrected for contributions from free protein, which has an absorption peak centered around 7.1 microns. In certain other embodiments, the measured absorption spectrum can be further corrected for contributions from a boundary layer between water and a whole blood protein. Features in the measured absorption spectrum due to components of the boundary layer arise from interactions between the water and whole blood protein. These spectral features are ascribed to "bound" components or hydrated protein. The corresponding contributions across the measured absorption spectrum can be corrected by subtracting the appropriate scaled reference absorption, such that the corrected absorption spectrum is approximately zero for a selected range of wavelengths. In certain embodiments, the range of wavelengths is between about 7.0 and 7.2 microns, or alternatively between 7.9 and 8.1 microns, or alternatively at a combination of wavelength ranges.

Temperature also affects the correct subtraction of the water contribution to the total spectrum because the absorption spectrum of water changes with temperature changes. It is therefore advantageous for the system to store several different water reference spectra, with each one applicable to a selected temperature range. The appropriate reference would be selected for scaling and subtraction based on the temperature of the sample. In some embodiments, hardware such as thermocouples, heaters, and the like may be provided to directly measure or control the temperature of the sample. Although this approach may be suitable at times, it can be difficult to accurately measure and control the blood temperature as the sample size is very small, and the actual blood temperature may vary from the cuvette temperature or the ambient temperature surrounding the cuvette.

The contribution of temperature to the absorption spectra can alternatively be addressed by analyzing the sample spectrum itself, because different parts of the water absorption spectrum are affected by temperature by different amounts. For example, the absorbance difference of the water absorption spectrum between about 4.9 microns and 5.15 microns is not very dependent on temperature, whereas the absorbance difference between 4.65 microns and 4.9 microns is highly temperature dependent. As temperature changes for a given sample with constant water concentration, the absorbance difference between 4.65 and 4.9 microns will change a lot, and the absorbance difference between 4.9 and 5.15 microns will not change much at all. Thus, the ratio of the absorbance difference between two points having high temperature dependence (e.g., 4.65 and 4.9 microns) to the absorbance difference between two points having low temperature dependence (e.g., 4.9 and 5.15 microns) can be used as a measure of temperature. Once this measurement is made, an appropriate selection from several different stored water reference curves can be made.

In certain embodiments, the reference substance absorption spectrum is provided by correcting a stored spectrum for wavelength-dependent nonlinearities. For example, where the substance comprises water, knowledge of the optical pathlength (based on the total sample absorption at one or more isosbestic wavelengths) as well as the measured absorption at one or more wavelengths dominated by water absorption (e.g., between approximately 4.5 and 5 microns) can be used to correct a stored reference water absorption spectrum for wavelength nonlinearities across the spectrum. Such corrections of the stored reference spectrum are advantageous for reducing distortions in the final results. Similarly, prior knowledge of optical pathlength based on total sample absorption at an isosbestic wavelength, as well as on total protein absorption in a selected wavelength range (e.g., 7.0-7.2 microns, or 7.9-8.1 microns) allows for the modification of a reference protein absorption spectrum that is compensated for nonlinearities. Other wavelength-dependent nonlinearities to be corrected for can be produced by the sample element, including, but not limited to, scattering and fringing.

In certain embodiments, after correcting the measured absorption spectrum for contributions of one or more substances, the corrected absorption spectrum is fitted with reference analyte spectral data to provide a measure of the analyte concentration. The reference analyte spectral data can include data at a wavelength near an analyte absorption maximum. For example, the absorption spectrum of glucose includes various peaks, with the two largest peaks at wavelengths of approximately 9.25 and 9.65 microns, respectively. The absorption difference of the corrected absorption spectrum between a wavelength of about 8.5 microns and a wavelength of approximately 9.65 microns can provide a measure of the glucose concentration in the blood sample. Following the definition of glucose in blood (i.e., a measure of glucose per volume of the sample), a useful measure for glucose concentration is preferably obtained from algorithmically-derived infrared quantities by dividing the final glucose quantity by total water, total protein, or alternatively a combination of both.

Although the above discussion focuses on data sets comprising measurements over the entire range of IR wavelengths, it will be appreciated that it is not necessary to obtain data across the entire spectrum, but only at the discrete wavelengths used in the analysis. In certain embodiments where water and hemoglobin contributions are subtracted from a whole blood spectrum to find glucose concentration, as little as ten or fewer total measurements are needed. Additional components to be subtracted may require one or two more measurements each.

For example, to characterize the water contribution, measurements at about 4.7 microns and 5.3 microns may be obtained. For characterizing hemoglobin, measurements at about 8.0 and 8.4 microns may be obtained. The glucose characterization may involve a measure of the difference between about 8.5 microns and 9.6 microns. This is six values, two for each component. In embodiments where it is desired to zero the transmittance curve and shift the absorbance values, it may be desirable to further make transmittance measurements at about the 6.1 micron water absorbance peak and the 4.1 micron water/protein isosbestic point. As described above, the addition of another data point at about 4.9 microns allows the determination of temperature. Another measurement at the lower alcohol peak of about 9.25 microns can be used to compensate the glucose measurement for alcohol content as well as is also described above. In certain embodiments, the values of optical density at these six wavelengths can be expressed as six linear equations which can be solved to yield the glucose concentration path length and the ratio of glucose volume to total blood volume.

In certain embodiments, the method uses the optical density (OD) for a parallel cuvette, parallel illumination and "delta-function" filter, which can be expressed as:

$$OD_i = (c_w \alpha_{wi} + c_h \alpha_{hi} + c_g \alpha_{gi}) \cdot d \qquad (1)$$

where:
  d=cuvette path length;
  $c_w$=water volume concentration;
  $c_h$=hematocrit soup volume concentration;
  $c_g$=glucose volume concentration;
  $\alpha_{wi}$=water absorption at wavelength 'i'; and
  $\alpha_{hi}$=hematocrit soup absorption at wavelength 'i'; and
  $\alpha_{gi}$=glucose absorption at wavelength 'i'.

The absorption of the various components (e.g., $\alpha_{wi}$, $\alpha_{hi}$, $\alpha_{gi}$) at various wavelengths is a property of the components themselves, and can be known or provided to the system for use in the calculation of the analyte concentrations. In various embodiments described below, the blood sample is modeled as a three-component mixture of water, hematocrit soup, and glucose (i.e., $c_w + c_h + c_g = 1$). Other embodiments can model the blood sample with more components, fewer components, or different components.

In certain embodiments, the method uses three two-wavelength sets. The first set is in the wavelength region where water absorption dominates. The second set is in a region where water and hematocrit soup absorptions dominate, and the third set in a region where absorptions from all three components dominate. In certain embodiments, the calculations are based on OD differences of each wavelength pair to reduce or minimize offsets and baseline drift errors. Absorption values for the three components at each of the six wavelengths are shown in Table 1:

| Wavelength | $\alpha_{wi}$ | $\alpha_{hi}$ | $\alpha_{gi}$ |
|---|---|---|---|
| 1 | $\alpha_{w1}$ | 0 | 0 |
| 2 | $\alpha_{w2}$ | 0 | 0 |
| 3 | $\alpha_{w3}$ | $\alpha_{h3}$ | 0 |
| 4 | $\alpha_{w4}$ | $\alpha_{h4}$ | 0 |
| 5 | $\alpha_{w5}$ | $\alpha_{h5}$ | $\alpha_{g5}$ |
| 6 | $\alpha_{w6}$ | $\alpha_{h6}$ | $\alpha_{g6}$ |

Substituting these values from Table 1 into Equation (1) yields the following relations:

$$OD_1 = c_w \alpha_{w1} d; \quad (2)$$

$$OD_2 = c_w \alpha_{w2} d; \quad (3)$$

$$OD_3 = (c_w \alpha_{w3} + c_h \alpha_{h3}) \cdot d; \quad (4)$$

$$OD_4 = (c_w \alpha_{w4} + c_h \alpha_{h4}) \cdot d; \quad (5)$$

$$OD_5 = (c_w \alpha_{w5} + c_h \alpha_{h5} + c_g \alpha_{g5}) \cdot d; \text{ and} \quad (6)$$

$$OD_6 = (c_w \alpha_{w6} + c_h \alpha_{h6} + c_g \alpha_{g6}) \cdot d. \quad (7)$$

Certain embodiments of the method comprise computing the quantity A which is equal to the product of the water concentration and the path length. The quantity A can be termed the "water scaling factor," and can be expressed by the following relation:

$$A = \frac{OD_2 - OD_1}{(\alpha_{w2} - \alpha_{w1})} = c_w d. \quad (8)$$

In certain embodiments in which the values of water absorption at the two wavelengths is known or provided to the system, this ratio of the difference of two measured absorption values with the difference of two reference absorption values at the same wavelengths yields a water scaling factor A indicative of the amount of water in the sample.

Using A and the water absorptions at each wavelength, the "water free" OD can then be calculated and expressed by the following relation:

$$OD_i' = OD_i - A\alpha_{wi}. \quad (9)$$

In this way, the "water free" OD value equals the measured OD value minus the scaled reference absorption value for water. Combining Equation (9) and Equations (4)-(7) yields the following relations:

$$OD_3' = c_h \alpha_{h3} d; \quad (10)$$

$$OD_4' = c_h \alpha_{h4} d; \quad (11)$$

$$OD_5' = (c_h \alpha_{h5} + c_g \alpha_{g5}) \cdot d; \text{ and} \quad (12)$$

$$OD_6' = (c_h \alpha_{h6} + c_g \alpha_{g6}) \cdot d. \quad (13)$$

In certain embodiments, the "water free" absorptions at wavelengths 3 and 4 are used to calculate the quantity B which is proportional to the product of the hemocrit soup concentration and path length. The quantity B can be termed the "hemocrit soup scaling factor," and can be expressed by the following relation:

$$B = \frac{OD_4' - OD_3'}{\alpha_{h4} - \alpha_{h3}} = c_h d. \quad (14)$$

In certain embodiments in which the values of hematocrit soup absorption at the two wavelengths is known or provided to the system, this ratio of the difference of two "water free" OD values with the difference of two reference absorption values for hematocrit soup at the same wavelengths yields a hematocrit soup scaling factor B indicative of the amount of hematocrit soup in the sample.

By using B and the hematocrit soup absorptions at each wavelength, the "glucose only" OD is calculated in certain embodiments to be expressed by the following relation:

$$OD_i'' = OD_i' - B\alpha_{hi}. \quad (15)$$

In this way, the "glucose only" OD value equals the measured OD value minus the scaled reference absorption values for water and for hematocrit soup.

From Equations (15), (12) and (13), the following relations can be calculated:

$$OD_5'' = c_g \alpha_{g5} d; \text{ and} \quad (16)$$

$$OD_6'' = c_g \alpha_{g6} d. \quad (17)$$

The glucose concentration path length product, given by the quantity C, can be termed the "glucose scaling factor," and can be expressed by the following relation:

$$C = \frac{OD_6'' - OD_5''}{\alpha_{g6} - \alpha_{g5}} = c_g d. \quad (18)$$

In certain embodiments in which the values of glucose absorption at the two wavelengths is known or provided to the system, this ratio of the difference of two "glucose only" OD values with the difference of two reference absorption values for glucose at the same wavelengths yields a glucose scaling factor C indicative of the amount of glucose in the sample.

The desired ratio of glucose volume to total blood volume can then be expressed (using the relation $c_w + c_h + c_g = 1$) by the following relation:

$$c_g = \frac{c_g * d}{(c_w + c_h + c_g)} = \frac{C}{A + B + C}. \quad (19)$$

By taking the ratio of the glucose scaling factor to the sum of the water scaling factor, the hematocrit soup scaling factor, and the glucose scaling factor, the resulting concentration ratio $C_g$ is substantially independent of the path length of the sample. Thus, certain embodiments described herein provide a method of determining the glucose content of a blood sample independent of the path length of the blood sample.

D. System and Temperature Effects on Absorption

In certain embodiments, various non-analyte contributions to the measured absorption spectrum can be determined. Absorption by blood in the wavelength region from approximately 4.4 to 5.5 microns is primarily due to water. Transmission or absorption measurements in this "water region" can be used to determine the water content of the blood sample without considering other blood constituents. At other wavelengths, the measurements depend on the concentrations and spectral properties of other blood components. In certain embodiments, the measurements can also be influenced by non-analyte contributions, including but not limited to, finite filter widths, blood temperature, filter temperature and cuvette shape. In certain embodiments, these effects can be corrected at each wavelength before calculating the blood component concentrations. The water region offers a convenient wavelength range to separate system and temperature effects from component concentration effects. Certain embodiments of the analysis method utilize a model for transmission of a water-filled cuvette illuminated with parallel light as a function of cuvette shape, water temperature, filter temperature, and filter shape. Embodiments are described herein which use data from the water region to determine system parameters for both non-parallel and parallel cuvettes.

In certain embodiments, the resulting absorption spectrum (e.g., after being corrected for instrumental drift, optical pathlength, distortions, and contributions from major components) can be fitted with a reference glucose absorption spectrum to remove the glucose contribution. This absorption spectrum can be used further for individual determination of residual components. In certain embodiments, the residual components include high molecular weight substances, including but not limited to, other proteins, albumin, hemoglobin, fibrinogen, lipoproteins, and transferring. In certain embodiments, the residual components include low molecular weight substances, including but not limited to, urea, lactate, and vitamin C. The final glucose measure can be corrected for the presence of such lower level potentially interfering substances by subtracting reference spectra of specific substances, such as urea, from the residual data.

1. Integral Form of Optical Density

Figure 23:
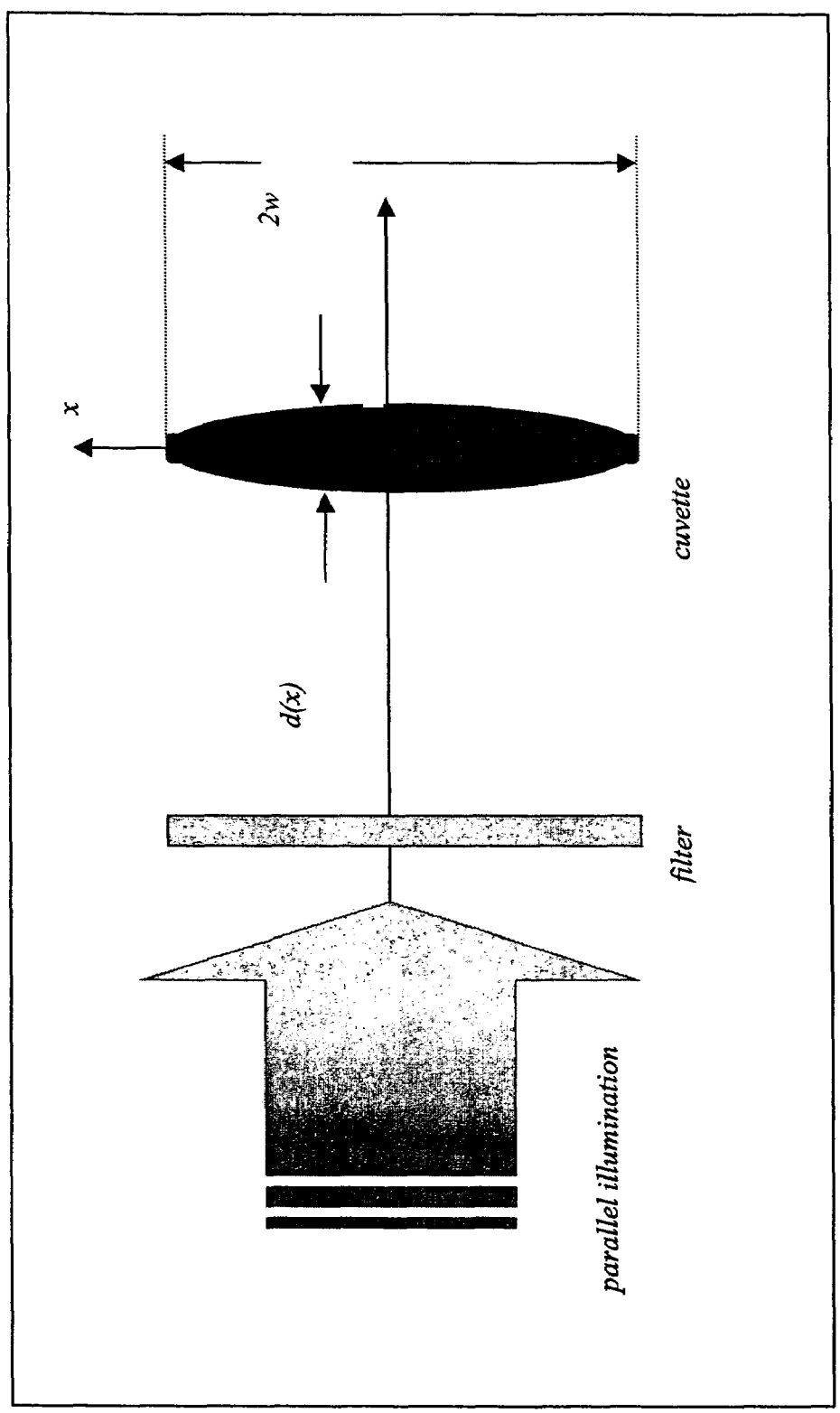
FIG. 23 schematically illustrates a water-filled non-parallel cuvette illuminated with parallel light that has passed through an optical filter with known bandwidth and filter shape.

FIG. 23 schematically illustrates a water-filled non-parallel cuvette illuminated with parallel light that has passed through an optical filter with known bandwidth and filter shape. In FIG. 23, the x-axis is perpendicular to the optic axis, the cuvette shape (path length as a function of x) is defined by the function d(x), and the cuvette width is 2w. The transmission through a filter for a water-filled non-parallel cuvette with parallel illumination can be expressed by the following relation:

$$\tau_n = \frac{1}{N_n} \cdot \frac{1}{2w} \int d\lambda f_n(\lambda) \int_{-w}^{w} dx \exp[-\alpha(\lambda)d(x)] \tag{20}$$

where $\alpha(\lambda)$=water absorption;
$f_n(\lambda)$=filter transmission;
$N_n$=filter normalization;
$d(x)$=cuvette path length; and
$2w$=cuvette width.

The filter normalization can be expressed by the following relation:

$$N_n = \int d\lambda f_n(\lambda), \tag{21}$$

and the path length across the cuvette can be expressed by the following relation:

$$d(x) = d_{avg} + \delta(x), \tag{22}$$

where d is the average path length and the following relation is true:

$$\int_{-w}^{w} dx \delta(x) = 0. \tag{23}$$

a. Expression of Integral Optical Density as Sum of Terms

In certain embodiments, the natural log optical density can be derived in the following manner. By substituting Equation (22) into Equation (20), the transmission can be expressed by the following relation:

$$\tau_n = \frac{1}{N_n} \cdot \frac{1}{2w} \int d\lambda f_n(\lambda) \exp[-\alpha(\lambda)d_{avg}] \int_{-w}^{w} dx \exp[-\alpha(\lambda)\delta(x)] \tag{24}$$

Using the following relations:

$$\Delta_n(\lambda) \equiv -\langle \alpha_n \rangle - \alpha(\lambda), \text{ and} \tag{25}$$

$$\langle \alpha_n \rangle \equiv \frac{1}{N_n} \int d\lambda \cdot f_n(\lambda) \cdot \alpha(\lambda), \tag{26}$$

the transmission can be expressed by the following relation:

$$\tau_n = \exp[-\langle \alpha_n \rangle d_{avg}] \frac{1}{N_n} \cdot \frac{1}{2w} \int d\lambda f_n(\lambda) \exp[-\Delta_n(\lambda)d_{avg}] \int_{-w}^{w} dx \exp[-\alpha(\lambda)\delta(x)], \tag{27}$$

which can be rewritten to be expressed by the following relation:

$$\tau_n = \exp[-\langle \alpha_n \rangle d_{avg}] \frac{1}{N_n} \int d\lambda f_n(\lambda) K(\lambda) \exp[-\Delta_n(\lambda)d_{avg}], \tag{28}$$

where $$K(\lambda) \equiv \frac{1}{2w} \int_{-w}^{w} dx \exp[-\alpha(\lambda)\delta(x)]. \tag{29}$$

Expanding the exponential of Equation (29) yields the following relation:

$$K(\lambda) \equiv \frac{1}{2w} \int_{-w}^{w} dx \left(1 - \alpha(\lambda)\delta(x) + \frac{1}{2}\alpha(\lambda)^2 \delta(x)^2 + h.o.t.\right). \tag{30}$$

The first integral is equal to one, the second integral is equal to zero, using Equation (23). Thus, $K(\lambda)$ can be expressed by the following relation:

$$K(\lambda) \equiv 1 + \frac{1}{2} \frac{1}{2w} \int_{-w}^{w} dx [\alpha(\lambda)^2 \delta(x)^2 + h.o.t.]. \tag{31}$$

The distortion parameter A can be defined by the following relation:

$$A \equiv \frac{1}{2}\frac{1}{2w}\int_{-w}^{w} dx \cdot \delta(x)^2, \quad (32)$$

and $K(\lambda)$ can be expressed by the following relation:

$$K(\lambda) = 1 + A\alpha(\lambda)^2 + h.o.t. \quad (33)$$

Neglecting the higher order terms and substituting Equation (33) into Equation (28), the transmission can be expressed by the following relation:

$$\tau_n = \exp[-\langle\alpha_n\rangle d_{avg}]\frac{1}{N_n}\int d\lambda f_n(\lambda)[1 + A\alpha(\lambda)^2]\exp[-\Delta_n(\lambda)d_{avg}]. \quad (34)$$

The transmission can be rewritten to be expressed by the following relation:

$$\tau_n = [J_1 + J_2]\exp[-\langle\alpha_n\rangle d_{avg}], \quad (35)$$

where:

$$J_1 = \frac{1}{N_n}\int d\lambda f_n(\lambda)\exp[-\Delta_n(\lambda)d_{avg}], \text{ and} \quad (36)$$

$$J_2 = \frac{A}{N_n}\int d\lambda f_n(\lambda)\alpha(\lambda)^2\exp[-\Delta_n(\lambda)d_{avg}]. \quad (37)$$

By expanding the exponential in the first integral and keeping terms up to $\Delta_n^2(\lambda)$, Equation (36) can be rewritten to be expressed by the following relation:

$$J_1 = \frac{1}{N_n}\int d_{avg}\lambda f_n(\lambda)\left[1 - \Delta_n(\lambda)d + \frac{1}{2}\Delta_n^2(\lambda)d_{avg}^2\right]. \quad (38)$$

Using Equations (25) and (26), the following relation can be written:

$$\int d\lambda f_n(\lambda)\Delta_n(\lambda) = 0, \quad (39)$$

and Equation (36) can be rewritten to be expressed by the following relation:

$$J_1 = 1 + \frac{d_{avg}^2}{2}\frac{1}{N_n}\int d\lambda f_n(\lambda)\Delta_n^2(\lambda). \quad (40)$$

The exponential in Equation (37) can be similarly expanded to be expressed by the following relation:

$$J_2 = \frac{A}{N_n}\int d_{avg}\lambda f_n(\lambda)\alpha(\lambda)^2\left[1 - \Delta_n(\lambda)d_{avg} + \frac{1}{2}\Delta_n^2(\lambda)d_{avg}^2\right]. \quad (41)$$

Using Equation (25), Equation (37) can be rewritten to be expressed by the following relation:

$$J_2 = \frac{A}{N_n}\int d_{avg}\lambda f_n(\lambda)[\langle\alpha_n\rangle - \Delta_n(\lambda)]^2\left[1 - \Delta_n(\lambda)d_{avg} + \frac{1}{2}\Delta_n^2(\lambda)d_{avg}^2\right], \quad (42)$$

which, by completing the square, can be expressed by the following relation:

$$J_2 = \frac{A}{N_n}\int d\lambda f_n(\lambda)[\langle\alpha_n\rangle^2 - 2\langle\alpha_n\rangle\Delta_n(\lambda) + \quad (43)$$

$$\Delta_n^2(\lambda)]\cdot\left[1 - \Delta_n(\lambda)d_{avg} + \frac{1}{2}\Delta_n^2(\lambda)d_{avg}^2\right].$$

Again, keeping terms up to order $\Delta_n^2(\lambda)$, $J_2$ can be expressed by the following relation:

$$J_2 = \frac{A}{N_n}\int d\lambda f_n(\lambda)\left[\langle\alpha_n\rangle^2 - (2\langle\alpha_n\rangle + \langle\alpha_n\rangle^2 d_{avg})\Delta_n(\lambda) + \quad (44)\right.$$

$$\left.\left(1 + 2\langle\alpha_n\rangle d_{avg} + \frac{1}{2}\langle\alpha_n\rangle^2 d_{avg}^2\right)\Delta_n^2(\lambda)\right],$$

which after completing the integration can be expressed by the following relation:

$$J_2 = A\langle\alpha_n\rangle^2 + \frac{A}{N_n}\left(1 - 2\langle\alpha_n\rangle d_{avg} + \frac{1}{2}\langle\alpha_n\rangle^2 d_{avg}^2\right)\int d\lambda f_n(\lambda)\Delta_n^2(\lambda). \quad (45)$$

The combination of Equations (40) and (45) can then be expressed by the following relation:

$$J_1 + J_2 = \quad (46)$$

$$1 + \frac{1}{2}d_{avg}^2 J_{3n} + A\langle\alpha_n\rangle^2 + \frac{A}{N_n}\left(1 - 2\langle\alpha_n\rangle d_{avg} + \frac{1}{2}\langle\alpha_n\rangle^2 d_{avg}^2\right)J_{3n},$$

where:

$$J_{3n} \equiv \frac{1}{N_n}\int d\lambda f_n(\lambda)\Delta_n^2(\lambda) = \frac{1}{N_n}\int d\lambda \cdot f(\lambda)\cdot(\alpha(\lambda) - \langle\alpha_n\rangle)^2, \quad (47)$$

which is the non-linear filter term.

Substituting Equation (46) into Equation (35) yields the following relation:

$$\tau_n = \left[1 + \frac{1}{2}d_{avg}^2 J_{3n} + A\langle\alpha_n\rangle^2 + A\left(1 - 2\langle\alpha_n\rangle d_{avg} + \frac{1}{2}\langle\alpha_n\rangle^2 d_{avg}^2\right)J_{3n}\right] \quad (48)$$

$$\exp[-\langle\alpha_n\rangle d_{avg}].$$

Taking the natural log of Equation (48), the optical density can be expressed by the following relation:

$$OD_n = -\ln(\tau_n) = \langle\alpha_n\rangle d_{avg} - \quad (49)$$

$$\ln\left[1 + \frac{1}{2}d_{avg}^2 J_{3n} + A\langle\alpha_n\rangle^2 + A\left(1 - 2\langle\alpha_n\rangle d_{avg} + \frac{1}{2}\langle\alpha_n\rangle^2 d_{avg}^2\right)J_{3n}\right],$$

Using the approximation: $\ln(1+\epsilon) \approx \epsilon$, the optical density can be expressed by the following relation:

$$OD_n = \langle \alpha_n \rangle d_{avg} - \frac{1}{2} d_{avg}^2 J_{3n} - A\langle \alpha_n \rangle^2 - AJ_{3n}\left(1 - 2\langle \alpha_n \rangle d_{avg} + \frac{1}{2}\langle \alpha_n \rangle^2 d_{avg}^2\right). \quad (50)$$

The first term on the right hand side of Equation (50) is equal to the average water absorption through the filter multiplied by the path length. The second term is a correction due to finite filter width and shape. The third term is a correction due to the cuvette shape, and the last term is a cross-term resulting from finite filter width and cuvette shape. Thus, for a water-filled cuvette irradiated by light transmitted through a filter "n," the optical density can be expressed as being equal to the average water absorption through the filter multiplied by the pathlength, plus a correction term due to the finite filter width and shape, plus a correction term due to the cuvette shape, and a cross-term resulting from finite filter width and cuvette shape. Equation (50) is preferably applied to a restricted range of cuvette shapes and filter widths. As the filters get wider and/or the cuvette shape variations larger, additional terms are preferably used. Simulations, using known properties of water, can be used to show that the terms in Equation (50) sufficiently model the conditions in a blood transmission apparatus.

2. Temperature Effects on Measured Optical Density

There are two primary temperature effects. First, the absorption of water is temperature-dependent. Second, the filter center wavelength shifts with temperature. Both of these effects cause temperature-dependent changes of the measured transmission. The temperature effects can be modeled by treating the filter transmission functions as fixed and adjusting the water absorption to account for the change in water temperature and shifting the water absorption to account for the filter temperature. The absorption as a function of temperature change can be expressed by the following relation:

$$\alpha_n(\lambda) = \alpha_o(\lambda) + \beta(\lambda)\Delta T_w + \gamma_n(\lambda)\Delta T_f + \xi_n(\lambda)\Delta T_w \Delta T_f \quad (51)$$

where $\alpha_o(\lambda)$=water absorption at $\Delta T_w = \Delta T_f = 0$, and $$\beta(\lambda) = \frac{\delta \alpha_o(\lambda)}{\delta T_w} = \text{absorption water temperature sensitivity,} \quad (52)$$

$$\gamma_n(\lambda) = \quad (53)$$
$$\frac{\delta \alpha_o(\lambda)}{\delta T_f} = \frac{\delta \alpha_o(\lambda)}{\delta \lambda} \cdot \frac{\delta \lambda_n}{\delta T_f} = \text{absorption filter temperature sensitivity,}$$

$$\xi_n(\lambda) = \frac{\delta^2 \alpha_o(\lambda)}{\delta T_w \delta T_f} = \quad (54)$$
$$\frac{\delta \beta(\lambda)}{\delta T_f} = \frac{\delta \beta(\lambda)}{d\lambda} \cdot \frac{d\lambda_n}{\delta T_f} = \text{cross-term or the change in } \beta(\lambda)$$

with filter temperature,
$\Delta T_w$=water temperature change,
$\Delta T_f$=filter temperature change, and $$\frac{d\lambda_n}{\delta T_f} = \text{filter "n" temperature sensitivity.}$$

Substituting Equation (51) into Equation (26) yields the following relation:

$$\langle \alpha_n \rangle = \langle \alpha_{on} \rangle + \langle \beta_n \rangle \Delta T_w + \langle \gamma_n \rangle \Delta T_f + \langle \xi_n \rangle \Delta T_w \Delta T_f, \quad (55)$$

where $N_n = \int d\lambda f_n(\lambda)$, and $$\langle q_n \rangle \equiv \frac{1}{N_n} \int d\lambda \cdot f_n(\lambda) \cdot q(\lambda), \quad (56)$$

which corresponds to the following relations:

$$\langle \alpha_{on} \rangle = \frac{1}{N_n} \int d\lambda \cdot f_n(\lambda) \cdot \alpha_o(\lambda), \quad (56.1)$$

$$\langle \beta_n \rangle = \frac{1}{N_n} \int d\lambda \cdot f_n(\lambda) \cdot \beta(\lambda), \quad (56.2)$$

$$\langle \gamma_n \rangle = \frac{1}{N_n} \int d\lambda \cdot f_n(\lambda) \cdot \gamma_n(\lambda), \text{ and} \quad (56.3)$$

$$\langle \xi_n \rangle = \frac{1}{N_n} \int d\lambda \cdot f_n(\lambda) \cdot \xi_n(\lambda). \quad (56.4)$$

Equation (50) can be expressed by the following relation:

$$OD_n = \langle \alpha_{on} \rangle d_{avg} + \langle \beta_n \rangle \Delta T_w d_{avg} + \langle \gamma_n \rangle \Delta T_f d_{avg} + (\alpha_n)^2 A + T_n, \quad (57)$$

where $$T_n = \quad (58)$$
$$\langle \xi_n \rangle \Delta T_w \Delta T_f d_{avg} - \frac{1}{2} d_{avg}^2 J_{3n} - AJ_{3n}\left(1 - 2\langle \alpha_n \rangle d_{avg} + \frac{1}{2}\langle \alpha_n \rangle^2 d_{avg}^2\right).$$

Thus, the optical density $OD_n$ can be expressed to include contributions to the measured absorption spectrum from changes in water temperature, changes in filter temperature, and a cross-term resulting from water and filter temperature changes.

E. Subtraction of System and Temperature Effects from Absorption Data

Figure 24:
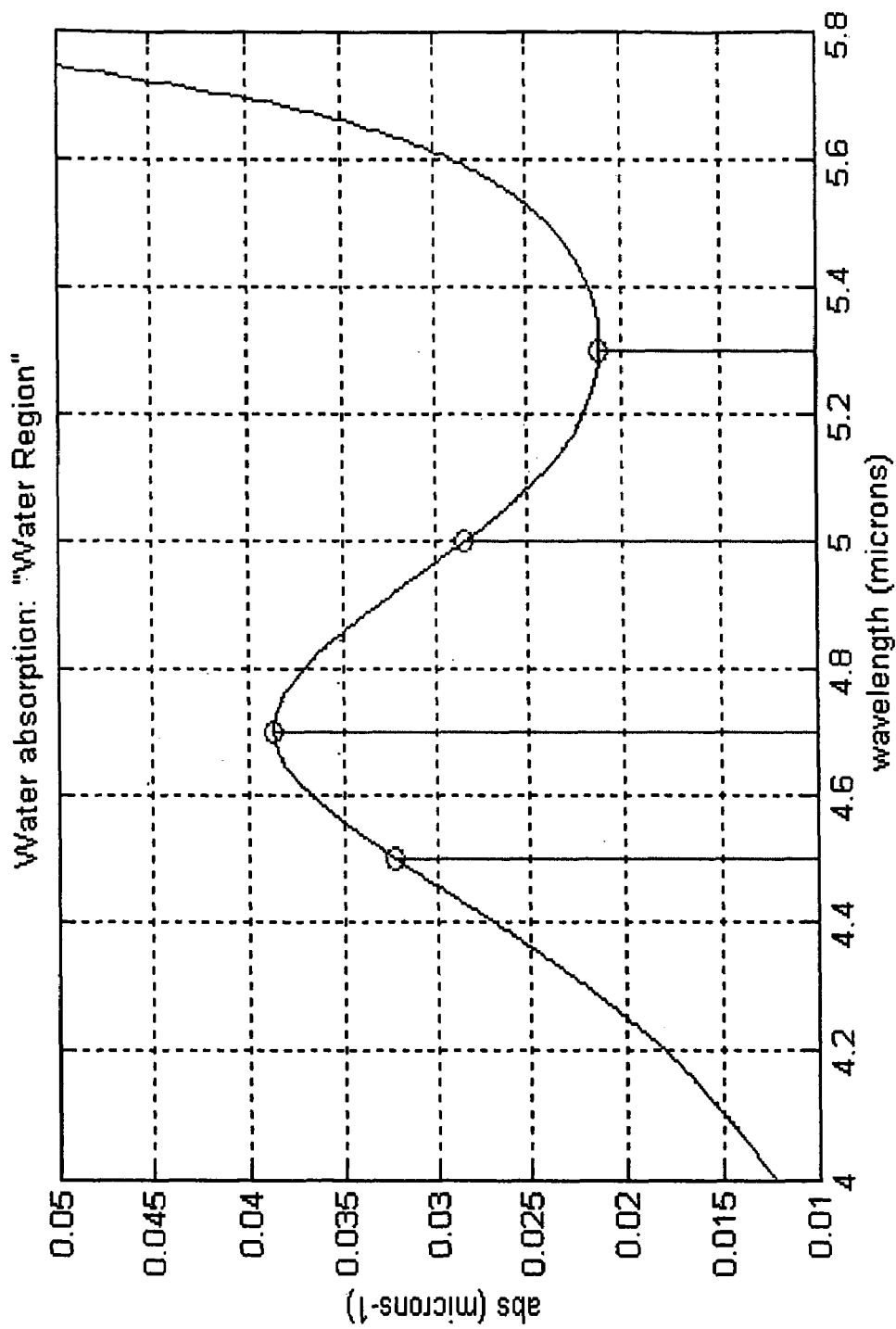
FIG. 24 illustrates the absorption of water in an exemplary water region.

FIG. 24 illustrates the absorption of water in an exemplary water region. The analysis of the absorption data preferably uses a finite number of absorption measurements (for example, at the wavelengths indicated in FIG. 24 by vertical lines) in this wavelength region to determine the path length, water temperature, filter temperature and cuvette shape.

In certain embodiments, the analysis utilizes four OD measurements which, assuming $T_n = 0$ and $\langle \alpha_n \rangle = \langle \alpha_{on} \rangle$, are expressed as a set of linear equations to be solved expressed by the following relation:

$$\begin{pmatrix} OD_1 \\ OD_2 \\ OD_3 \\ OD_4 \end{pmatrix} = \begin{pmatrix} \langle \alpha_{01} \rangle & \langle \beta_1 \rangle & \langle \gamma_1 \rangle & \langle \alpha_{01} \rangle^2 \\ \langle \alpha_{02} \rangle & \langle \beta_2 \rangle & \langle \gamma_2 \rangle & \langle \alpha_{02} \rangle^2 \\ \langle \alpha_{03} \rangle & \langle \beta_3 \rangle & \langle \gamma_3 \rangle & \langle \alpha_{03} \rangle^2 \\ \langle \alpha_{04} \rangle & \langle \beta_4 \rangle & \langle \gamma_4 \rangle & \langle \alpha_{04} \rangle^2 \end{pmatrix} \cdot \begin{pmatrix} d_{avg} \\ \Delta T_w d_{avg} \\ \Delta T_f d_{avg} \\ A \end{pmatrix}. \quad (59)$$

The solution of this set of linear equations can provide an initial estimate of the parameters ($d_{avg}$, $\Delta T_w$, $\Delta T_f$, A) which are used to evaluate the non-linear terms ($T_1 \ldots T_4$). The next estimate of $(d_{avg}, \Delta T_w, \Delta T_f, A)$ can be found by solving the following relation:

$$\begin{pmatrix} OD_1 - T_1 \\ OD_2 - T_2 \\ OD_3 - T_3 \\ OD_4 - T_4 \end{pmatrix} = \begin{pmatrix} \langle\alpha_{01}\rangle & \langle\beta_1\rangle & \langle\gamma_1\rangle & \langle\alpha_1\rangle^2 \\ \langle\alpha_{02}\rangle & \langle\beta_2\rangle & \langle\gamma_2\rangle & \langle\alpha_2\rangle^2 \\ \langle\alpha_{03}\rangle & \langle\beta_3\rangle & \langle\gamma_3\rangle & \langle\alpha_3\rangle^2 \\ \langle\alpha_{04}\rangle & \langle\beta_4\rangle & \langle\gamma_4\rangle & \langle\alpha_4\rangle^2 \end{pmatrix} \cdot \begin{pmatrix} d_{avg} \\ \Delta T_w d_{avg} \\ \Delta T_f d_{avg} \\ A \end{pmatrix}. \quad (60)$$

This process can be repeated until estimates of path length, water temperature, filter temperature and cuvette non-parallelism (i.e., the degree to which opposed walls/windows of the sample chamber deviate from parallel, which is referred to at times as "bowing") converge.

Measurements using this approach may not deliver the desired accuracy over the entire range of temperature and cuvette/sample chamber shape. Other approaches may be used to yield more stable results. One such alternative approach is based on rewriting Equations (57) and (58) to be expressed by the following relations:

$$OD_n = \quad (61)$$
$$\langle\alpha_{on}\rangle d_{avg} + \langle\beta_n\rangle \Delta T_w d_{avg} + \langle\gamma_n\rangle \Delta T_f d_{avg} + \langle\alpha_n\rangle^2 A - \frac{1}{2} d_{avg}^2 J_{3n} + S_n,$$

$$S_n = \langle\xi_n\rangle \Delta T_w \Delta T_f d_{avg} - A J_{3n}\left(1 - 2\langle\alpha_n\rangle d_{avg} + \frac{1}{2}\langle\alpha_n\rangle^2 d_{avg}^2\right). \quad (62)$$

Rearranging Equation (61) yields the following relation:

$$OD_n - d_{avg}\langle\alpha_{on}\rangle + \frac{1}{2} d_{avg}^2 J_{3n} - S_n = \quad (63)$$
$$d_{avg}\langle\beta_n\rangle \Delta T_w + d_{avg}\langle\gamma_n\rangle \Delta T_f + \langle\alpha_n\rangle^2 A.$$

Embodiments in which Equation (63) is used to analyze the absorption data are described below.

1. Water Temperature, Filter Temperature, Cuvette Shape Analysis

In certain embodiments, the water temperature, filter temperature, and cuvette shape are analyzed. In such embodiments, the analysis comprises "step 1" in which transmission measurements, filter parameters and water spectral properties are inputted:

Transmission measurements $(\tau_1, \tau_2, \tau_3, \tau_4)$,
Filter curves $[f_1(\lambda), f_2(\lambda), f_3(\lambda), f_4(\lambda)]$,
Filter temperature sensitivities $$\left[\frac{d\lambda_1}{\delta T_f}, \frac{d\lambda_2}{\delta T_f}, \frac{d\lambda_3}{\delta T_f}, \frac{d\lambda_4}{\delta T_f}\right],$$

and
Water spectral properties $$\left[\alpha_o(\lambda), \beta(\lambda), \frac{\delta\alpha_o(\lambda)}{\delta\lambda}, \frac{\delta\beta(\lambda)}{\delta\lambda}\right].$$

Certain embodiments of the analysis further comprise "step 2" in which optical densities and filter constants are calculated:

$$OD_n = -\ln(\tau_n),$$

$$\langle\alpha_{on}\rangle = \frac{1}{N_n}\int d\lambda \cdot f_n(\lambda) \cdot \alpha_o(\lambda),$$

$$\langle\beta_n\rangle = \frac{1}{N_n}\int d\lambda \cdot f_n(\lambda) \cdot \beta(\lambda),$$

$$\langle\gamma_n\rangle = \frac{1}{N_n}\int d\lambda \cdot f_n(\lambda) \cdot \frac{\delta\alpha_o(\lambda)}{\delta\lambda} \cdot \frac{d\lambda_n}{\delta T_f}, \text{ and}$$

$$\langle\xi_n\rangle = \frac{1}{N_n}\int d\lambda \cdot f_n(\lambda) \cdot \frac{\delta\beta(\lambda)}{\delta\lambda} \cdot \frac{d\lambda_n}{\delta T_f}.$$

In certain embodiments, the analysis further comprises "step 3" in which the non-linear filter terms and cuvette distortion matrix element are estimated using the following relations:

$$J_{3n} = \frac{1}{N_n}\int d\lambda \cdot f(\lambda) \cdot (\alpha(\lambda) - \langle\alpha_o\rangle)^2,$$

$$\langle\alpha_n\rangle^2 = \langle\alpha_{on}\rangle^2, \text{ and}$$

$$S_n = 0.$$

In certain embodiments, the analysis further comprises "step 4" in which the analysis solves for $(\Delta T_w, \Delta T_f, A)$ as a function of path length d using $(OD_1, OD_2, OD_3)$ and $(OD_2, OD_3, OD_4)$. The values of $(d_{avg}, \Delta T_w, \Delta T_f, A)$ are estimated by finding value of d where solutions for $(\Delta T_w, \Delta T_f, A)$ are same for both sets of transmission measurements:

$$\begin{pmatrix} OD_1 - d\langle\alpha_{o1}\rangle + \frac{1}{2}d^2 J_{31} - S_1 \\ OD_2 - d\langle\alpha_{o2}\rangle + \frac{1}{2}d^2 J_{32} - S_2 \\ OD_3 - d\langle\alpha_{o3}\rangle + \frac{1}{2}d^2 J_{33} - S_3 \end{pmatrix} = \begin{pmatrix} d\langle\beta_1\rangle & d\langle\gamma_1\rangle & \langle\alpha_1\rangle^2 \\ d\langle\beta_2\rangle & d\langle\gamma_2\rangle & \langle\alpha_2\rangle^2 \\ d\langle\beta_3\rangle & d\langle\gamma_3\rangle & \langle\alpha_3\rangle^2 \end{pmatrix} \cdot \begin{pmatrix} \Delta T_w \\ \Delta T_f \\ A \end{pmatrix},$$

and $$\begin{pmatrix} OD_2 - d\langle\alpha_{o2}\rangle + \frac{1}{2}d^2 J_{32} - S_2 \\ OD_3 - d\langle\alpha_{o3}\rangle + \frac{1}{2}d^2 J_{33} - S_3 \\ OD_4 - d\langle\alpha_{o4}\rangle + \frac{1}{2}d^2 J_{34} - S_4 \end{pmatrix} = \begin{pmatrix} d\langle\beta_2\rangle & d\langle\gamma_2\rangle & \langle\alpha_2\rangle^2 \\ d\langle\beta_3\rangle & d\langle\gamma_3\rangle & \langle\alpha_3\rangle^2 \\ d\langle\beta_4\rangle & d\langle\gamma_4\rangle & \langle\alpha_4\rangle^2 \end{pmatrix} \cdot \begin{pmatrix} \Delta T_w \\ \Delta T_f \\ A \end{pmatrix}.$$

In certain embodiments, the analysis further comprises "step 5" in which new estimates of absorption and non-linear terms are calculated:

$$\langle\alpha_n\rangle = \langle\alpha_{on}\rangle + \langle\beta_n\rangle \Delta T_w + \langle\gamma_n\rangle \Delta T_f + \langle\xi_n\rangle \Delta T_w \Delta T_f,$$

$$J_{3n} = \frac{1}{N_n}\int d\lambda \cdot f(\lambda) \cdot (\alpha(\lambda) - \langle\alpha_n\rangle)^2, \text{ and}$$

$$S_n = \langle\xi_n\rangle \Delta T_w \Delta T_f d - A J_{3n}\left(1 - 2\langle\alpha_n\rangle d + \frac{1}{2}\langle\alpha_n\rangle^2 d^2\right).$$

In certain embodiments, the analysis further comprises "step 6" in which "step 4" and "step 5" are repeated until the solution converges to a desired accuracy.

2. Water Temperature, Filter Temperature, Parallel Cuvette Analysis

In certain embodiments, the water temperature and filter temperature are analyzed for a parallel cuvette (i.e., one in which opposed walls of the sample chamber are substantially parallel). In such embodiments, the analysis comprises "step 1" in which transmission measurements, filter parameters and water spectral properties are inputted:

Transmission measurements ($\tau_1$, $\tau_2$, $\tau_3$),

Filter curves [$f_1(\lambda)$, $f_2(\lambda)$, $f_3(\lambda)$],

Filter temperature sensitivity $$\left[\frac{d\lambda_1}{\delta T_f}, \frac{d\lambda_2}{\delta T_f}, \frac{d\lambda_3}{\delta T_f}\right],$$

and

Water spectral properties $$\left[\alpha_o(\lambda), \beta(\lambda), \frac{\delta\alpha_o(\lambda)}{\delta\lambda}, \frac{\delta\beta(\lambda)}{\delta\lambda}\right].$$

Certain embodiments of the analysis further comprise "step 2" in which optical densities and filter constants are calculated:

$$OD_n = -\ln(\tau_n),$$

$$\langle\alpha_{on}\rangle = \frac{1}{N_n}\int d\lambda \cdot f_n(\lambda) \cdot \alpha_o(\lambda),$$

$$\langle\beta_n\rangle = \frac{1}{N_n}\int d\lambda \cdot f_n(\lambda) \cdot \beta(\lambda),$$

$$\langle\gamma_n\rangle = \frac{1}{N_n}\int d\lambda \cdot f_n(\lambda) \cdot \frac{\delta\alpha_o(\lambda)}{\delta\lambda} \cdot \frac{d\lambda_n}{\delta T_f}, \text{ and}$$

$$\langle\xi_n\rangle = \frac{1}{N_n}\int d\lambda \cdot f_n(\lambda) \cdot \frac{\delta\beta(\lambda)}{\delta\lambda} \cdot \frac{d\lambda_n}{\delta T_f}.$$

In certain embodiments, the analysis further comprises "step 3" in which the non-linear filter terms and cuvette distortion matrix element are estimated using the following relations:

$$J_{3n} = \frac{1}{N_n}\int d\lambda \cdot f(\lambda) \cdot (\alpha(\lambda) - \langle\alpha_o\rangle)^2,$$

$(\alpha_n)^2 = (\alpha_{on})^2$, and $S_n = 0$.

In certain embodiments, the analysis further comprises "step 4" in which the analysis solves for ($\Delta T_w$, $\Delta T_f$) as a function of path length d using ($OD_1$, $OD_2$) and ($OD_2$, $O_3$). The values of ($d_{avg}$, $\Delta T_w$, $\Delta T_f$) are estimated by finding value of d where solutions for ($\Delta T_w$, $\Delta T_f$) are the same for both sets of transmission measurements:

$$\begin{pmatrix} OD_1 - d\langle\alpha_{o1}\rangle + \frac{1}{2}d^2 J_{31} - S_1 \\ OD_2 - d\langle\alpha_{o2}\rangle + \frac{1}{2}d^2 J_{32} - S_2 \end{pmatrix} = \begin{pmatrix} d\langle\beta_1\rangle & d\langle\gamma_1\rangle \\ d\langle\beta_2\rangle & d\langle\gamma_2\rangle \end{pmatrix} \cdot \begin{pmatrix} \Delta T_w \\ \Delta T_f \end{pmatrix}, \text{ and}$$

$$\begin{pmatrix} OD_2 - d\langle\alpha_{o2}\rangle + \frac{1}{2}d^2 J_{32} - S_2 \\ OD_3 - d\langle\alpha_{o3}\rangle + \frac{1}{2}d^2 J_{33} - S_3 \end{pmatrix} = \begin{pmatrix} d\langle\beta_2\rangle & d\langle\gamma_2\rangle \\ d\langle\beta_3\rangle & d\langle\gamma_3\rangle \end{pmatrix} \cdot \begin{pmatrix} \Delta T_w \\ \Delta T_f \end{pmatrix}.$$

In certain embodiments, the analysis further comprises "step 5" in which new estimates of absorption and non-linear terms are calculated:

$$\langle\alpha_n\rangle = \langle\alpha_{on}\rangle + \langle\beta_n\rangle\Delta T_f + \langle\gamma_n\rangle\Delta T_f + \langle\xi_n\rangle\Delta T_w \Delta T_f,$$

$$J_{3n} = \frac{1}{N_n}\int d\lambda \cdot f(\lambda) \cdot (\alpha(\lambda) - \langle\alpha_n\rangle)^2, \text{ and}$$

$$S_n = \langle\xi_n\rangle\Delta T_w \Delta T_f d - AJ_{3n}\left(1 - 2\langle\alpha_n\rangle d + \frac{1}{2}\langle\alpha_n\rangle^2 d^2\right).$$

In certain embodiments, the analysis further comprises "step 6" in which "step 4" and "step 5" are repeated until the solution converges to a desired accuracy.

F. Contribution to Analyte Concentration Errors by Instrument Factors

Transmission data measured at each wavelength by certain apparatuses are typically affected by a combination of instrument factors and blood properties. The instrument factors include, but are not limited to, filter temperature, cuvette shape, filter characteristics (e.g., center wavelengths, temperature sensitivity, bandwidth, shape), and detector and source drift. The blood properties include, but are not limited to, blood temperature, the relative concentrations of the blood components and scattering. Before the transmission data are used to calculate analyte (e.g., glucose) concentration, the instrument factors are preferably determined and corresponding corrections are preferably made for each transmission value. As described above in relation to transmission measurements, each of the instrument factors can influence the transmission of a water-filled cuvette. In certain embodiments, the analysis can predict the analyte concentration error introduced by the instrument factors over the expected variation range for the apparatus.

Figure 25:
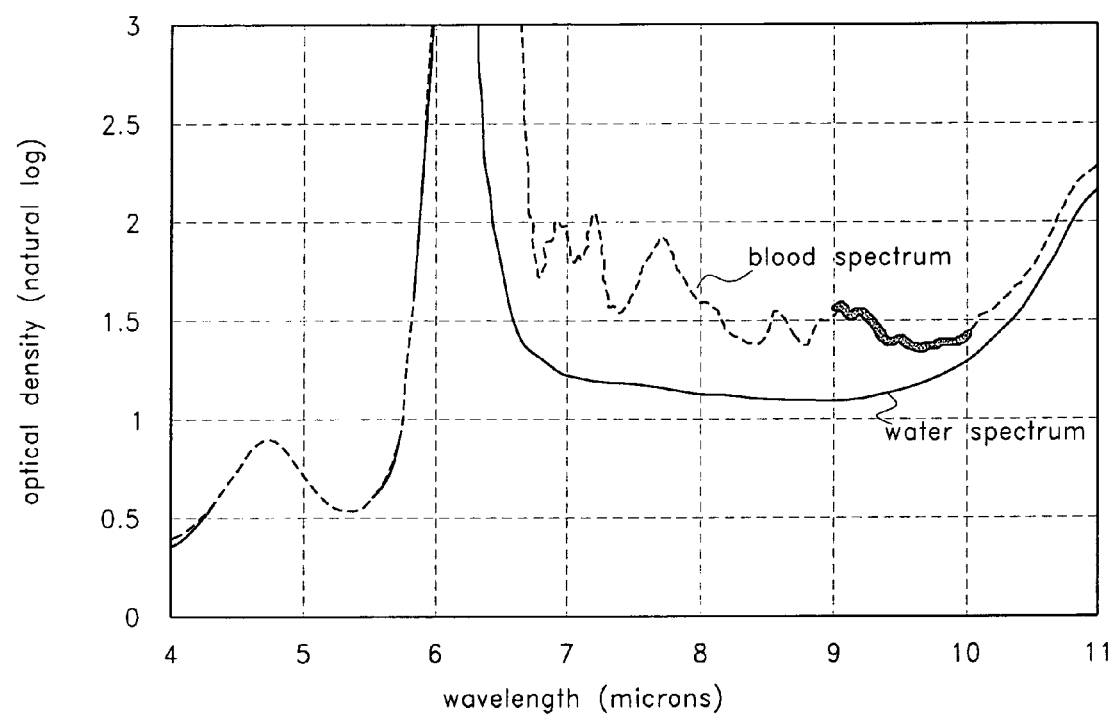
FIG. 25 illustrates an exemplary OD spectrum from a blood sample overlaid with a water reference spectrum in the wavelength range of 4 microns to 11 microns.

As described above, transmission measurements in the "water region" of wavelengths can be used to determine the blood's water content without considering other blood constituents. Once the water content is known, in certain embodiments, the water contribution at each of the wavelengths outside the water region can be calculated and removed. FIG. 25 illustrates an exemplary OD spectrum from a blood sample overlaid with a water reference spectrum in the wavelength range of 4 microns to 11 microns. As shown in FIG. 25, the water reference spectrum can be fitted to approximate the blood spectrum in a wavelength range of approximately 4.7 microns to approximately 5.3 microns. The fitted water spectrum can then be subtracted from the blood spectrum to produce an effectively water-free spectrum.

In certain transmission measurement systems, the filters have finite width and shape, the cuvettes may or may not be parallel, and the temperatures of the blood and filters may not be controlled. These factors will cause transmission changes that are not due to blood component changes or path length changes. If they are not corrected, the analysis can have corresponding errors in the calculated analyte concentration (e.g., glucose errors). While each of these instrument factors in isolation can result in a corresponding glucose error, in actual systems, the glucose error will be due to a combination of all the instrument factors.

Figure 26:
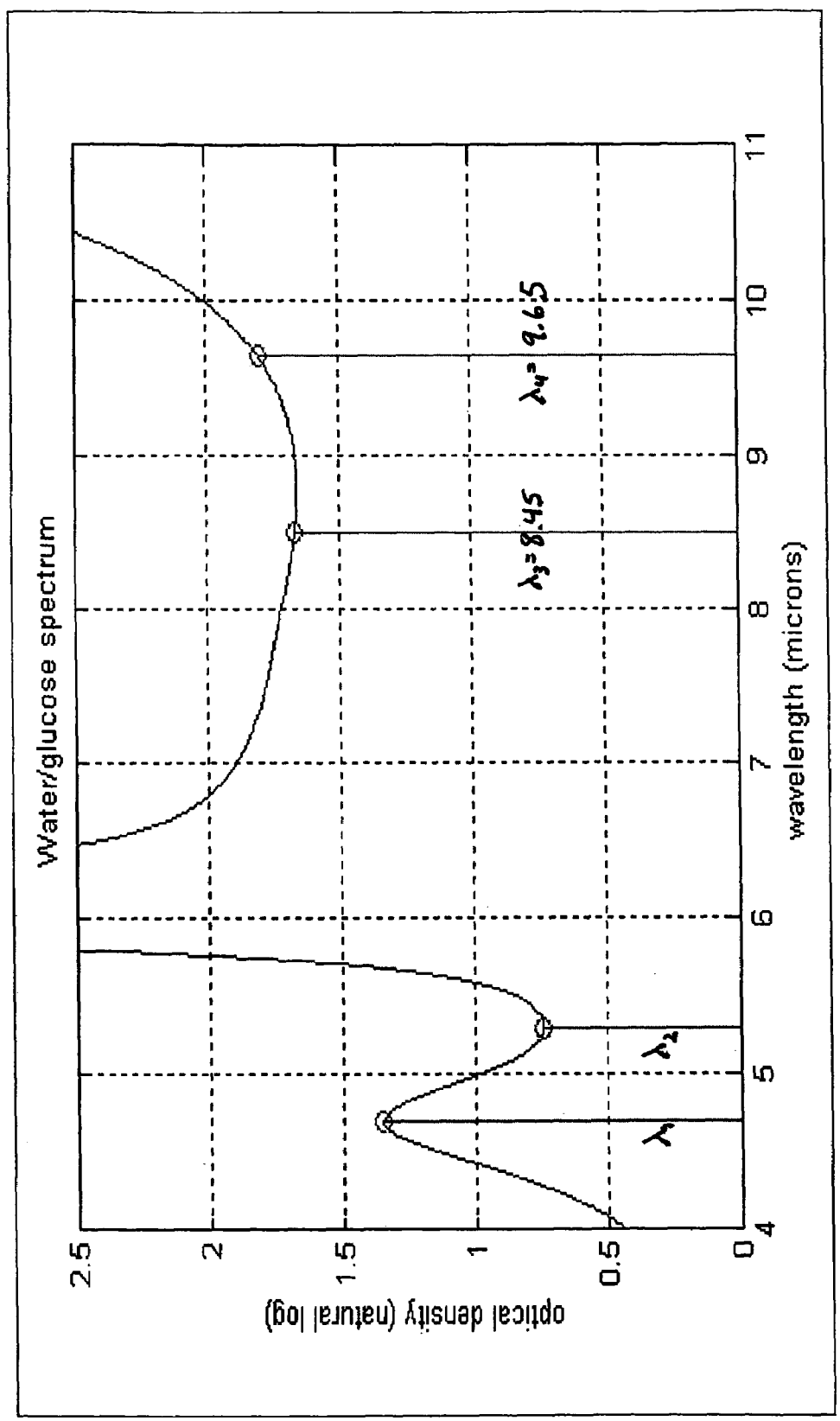
FIG. 26 illustrates an exemplary water OD spectrum showing four wavelengths used for determining the individual effects of various instrument factors.

In certain embodiments, the analysis described above can be used to estimate the magnitude of the glucose error for each instrument factor. The analysis can predict the optical density as a function of cuvette shape, filter shape, water temperature and filter temperature for a water-filled cuvette. The glucose error can be evaluated using four wavelengths, as illustrated in FIG. 26. The vertical lines of FIG. 26 denote these four wavelengths, two in the water region, one at a glucose reference wavelength (e.g., 8.45 microns) and one at the peak of the glucose absorption (e.g., 9.65 microns). The effects of each instrument factor can be studied separately.

In certain embodiments, a method of evaluating the glucose error comprises calculating the transmission and optical density ($od_1$, $od_2$, $od_3$, $od_4$) at each wavelength for a water-filled cuvette with instrument factor under study. The method further comprises using the optical density of the two water measurements ($od_1$, $od_2$) to determine the water content at the glucose reference and measurement wavelengths ($\lambda_3$, $\lambda_4$). The method further comprises calculating the expected optical density ($OD_{3c}$, $OD_{4c}$) at the glucose reference and measurement wavelengths. The method further comprises calculating residuals ($\Delta OD_3$, $\Delta OD_4$), which are the difference between the exact and calculated optical densities at the glucose reference and measurement wavelengths. The method further comprises determining the glucose error by calculating the glucose concentration consistent with residual difference ($\Delta OD_4 - \Delta OD_3$).

As described above, the transmission through a filter for a water-filled non-parallel cuvette with parallel illumination (e.g., exposed to a substantially cylindrical energy beam) can be expressed by Equation (20), and the corresponding optical density can be expressed by the following relation:

$$od_n = -\ln(\tau_n) \tag{64}$$

$$= -\ln\left[\frac{1}{N_n} \cdot \frac{1}{2w} \int d\lambda f_n(\lambda) \int_{-w}^{w} dx \exp[-\alpha_n(\lambda)d(x)]\right],$$

where $f_n(\lambda)$=filter transmission, $N_n$=filter normalization, $d(x)$=cuvette path length, $\Delta T_w$=water temperature change, $\Delta T_f$=filter temperature change, and $2w$=cuvette width.

As used herein, the above relation is referred to as the "exact optical density" because it does not include the various approximations described herein.

As described above, the water absorption adjusted for water and filter temperature can be expressed by Equation (51). An approximate solution for the optical density can be expressed by the following relations:

$$OD_n = \langle\alpha_{on}\rangle d_{avg} + \Delta OD_n, \text{ and} \tag{65}$$

$$\Delta OD_n = -\frac{1}{2}d_{avg}^2 J_{3n} + \langle\beta_n\rangle \Delta T_w d_{avg} + \tag{66}$$

$$\langle\gamma_n\rangle \Delta T_f d_{avg} + \langle\alpha_n\rangle^2 A + S_n,$$

where $d_{avg}$=average cuvette path length and $d(x)=d_{avg} \rightarrow A=0$. In Equations (64), (65), and (66), four instrument factors are specified by the following parameters:

$f_n(\lambda)$=filter function, $\Delta T_w$=water temperature change from nominal, $\Delta T_f$=filter temperature change from nominal, $d(x)$=cuvette shape.

In addition, the average absorption through the filter is represented by $\langle\alpha_{on}\rangle$ and $\Delta OD_n$ represents the effects due to water temperature, filter temperature, filter shape and cuvette shape.

1. Calculation of the Analyte Contribution Errors

The first four terms in Equation (66) represent the contributions of the instrument factors to the optical density. Considering each instrument factor separately, $\Delta OD_n$ becomes a function only of that factor. This allows the calculation of the glucose sensitivity for each factor and the evaluation of the accuracy of the approximate solution for the optical density as compared to the exact optical density. Table 2 shows the values of each of the four instrument factors for various simulations. Each row shows the values of the instrument factors for a particular simulation and the corresponding value of $\Delta OD_n$. The filter shape $\delta(\lambda_n)$ is a delta function representing an infinitely narrow filter at $\lambda_n$.

TABLE 2

|  | $f_n(\lambda)$ | $\Delta T_w$ | $\Delta T_f$ | $d(x)$ | $\Delta OD_n$ |
|---|---|---|---|---|---|
| Filter shape | $f_n(\lambda)$ | 0 | 0 | $d_{avg}$ | $-\frac{1}{2}d_{avg}^2 J_{3n}$ |
| Water temp | $\delta(\lambda_n)$ | $\Delta T_w$ | 0 | $d_{avg}$ | $\langle\beta_n\rangle \Delta T_w d_{avg}$ |
| Filter temp | $\delta(\lambda_n)$ | 0 | $\Delta T_f$ | $d_{avg}$ | $\langle\gamma_n\rangle \Delta T_f d_{avg}$ |
| Cuvette shape | $\delta(\lambda_n)$ | 0 | 0 | $d_{avg} + \epsilon(x)$ | $\langle\alpha_n\rangle^2 A$ |

Each simulation starts by calculating the set of exact optical densities [$od_1$, $od_2$, $od_3$, $od_4$] using Equation (64) and the instrument factors from Table 2. For all simulations, the calibration constants are the set [$\langle\alpha_{01}\rangle$, $\langle\alpha_{02}\rangle$, $\langle\alpha_{03}\rangle$, $\langle\alpha_{04}\rangle$], the form of which is expressed in Equation (56.1), and the predicted optical densities are expressed in Equation (65).

For the uncorrected case, the calculated path length ($d_c$) can be expressed using the exact optical densities from the water region and the calibration constants in the following relation:

$$d_c = \frac{od_2 - od_1}{\langle\alpha_{02}\rangle - \langle\alpha_{01}\rangle}. \tag{67}$$

The second two calibration constants can be used to predict the optical densities at ($\lambda_3$, $\lambda_4$) as follows:

$$OD_{3c} = \langle\alpha_{o3}\rangle \cdot d_c, \text{ and} \tag{68}$$

$$OD_{4c} = \langle\alpha_{o4}\rangle \cdot d_c. \tag{69}$$

The residuals can be expressed by the following relations:

$$\Delta OD_3 = OD_{3c} - od_3, \text{ and} \tag{70}$$

$$\Delta OD_4 = OD_{4c} - od_4. \tag{71}$$

The glucose error can be expressed by the following relation:

$$\Delta c_g = \frac{\Delta OD_4 - \Delta OD_3}{\Delta g_4 - \Delta g_3} \cdot \frac{1}{d_c}, \quad (72)$$

where ($\Delta g_3$, $\Delta g_4$) represents the glucose absorption at ($\lambda_3$, $\lambda_4$).

The glucose error for the corrected case can be determined by making the following transformation:

$$od_n \rightarrow od_n - \Delta OD_n, \quad (73)$$

and repeating the steps outlined in Equations (65) through (72). The corrected glucose error is a measure of how accurately the approximate optical densities given by Equation (65) equal the exact optical densities given by Equation (64). It is an indication of the range over which the instrument parameter (in this case filter width) can vary and still be predicted by the approximate equation.

2. Results

Graphs of the uncorrected and corrected glucose error as a function of cuvette shape parameters, path length, water temperature variation from nominal, and filter temperature from nominal can be generated using the method described above. The relative contributions of the various cuvette shape parameters can be compared to determine which parameters have the larger effect on the resultant glucose error. This analysis can demonstrate which sensitivities provide glucose errors which are too large unless corrected for. This analysis underestimates the corrected errors since it does not include cross terms when two or more factors are present. This analysis can also show whether the approximate optical density expansion agrees with the exact integral solution, that is, whether the higher order terms are needed.

a. Cuvette Shape Sensitivity

Figure 27:
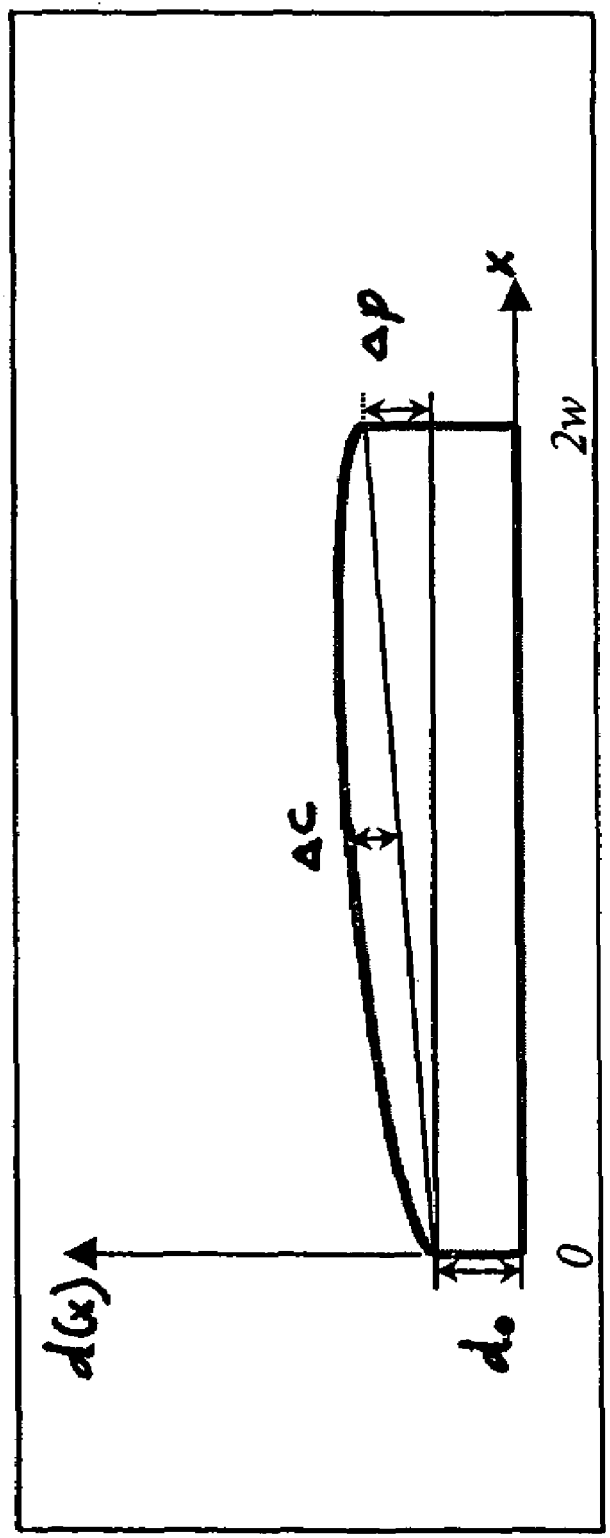
FIG. 27 schematically illustrates a model of the cuvette shape.

FIG. 27 schematically illustrates a model of the cuvette shape, which can model the bowing of the cuvette, which can be used in the analysis. In the model, the curvature ($\Delta c$) and wedge ($\Delta p$) are introduced to a parallel cuvette having a path length ($d_o$). The curvature is shown as being on one side of the cuvette, but the sensitivity is the same as if the same curvature is distributed between the top and bottom surfaces. The cuvette width is 2w. Other cuvette shapes may also be modeled.

Figure 28:
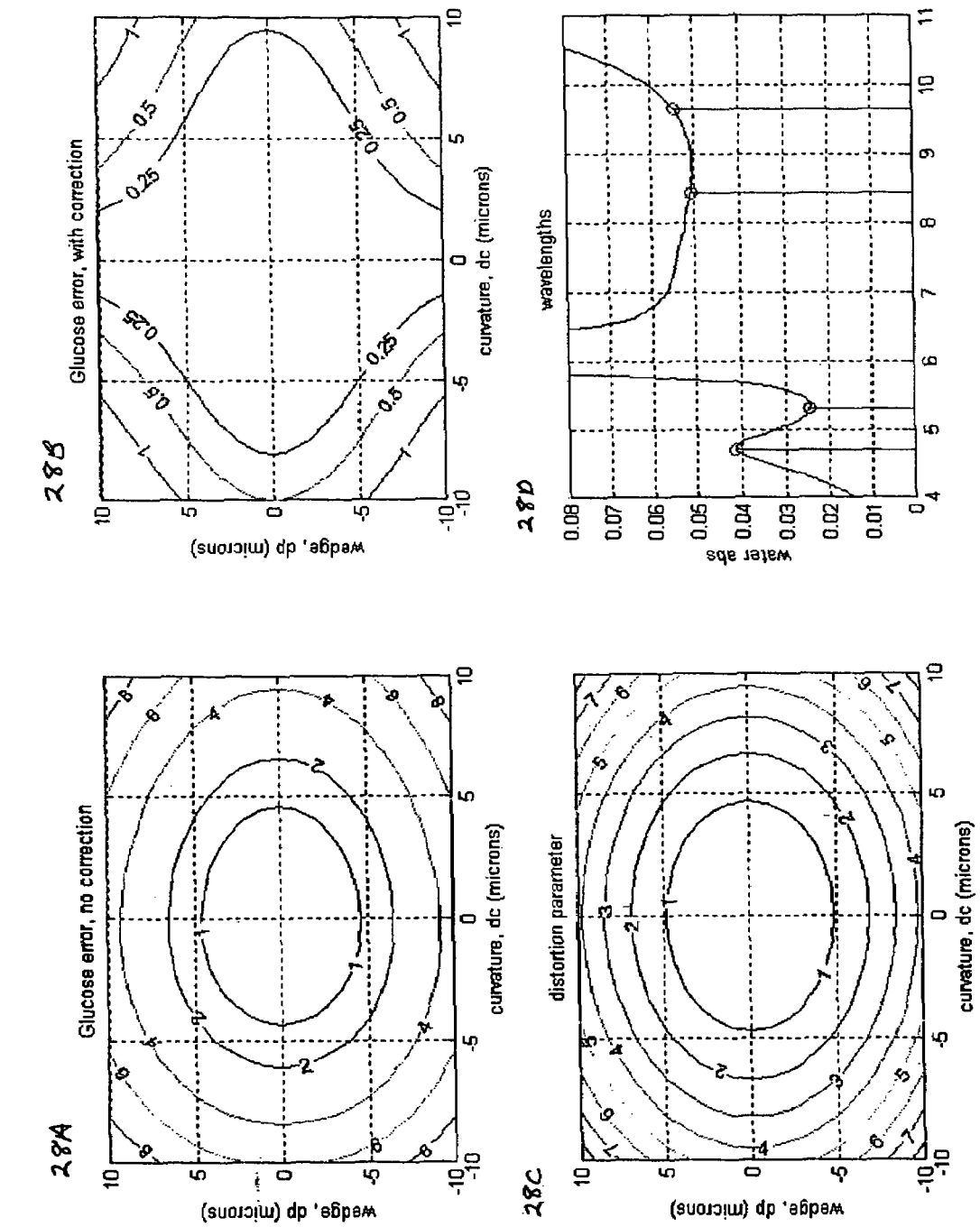
FIGS. 28A and 28B are graphs of the uncorrected and corrected glucose error, respectively, as a function of cuvette shape parameters for a first set of wavelengths.
FIG. 28C is a graph of the distortion parameter corresponding to FIGS. 28A and 28B.
FIG. 28D is a graph of the absorption spectrum with the first set of wavelengths used in the calculation denoted by vertical lines.

FIGS. 28A and 28B are graphs of the uncorrected and corrected glucose error, respectively, as a function of cuvette shape parameters for a first set of wavelengths. FIG. 28C is a graph of the distortion parameter corresponding to FIGS. 28A and 28B. FIG. 28D is a graph of the absorption spectrum with the first set of wavelengths used in the calculation denoted by vertical lines.

Figure 29:
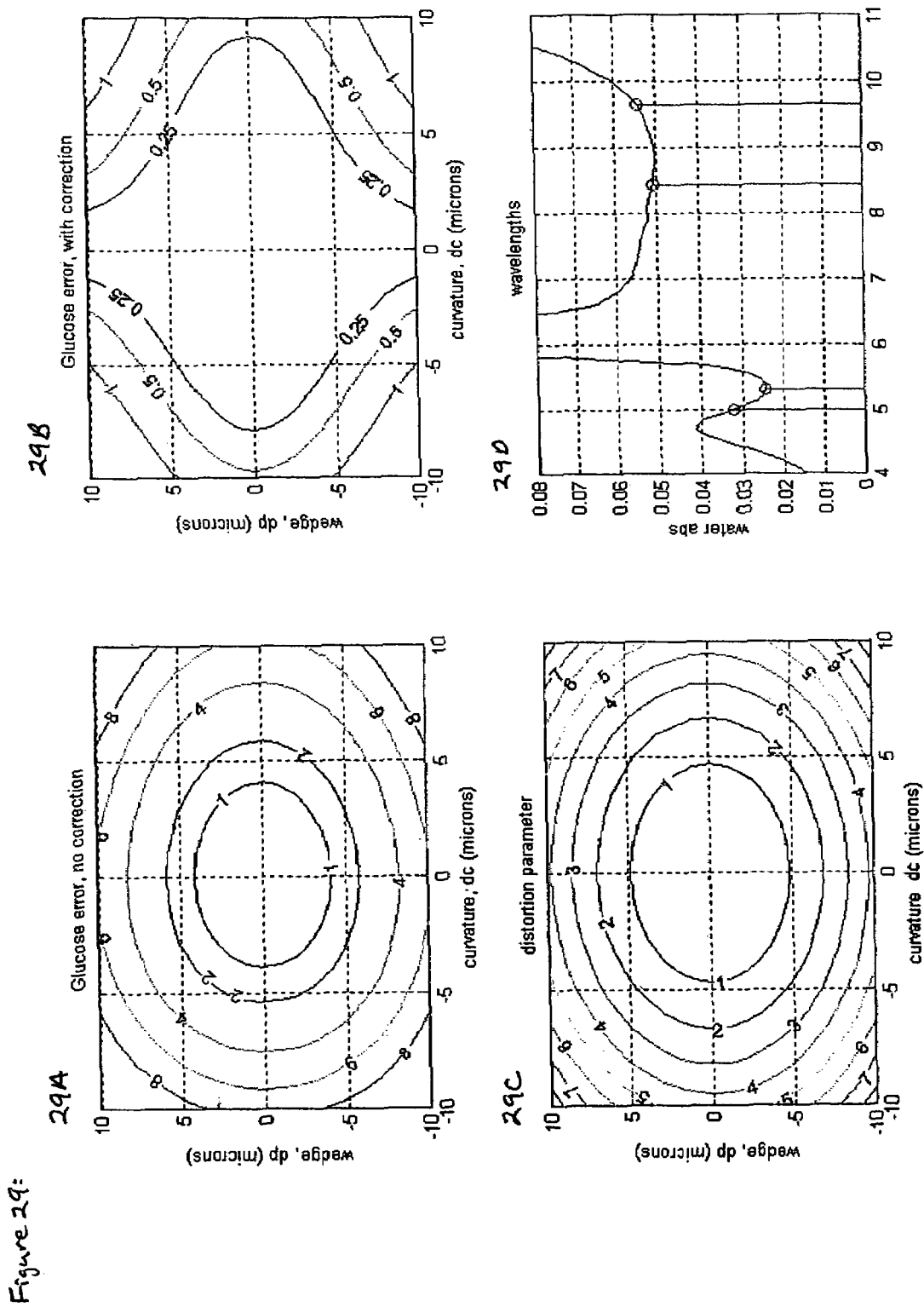
FIGS. 29A and 29B are graphs of the uncorrected and corrected glucose error, respectively, as a function of cuvette shape parameters for a first set of wavelengths.
FIG. 29C is a graph of the distortion parameter corresponding to FIGS. 29A and 29B.
FIG. 29D is a graph of the absorption spectrum with the first set of wavelengths used in the calculation denoted by vertical lines.

FIGS. 29A and 29B are graphs of the uncorrected and corrected glucose error, respectively, as a function of cuvette shape parameters for a second set of wavelengths. FIG. 29C is a graph of the distortion parameter corresponding to FIGS. 29A and 29B. FIG. 29D is a graph of the absorption spectrum with the second set of wavelengths used in the calculation denoted by vertical lines.

b. Filter Shape Sensitivity

Figure 30A:
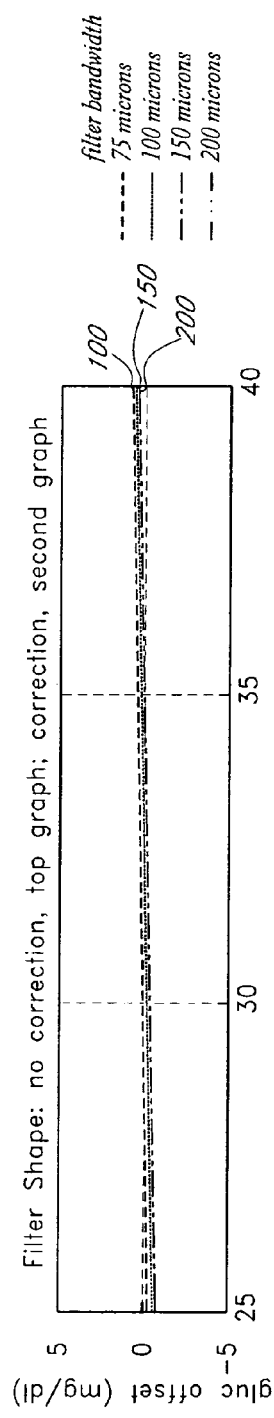
FIGS. 30A and 30B are graphs of the uncorrected and corrected glucose error, respectively, as a function of path length for different filter bandwidths for a first set of wavelengths.
Figure 30B:
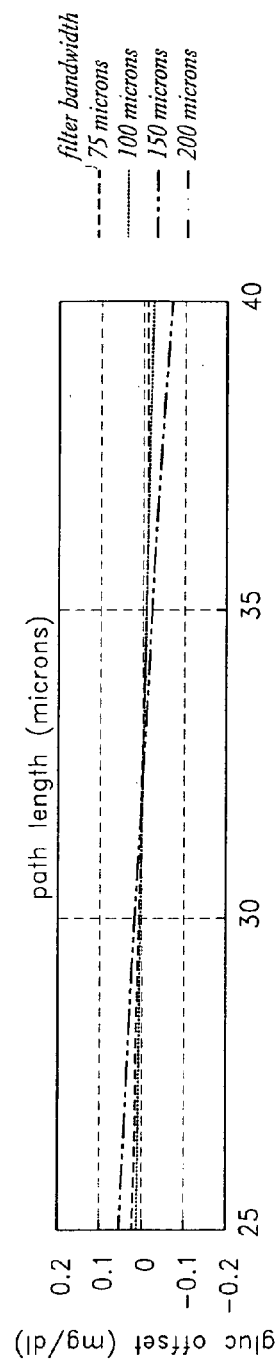
Figure 30C:
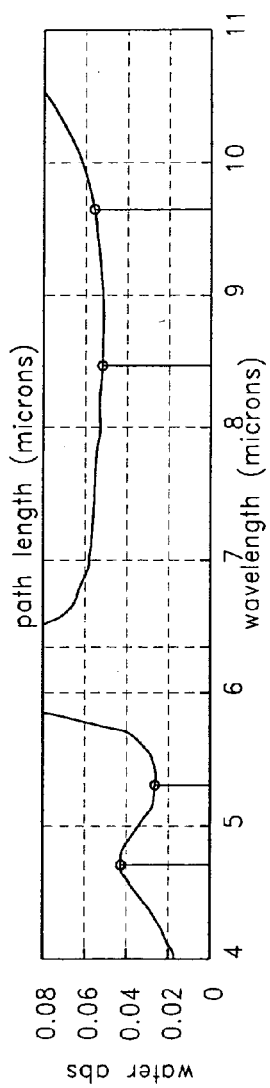
FIG. 30C is a graph of the absorption spectrum with the first set of wavelengths used in the calculation denoted by vertical lines.

FIGS. 30A and 30B are graphs of the uncorrected and corrected glucose error, respectively, as a function of path length for different filter bandwidths for a first set of wavelengths. FIG. 30C is a graph of the absorption spectrum with the first set of wavelengths used in the calculation denoted by vertical lines. In the calculation, each wavelength had identical gaussian-shaped filters with the filter bandwidth equal to the full-width-half-maximum (FWHM).

Figure 31A:
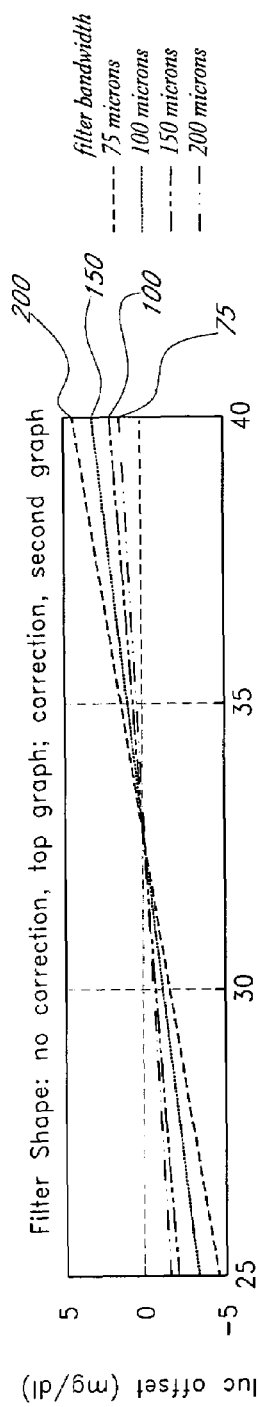
FIGS. 31A and 31B are graphs of the uncorrected and corrected glucose error, respectively, as a function of path length for different filter bandwidths for a second set of wavelengths.
Figure 31B:
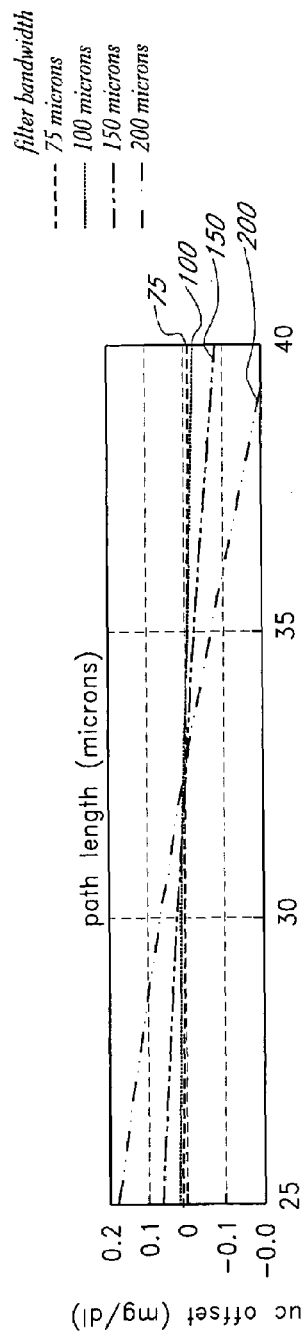
Figure 31C:
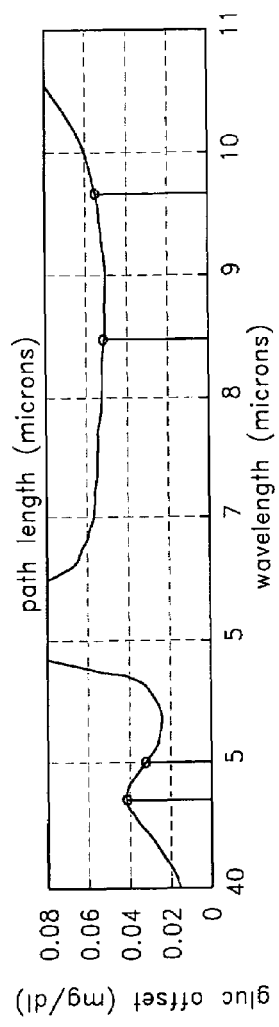
FIG. 31C is a graph of the absorption spectrum with the second set of wavelengths used in the calculation denoted by vertical lines.

FIGS. 31A and 31B are graphs of the uncorrected and corrected glucose error, respectively, as a function of path length for different filter bandwidths for a first set of wavelengths. FIG. 31C is a graph of the absorption spectrum with the first set of wavelengths used in the calculation denoted by vertical lines. In the calculation, each wavelength had identical gaussian-shaped filters with the filter bandwidth equal to the full-width-half-maximum (FWHM).

c. Water Temperature Sensitivity

Figure 32:
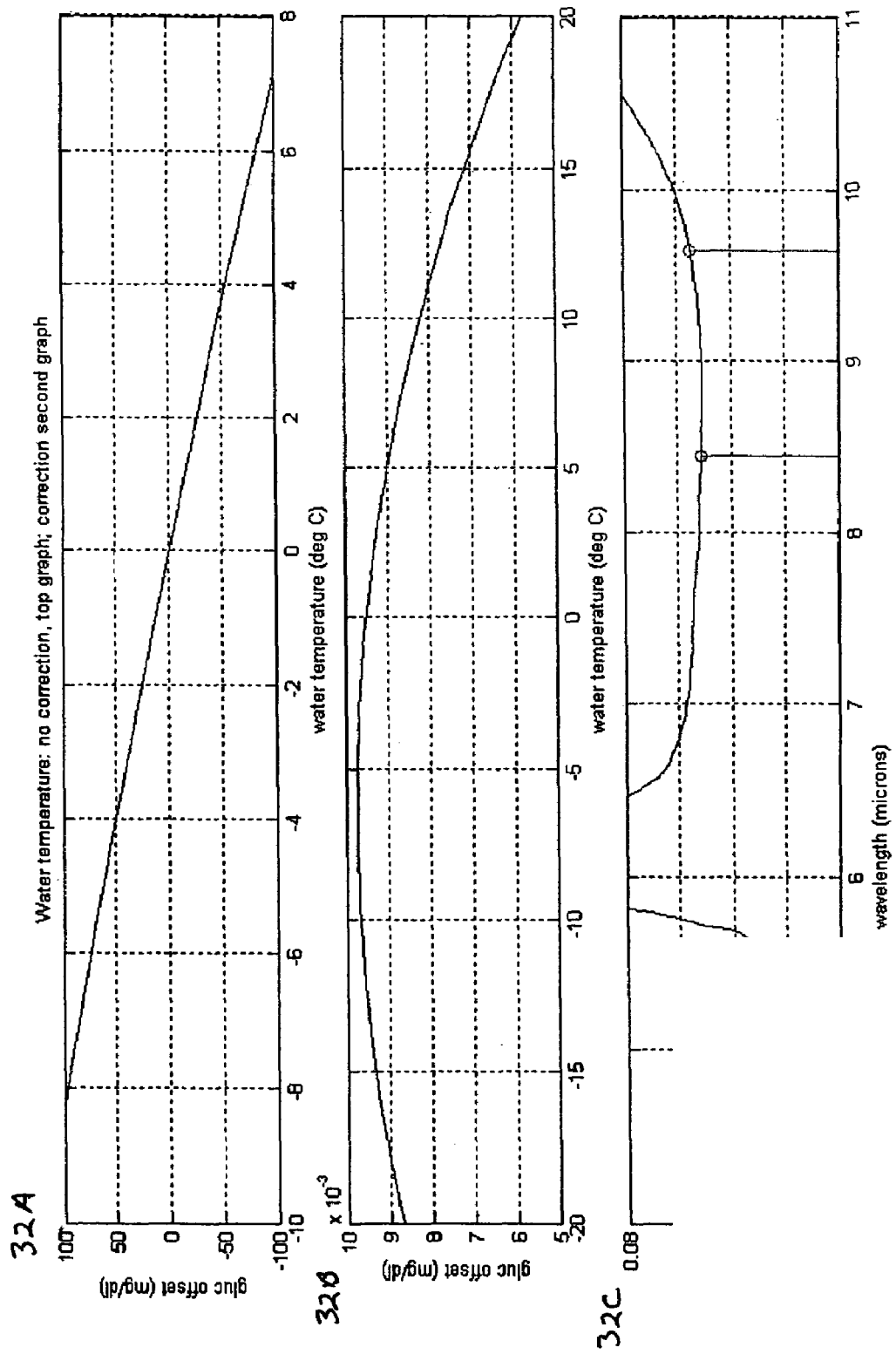
FIGS. 32A and 32B are graphs of the uncorrected and corrected glucose error, respectively, as a function of water temperature variation from nominal for a first set of wavelengths.
FIG. 32C is a graph of the absorption spectrum with the first set of wavelengths used in the calculation denoted by vertical lines.

FIGS. 32A and 32B are graphs of the uncorrected and corrected glucose error, respectively, as a function of water temperature variation from nominal for a first set of wavelengths. FIG. 32C is a graph of the absorption spectrum with the first set of wavelengths used in the calculation denoted by vertical lines.

Figure 33:
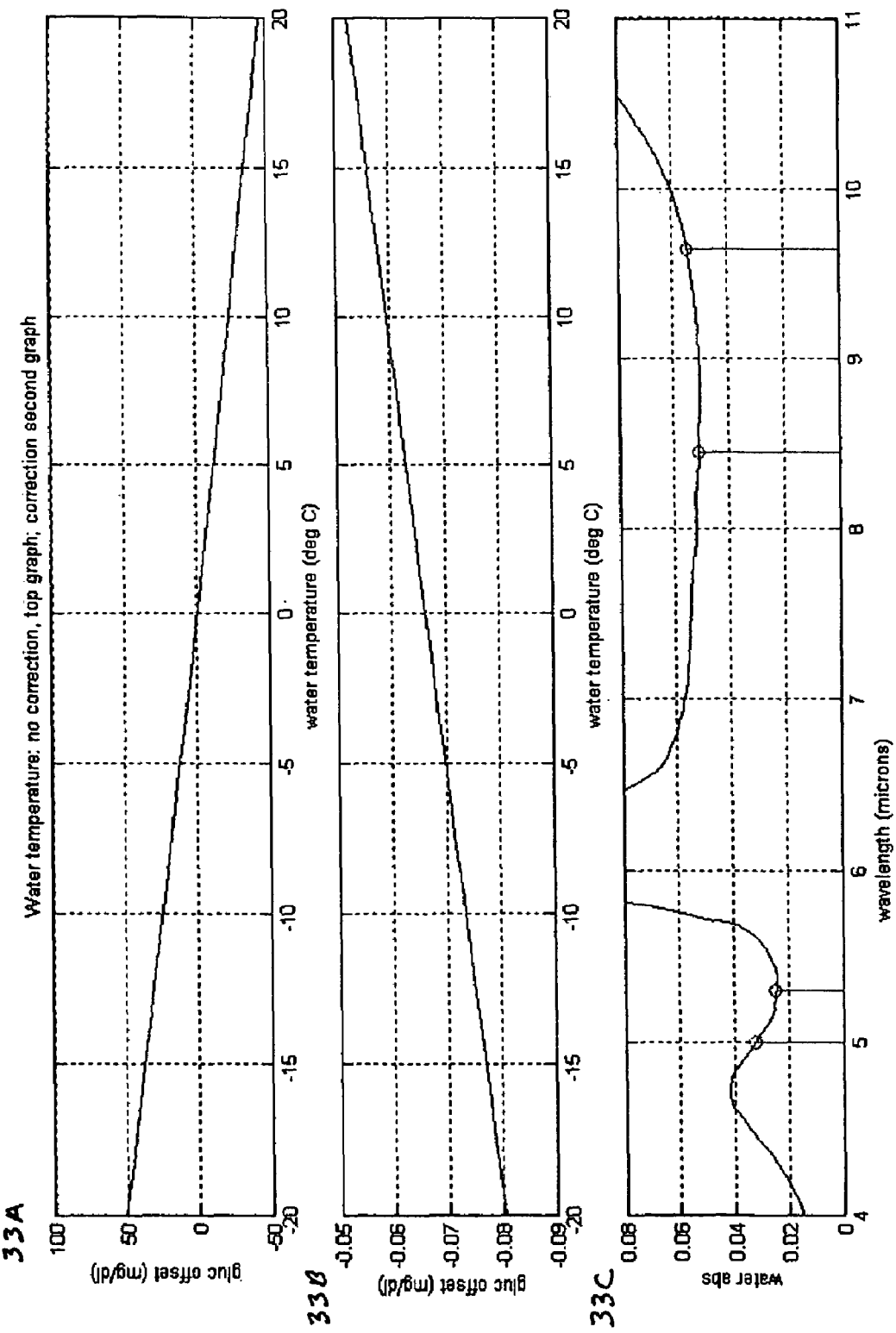
FIGS. 33A and 33B are graphs of the uncorrected and corrected glucose error, respectively, as a function of water temperature variation from nominal for a second set of wavelengths.
FIG. 33C is a graph of the absorption spectrum with the second set of wavelengths used in the calculation denoted by vertical lines.

FIGS. 33A and 33B are graphs of the uncorrected and corrected glucose error, respectively, as a function of water temperature variation from nominal for a first set of wavelengths. FIG. 33C is a graph of the absorption spectrum with the first set of wavelengths used in the calculation denoted by vertical lines. Water temperature sensitivity is minimum at 5.0 microns.

d. Filter Temperature Sensitivity

Figure 34A:
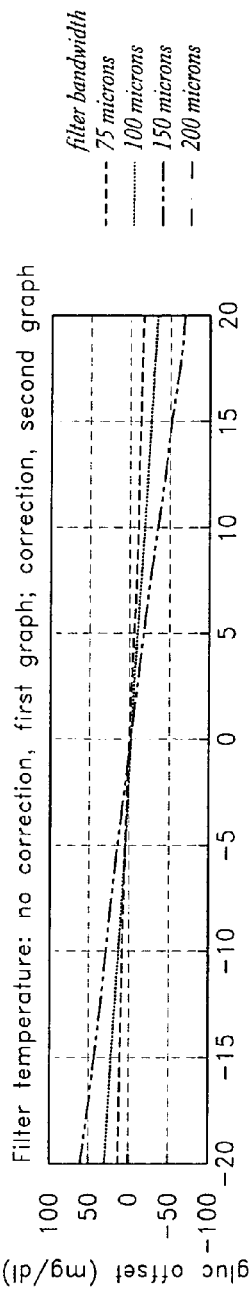
FIGS. 34A and 34B are graphs of the uncorrected and corrected glucose error, respectively, as a function of filter temperature variation from nominal for a first set of wavelengths.
Figure 34B:
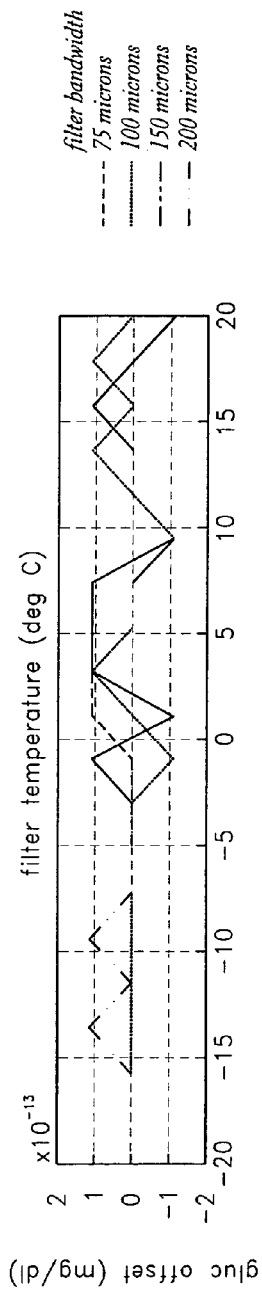
Figure 34C:
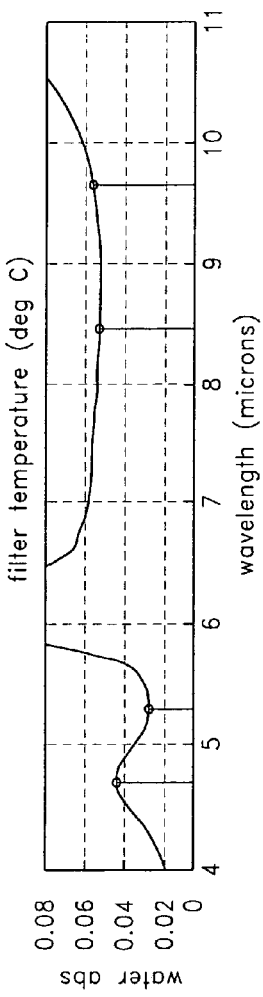
FIG. 34C is a graph of the absorption spectrum with the first set of wavelengths used in the calculation denoted by vertical lines.

FIGS. 34A and 34B are graphs of the uncorrected and corrected glucose error, respectively, as a function of filter temperature variation from nominal for a first set of wavelengths. The legend of FIG. 34A shows the filter temperature sensitivity as a percentage of the center wavelength per degree Celsius. All filters in the calculation had the same temperature sensitivity. FIG. 34C is a graph of the absorption spectrum with the first set of wavelengths used in the calculation denoted by vertical lines.

Figure 35A:
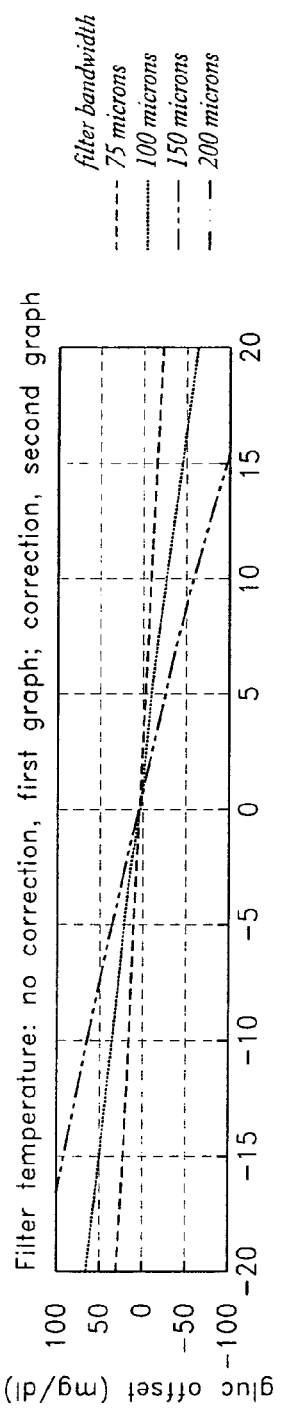
FIGS. 35A and 35B are graphs of the uncorrected and corrected glucose error, respectively, as a function of filter temperature variation from nominal for a second set of wavelengths.
Figure 35B:
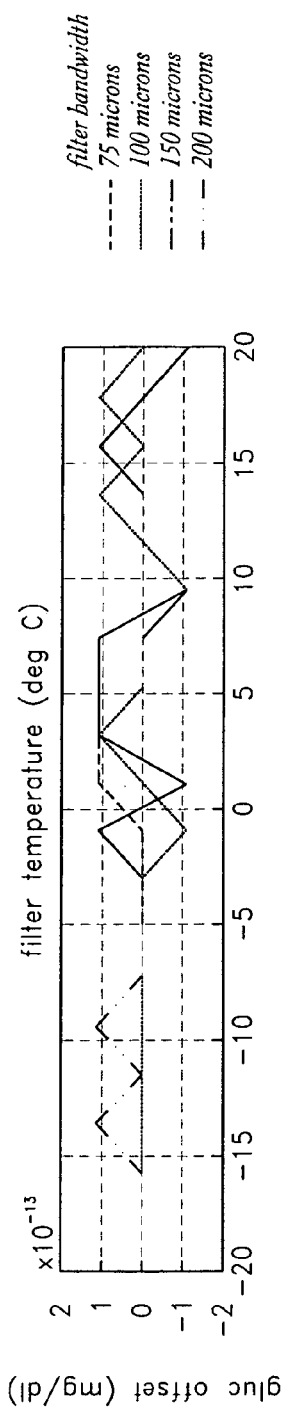
Figure 35C:
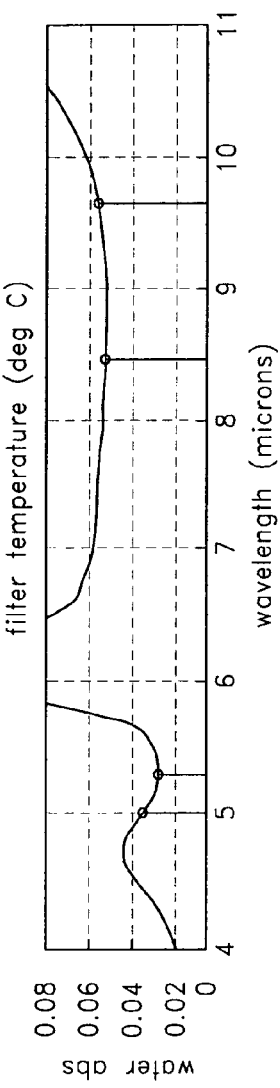
FIG. 35C is a graph of the absorption spectrum with the second set of wavelengths used in the calculation denoted by vertical lines.

FIGS. 35A and 35B are graphs of the uncorrected and corrected glucose error, respectively, as a function of filter temperature variation from nominal for a second set of wavelengths. The legend of FIG. 35A shows the filter temperature sensitivity as a percentage of the center wavelength per degree Celsius. All filters in the calculation had the same temperature sensitivity. FIG. 35C is a graph of the absorption spectrum with the second set of wavelengths used in the calculation denoted by vertical lines.

Further information can be found in U.S. Patent Application Publication No. 2003/0090649, published May 15, 2003, entitled "Reagent-Less Whole Blood Glucose Meter," U.S. patent application Ser. No. 10/319,409, filed Dec. 12, 2002, entitled "Pathlength-Independent Methods For Optically Determining Material Composition," U.S. patent application Ser. No. 10/366,540, filed Feb. 12, 2003, entitled "Method Of Determining An Analyte Concentration In A Sample From An Absorption Spectrum," and U.S. Provisional Patent No. 60/463,133, filed Apr. 15, 2003, entitled "Method Of Determining Analyte Concentration In A Blood Sample In A Cuvette Using Infrared Transmission Data." The entire contents of these patent applications is hereby incorporated herein in its entirety by this reference and is made a part of this specification.

V. Performance

The various embodiments of the analyte detection system 10 disclosed above have been found to facilitate highly and consistently accurate measurements of the concentrations of various analytes, such as glucose, in a material sample S, such as whole blood. Both the structure of the analyte detection system 10 and the various methods of operation disclosed herein contribute to the high performance and accuracy of the analyte detection system 10. Generally, increasing accuracy will be observed by employing one of the disclosed embodiments of the analyte detection system 10 with as many of the above-described methods as possible. However, no one embodiment, component or method is considered essential.

High measurement accuracy is promoted by the use of any of the methods disclosed above for (i) substantially removing the contribution of one or more chemical species other than the analyte of interest to the overall absorbance of the material sample under analysis; (ii) compensating for variability in optical pathlength through the material sample; (iii) substantially removing the contribution of the sample element to the overall absorbance of the sample element+ material sample system; (iv) adjusting for variability in the temperature of any water in the material sample; (v) adjusting for variability in the temperature of the optical filter(s) of the analyte detection system; (vi) adjusting for variations in the physical structure among the sample elements; and (vii) adjusting for time-dependent variance in the intensity of the radiation source. Of course, high measurement accuracy is promoted by the use of any combination of these methods.

Accordingly, certain embodiments of the analyte detection system 10 advantageously facilitates measurement of the concentration of an analyte, for example glucose, within a material sample, for example whole blood, blood components or processed blood. Such measurements preferably have a standard error (with a 95% confidence level) less than about 30 mg/dL, less than about 20 mg/dL, less than about 15 mg/dL, less than about 10 mg/dL, or equal to about 8.2 mg/dL, in various embodiments, when compared to corresponding measurements of the material sample's "actual" analyte concentration (as measured by a conventional laboratory-grade analyzer such as the type manufactured by Yellow Springs Instruments, Inc. of Yellow Springs, Ohio). In still other embodiments, the standard error is (when assessed under the same conditions) between about 30 mg/dL and about 8.2 mg/dL, between about 20 mg/dL and about 8.2 mg/dL, between about 15 mg/dL and about 8.2 mg/dL, or between about 10 mg/dL and about 8.2 mg/dL.

In some embodiments, the analyte detection system 10 performs such analyte-concentration measurements with accuracies corresponding to a RMS average error (when compared to "actual" measurements taken as discussed above) less than about 30 mg/dL, less than about 20 mg/dL, less than about 15 mg/dL, less than about 10 mg/dL, or equal to about 8.0 mg/dL. In still other embodiments, the RMS average error is (when assessed under the same conditions) between about 30 mg/dL and about 8.0 mg/dL, between about 20 mg/dL and about 8.0 mg/dL, between about 15 mg/dL and about 8.0 mg/dL, or between about 10 mg/dL and about 8.0 mg/dL.

The analyte detection system 10 achieves some or all of the above accuracy measures with sample analysis times which do not exceed 45 seconds or 30 seconds, in various embodiments. As used herein, "analysis time" is a broad term and is used in its ordinary sense and includes, without limitation, the time period between (i) the first receipt of data from the material sample by the analyte detection system and (ii) the last receipt of data from the material sample by the analyte detection system.

The overall accuracy of embodiments of the analyte detection system 10 and of the methods for, inter alia, determining the concentration of analyte(s) in a sample independent of optical pathlength, as described above, alone or in combination, advantageously facilitate the use of sample elements that deviate from a specified or expected pathlength through the sample chamber. Previous conventional analyte detection systems and methods required precisely-constructed, relatively expensive sample elements to tightly control the optical pathlength through the sample chamber. By employing an embodiment of the analyte detection system 10 as disclosed herein, and/or the disclosed methods for, inter alia, determining the concentration of analyte(s) in a sample independent of optical pathlength, large numbers of measurements of analyte (e.g., blood glucose) concentrations can be facilitated relatively inexpensively by manufacturing or otherwise providing a relatively large quantity (for example, 1,000 or more) of sample elements with a relatively wide variation in pathlength (from sample element to sample element). Various embodiments of the disclosed devices and methods therefore make optical detection of blood analytes economical for use by everyday people, such as outpatient diabetics who need to self-monitor their blood glucose levels. These sample elements which vary in pathlength can be employed with embodiments of systems and methods described herein to measure analyte concentrations on a large scale without substantial losses of accuracy among the individual measurements. In one embodiment, these analyte-concentration measurements taken with some or all of the quantity of sample elements yield clinically acceptable accuracy. (As used herein, the term "clinically acceptable accuracy" is a broad term and is used in its ordinary sense and includes, without limitation, (i) sufficient accuracy to meet requirements imposed by relevant regulatory authorities and/or medical practitioners; and/or (ii) sufficient accuracy to provide a satisfactory diagnostic result for device users.) In another embodiment, these analyte-concentrations measurements taken with some or all of the quantity of sample elements yield high accuracy as expressed by any of the measures of accuracy detailed above. In one embodiment, the analyte concentration measurements are made by employing any one or combination of the embodiments of sample elements as disclosed herein. In other embodiments, the sample elements employed may simply comprise a sample chamber defined by first and second walls, at least one of which is substantially transmissive of infrared radiation, wherein the sample elements have substantially uniform external dimensions and substantially uniform sample chamber volume.

In various embodiments, the sample elements can vary from a specified, expected, or mean pathlength by more than +/−1 micron, more than +/−2 microns, more than +/−4 microns, more than +/−5 microns, more than +/−8 microns, or by +/−10 microns. In other embodiments, the sample elements can vary from the specified/expected/mean pathlength by between +/−1 micron and +/−10 microns, between +/−2 microns and +/−10 microns, between +/−4 microns and +/−10 microns, between +/−5 microns and +/−10 microns, or between +/−8 microns and +/−10 microns. In still other embodiments, the quantity of sample elements can be characterized by a standard deviation in optical pathlength. In one such embodiment, the standard deviation is greater than or equal to about 0.256 microns. Such a standard deviation equates to a tolerance of greater than or equal to +/−1.0 microns where: (i) the pathlength errors are normally distributed with a mean error of zero microns; (ii) erroneous pathlengths which are smaller than a specified or expected pathlength are given a negative sense and erroneous pathlengths larger than a specified or expected pathlength are given a positive sense; and (iii) substantially 100% of the sample elements in the quantity are to fall within the stated tolerance. In other embodiments, the standard deviation is greater than or equal to about 0.512 microns, greater than or equal to about 1.024 microns, greater than or equal to about 1.280 microns, or greater than or equal to about 2.048 microns, corresponding to pathlength tolerances of greater than or equal to +/−2.0, 4.0, 5.0, or 8.0 microns, under the above-stated statistical conditions. In still other embodiments, the standard deviation is about 2.560 microns, corresponding to a pathlength tolerance of +/−about 10.0 microns, under the above-stated statistical conditions. In various other embodiments, the standard deviation is between 0.256 microns and 2.560 microns, between 0.512 microns and 2.560 microns, between 1.024 microns and 2.560 microns, between 1.280 microns and 2.560 microns, or between 2.048 microns and 2.560 microns.

In still other embodiments, the quantity of sample elements can be characterized by a standard deviation in optical pathlength, the standard deviation selected to implement a pathlength tolerance of greater than or equal to +/−1.0, 2.0, 4.0, 5.0, or 8.0 microns, or to implement a pathlength tolerance equal to about +/−10.0 microns, under the statistical conditions which prevail in the quantity of sample elements, and in light of the proportion (substantially 100%, for example, or some proportion less than substantially 100%) of sample elements which is desired to fall within the applicable pathlength tolerance. Alternatively, the quantity of sample elements can be characterized by a standard deviation in optical pathlength, the standard deviation being selected to implement a pathlength tolerance between (i) any of +/−1.0/2.0/4.0/5.0/8.0 microns and (ii) +/−10.0 microns, under the statistical conditions which prevail in the quantity of sample elements, and in light of the proportion (substantially 100%, for example, or some proportion less than substantially 100%) of sample elements which is desired to fall within the applicable pathlength tolerance. In any of the embodiments described herein, the standard deviation can comprise a population standard deviation within the quantity of sample elements, or a sample standard deviation measured among a subset of the quantity of sample elements. In addition, in any of the embodiments described herein, analyte-concentration measurements taken with some or all of the quantity of sample elements yield clinically acceptable accuracy. In another embodiment, analyte-concentration measurements taken with some or all of the quantity of sample elements yield high accuracy as expressed by any of the measures of accuracy detailed above.

As used herein with reference to a sample element having a sample chamber defined by opposed walls/windows, "optical pathlength" (or, alternatively, "pathlength") is a broad term and is used in its ordinary sense and includes, without limitation, the distance through the sample chamber from the inner surface of one wall/window to the inner surface of the opposing wall/window, as measured along (or parallel to) the optical axis of an energy beam passed through the sample chamber when the sample element is employed with a suitable analyte detection system. Where the pathlength varies within the sample chamber, the pathlength of the sample element in question may comprise an average pathlength. As used herein, "expected optical pathlength" (or, alternatively, "expected pathlength") is a broad term and is used in its ordinary sense and includes, without limitation, (i) a pathlength which has been recorded in the memory of a detection system for use in computing analyte concentrations; (ii) a pathlength specified for use in the detection system or class(es) of detection system(s) in question; and/or (iii) a pathlength at or near the center of a pathlength tolerance range specified for the detection system or class(es) of detection system(s) in question.

The overall accuracy of the analyte detection system 10 as described above and the methods for compensating for variability in optical pathlength through the material sample, alone or in combination, advantageously facilitate the use of sample elements wherein the windows that define the sample chamber deviate from a parallel orientation with respect to each other, or wherein one or both windows is nonplanar (due to being bowed or otherwise curved, or bent). Accordingly, certain embodiments described herein facilitate the use of a sample element (such as, but not limited to, the various embodiments disclosed above) with windows that define a sample chamber therebetween but deviate from a parallel orientation with respect to each other by more than about 1 micron. In further embodiments, the degree of deviation from parallel can be more than 2 microns, more than 4 microns, or can be about 8 microns. In still other embodiments, the degree of deviation from parallel can be between about 1 micron and about 8 microns, between about 2 microns and about 8 microns, or between about 4 microns and about 8 microns. In some embodiments, the degree of deviation from parallel comprises an average deviation from parallel.

Other embodiments facilitate the use of a sample element (such as, but not limited to, the various embodiments disclosed above) with at least one window that defines a sample chamber, wherein the window deviates from planarity by more than about 1 micron. In further embodiments, the degree of deviation from planarity can be more than 2 microns, more than 4 microns, or can be about 8 microns. In still other embodiments, the degree of deviation from planarity can be between about 1 micron and about 8 microns, between about 2 microns and about 8 microns, or between about 4 microns and about 8 microns. In some embodiments, the degree of deviation from planarity comprises an average deviation from planarity.

Where a sample element comprises two or more sample chambers, all of the preceding description relating to variation in optical pathlength, window planarity, etc. may apply to one, some or all of the sample chambers of the sample element in question.

Accordingly, the detection system 10 is configured to achieve exceptional accuracy with sample elements that are within the preferred pathlength design tolerance and have windows which are substantially planar and parallel. Additionally, the detection system 10 is configured to achieve adequate or even exceptional accuracy with problematic sample elements, like those with windows which are less planar or parallel, or that do not conform to the preferred pathlength design tolerance. In any of these embodiments of the sample element, an analyte-concentration measurement taken with the sample element yields clinically acceptable accuracy, and/or high accuracy as expressed by any of the accuracy measures detailed above.

While preferred embodiments of this invention have been disclosed herein, those skilled in the art will appreciate that changes and modifications may be made therein without departing from the spirit and scope of the invention as defined in the appended claims.

What is claimed is:

1. A method of determining an analyte concentration in a sample, the sample comprising the analyte and a substance, the method comprising:

providing absorption data of the sample;

providing reference absorption data of the substance;

calculating a substance contribution of the absorption data, wherein calculating the substance contribution comprises scaling the reference absorption data by multiplying the reference absorption data by a scaling factor, the scaling factor allowing for calculation of a pathlength-independent quality;

subtracting the substance contribution from the absorption data of the sample, thereby providing corrected absorption data of the analyte substantially free of a contribution from the substance;

using the corrected absorption data to calculate analyte concentration in the sample; and providing the analyte concentration to a user.

2. The method of claim 1, wherein providing the absorption data of the sample comprises:

providing transmittance data of the sample; and determining the absorption data from the transmittance data.

3. The method of claim 2, wherein providing the transmittance data of the sample comprises:

transmitting at least a portion of an infrared signal through the sample, the infrared signal comprising a plurality of wavelengths; and measuring the portion of the infrared signal transmitted through the sample as a function of wavelength.

4. The method of claim 3, wherein providing the transmittance data further comprises placing the sample in a cuvette.

5. The method of claim 2, wherein the sample comprises blood.

6. The method of claim 5, wherein the analyte comprises glucose, and the selected transmittance wavelength range comprises wavelengths at which the transmittance data is dominated by water transmittance.

7. The method of claim 2, wherein the sample comprises plasma.

8. The method of claim 7, wherein the analyte comprises glucose, and the selected transmittance wavelength range comprises wavelengths at which the transmittance data is dominated by water transmittance.

9. The method of claim 1, wherein the substance comprises water.

10. The method of claim 1, wherein the substance interferes with determining the analyte concentration.

11. The method of claim 10, wherein the sample further comprises a second substance which interferes with determining the analyte concentration to a lesser extent than does the substance, the method further comprising calculating a second substance contribution of the absorption data and subtracting the second substance contribution from the absorption data, thereby providing twice-corrected absorption data substantially free of contributions from the substance and from the second substance.

12. The method of claim 1, wherein the reference absorption data is corrected for temperature-dependent effects.

13. A method of determining an analyte concentration in a sample, the sample comprising the analyte and a substance, the method comprising:

providing absorption data of the sample;

providing reference absorption data of the substance;

calculating a substance contribution of the absorption data, wherein calculating the substance contribution comprises scaling the reference absorption data by multiplying the reference absorption data by a scaling factor;

subtracting the substance contribution from the absorption data of the sample, thereby providing corrected absorption data of the analyte substantially free of a contribution from the substance, wherein the reference absorption data is corrected for wavelength-dependent nonlinearities; and storing the corrected absorption data in a memory.

14. The method of claim 13, wherein the sample is contained within a sample element and the wavelength-dependent nonlinearities are generated by scattering from the sample element.

15. The method of claim 13, wherein the sample is contained within a sample element and the wavelength-dependent nonlinearities are generated by fringing from the sample element.

16. The method of claim 1, wherein scaling the reference absorption data utilizes at least two wavelength ranges.

17. The method of claim 1, wherein the sample comprises a second substance, and the method further comprises subtracting a second contribution corresponding to the second substance from the corrected absorption data, thereby providing twice-corrected absorption data substantially free of contributions from the substance and from the second substance.

18. The method of claim 17, wherein subtracting the second contribution comprises:

providing second reference absorption data corresponding to the second substance;

scaling the second reference absorption data by multiplying the second reference absorption data by a second scaling factor; and subtracting the scaled second reference absorption data from the corrected absorption data, thereby providing the twice-corrected absorption data.

19. The method of claim 18, wherein the second substance comprises a whole blood protein.

20. The method of claim 18, wherein the second substance comprises components of a boundary layer between water and a whole blood protein.

21. The method of claim 18, wherein the second substance comprises urea or lactate.

22. The method of claim 17, further comprising fitting the twice-corrected absorption data with analyte spectral data, thereby yielding a measurement of the analyte concentration in the sample.

23. The method of claim 22, wherein the twice-corrected absorption data is fitted with reference analyte spectral data.

24. A method of providing measurements of constituents in a sample using infrared (IR) spectroscopy, the method comprising:

providing absorption data of the sample, wherein providing absorption data comprises:

placing the sample in a cuvette having a shape;

passing IR radiation through a filter having a finite width;

irradiating the cuvette with the IR radiation; and detecting a fraction of the IR radiation transmitted through the cuvette and the sample;

correcting the absorption data for a non-analyte contribution to the absorption data, wherein the non-analyte contribution is from the finite width of the filter; and providing the corrected absorption data to a user.

25. A method of providing measurements of constituents in a sample using infrared (IR) spectroscopy, the method comprising:

providing absorption data of the sample, wherein providing absorption data comprises:

placing the sample in a cuvette having a shape;

passing IR radiation through a filter having a finite width;

irradiating the cuvette with the IR radiation; and detecting a fraction of the IR radiation transmitted through the cuvette and the sample;

correcting the absorption data for a non-analyte contribution to the absorption data, wherein the non-analyte contribution is from the shape of the cuvette; and storing the corrected absorption data in a memory.

26. The method of claim 25, wherein the sample comprises blood.

27. The method of claim 25, wherein the sample comprises plasma.

28. A method of using infrared (IR) spectroscopy to determine a ratio of an analyte volume to the total volume of a sample comprising the analyte, a first substance, and a second substance, the method comprising:

providing absorption data from the sample for a first set of wavelengths in a wavelength region where a first-substance absorption dominates;

calculating a first quantity equal to the product of a first-substance volume concentration and a path length of the sample;

providing absorption data from the sample for a second set of wavelengths in a wavelength region where the first-substance absorption and a second-substance absorption dominate;

calculating a second quantity equal to the product of a second-substance volume concentration and the path length of the sample;

providing absorption data from the sample for a third set of wavelengths in a wavelength region where the first-substance absorption, the second-substance absorption, and an analyte absorption dominate;

calculating a third quantity equal to the product of an analyte volume concentration and the path length of the sample;

calculating a ratio of the third quantity divided by the sum of the first quantity, the second quantity, and the third quantity to achieve a pathlength-independent quantity; and storing the ratio in a memory.

29. The method of claim 28, wherein the analyte comprises glucose.

30. The method of claim 28, wherein the first substance comprises water.

31. The method of claim 28, wherein the second substance comprises hematocrit soup.

32. The method of claim 28, wherein the second substance comprises hemoglobin.

33. The method of claim 28, wherein the second substance comprises red blood cells.

34. A method of determining non-analyte contributions to absorption data from a sample, the method comprising:

(a) inputting transmission measurements, filter parameters, and water spectral properties;

(b) calculating optical densities and filter constants;

(c) estimating non-linear filter terms and cuvette distortion matrix elements;

(d) solving for a temperature change as a function of the path length; and (e) calculating new estimates of absorption and non-linear terms.

35. The method of claim 34, further comprising repeating (d) and (e) until the solution converges to a desired accuracy.

36. The method of claim 34, wherein the sample comprises blood.

37. The method of claim 34, wherein the sample comprises plasma.

38. A method of determining non-analyte contributions to absorption data from a sample, the method comprising:

(a) inputting transmission measurements, filter parameters, and water spectral properties;

(b) calculating optical densities and filter constants;

(c) estimating non-linear filter terms and cuvette distortion matrix elements;

(d) solving for a temperature change as a function of the path length; and (e) calculating new estimates of absorption and non-linear terms.

39. The method of claim 38, further comprising repeating (d) and (e) until the solution converges to a desired accuracy.

40. A method of evaluating analyte concentration errors in absorption data from a sample, the method comprising:

calculating transmission and optical densities at four wavelengths for a water-filled cuvette, the four wavelengths comprising two wavelengths dominated by absorption by water, an analyte reference wavelength, and a measurement wavelength;

using the optical densities to determine the water content at the analyte reference wavelength and the measurement wavelength;

calculating expected optical density values at the analyte reference wavelength and the measurement wavelength;

calculating residuals between the exact and calculated optical densities at the analyte reference wavelength and the measurement wavelength;

determining the analyte concentration error by calculating the analyte concentration consistent with the difference between the residuals at the analyte reference wavelength and the measurement wavelength; and storing the analyte concentration error in a memory.

41. The method of claim 40, wherein the sample comprises blood.

42. The method of claim 40, wherein the sample comprises plasma.

43. The method of claim 40, wherein the analyte comprises glucose.

* * * * *